United States Patent
Gu et al.

(10) Patent No.: US 12,264,148 B2
(45) Date of Patent: Apr. 1, 2025

(54) IVOSIDENIB FORMS AND PHARMACEUTICAL COMPOSITIONS

(71) Applicant: Servier Pharmaceuticals LLC, Boston, MA (US)

(72) Inventors: Chong-Hui Gu, Waban, MA (US); Jacob Paul Sizemore, Grayslake, IL (US); Shijie Zhang, Nashua, NH (US)

(73) Assignee: Servier Pharmaceuticals LLC, Boston, MA (US)

( * ) Notice: Subject to any disclaimer, the term of this patent is extended or adjusted under 35 U.S.C. 154(b) by 872 days.

(21) Appl. No.: 17/258,102

(22) PCT Filed: Jul. 2, 2019

(86) PCT No.: PCT/US2019/040257
§ 371 (c)(1),
(2) Date: Jan. 5, 2021

(87) PCT Pub. No.: WO2020/010058
PCT Pub. Date: Jan. 9, 2020

(65) Prior Publication Data
US 2021/0323944 A1    Oct. 21, 2021

Related U.S. Application Data

(60) Provisional application No. 62/694,596, filed on Jul. 6, 2018.

(51) Int. Cl.
*C07D 401/14* (2006.01)
*A61K 9/20* (2006.01)

(52) U.S. Cl.
CPC .......... *C07D 401/14* (2013.01); *A61K 9/2027* (2013.01); *A61K 9/2054* (2013.01); *C07B 2200/13* (2013.01)

(58) Field of Classification Search
CPC .. C07D 401/14; A61K 9/2027; A61K 9/2054; A61K 31/444; A61K 47/06; A61K 47/14; C07B 2200/13; A61P 35/00
USPC ........................................................ 514/333
See application file for complete search history.

(56) References Cited

U.S. PATENT DOCUMENTS

| 9,968,595 B2 | 5/2018 | Gu |
| 2012/0121515 A1 | 5/2012 | Dang et al. |
| 2013/0190249 A1 | 7/2013 | Lemieux et al. |

FOREIGN PATENT DOCUMENTS

| IN | 201811011325 | * | 3/2018 | ............. A61P 35/00 |
| WO | 2011/050210 A1 | | 4/2011 | |
| WO | 2013/107291 A1 | | 7/2013 | |
| WO | 2015/138839 A1 | | 9/2015 | |
| WO | 2017/146795 A1 | | 8/2017 | |
| WO | 2019/104318 A1 | | 5/2019 | |

OTHER PUBLICATIONS

Poojary, D. M., & Clearfield, A.. Application of X-ray Powder Diffraction Techniques to the Solution of Unknown Crystal Structures. Accounts of Chemical Research, 30(10), 414-422. https://doi.org/10.1021/ar960143j (Year: 1997).*
Dang et al., "Cancer-associated IDH1 mutations produce 2-hydroxyglutarate", Nature, 2009, 462, 739-744.
Geisbrecht et al., "The Human PICD Gene Encodes a Cytoplasmic and Peroxisomal NADP1-dependent Isocitrate Dehydrogenase", J. Biol. Chem., 1999, 274, 30527-30533.
Nekrutenko et al., "Cytosolic Isocitrate Dehydrogenase in Humans, Mice, and Voles and Phylogenetic Analysis of the Enzyme Family", Mol. Biol. Evol., 1998, 15, 1674-1684.
Rohle et al., "An Inhibitor of Mutant IDH1 Delays Growth and Promotes Differentiation of Glioma Cells", Science, 2013, 340, 626-630.
Sjoeblom et al., "The Consensus Coding Sequences of Human Breast and Colorectal Cancers", Science, 2006, 314, 268-274.
The MGC Project Team, "The Status, Quality, and Expansion of the NIH Full-Length cDNA Project: The Mammalian Gene Collection (MGC)", Genome Res., 2004, 14, 2121-2127.
Wiemann et al., "Toward a Catalog of Human Genes and Proteins: Sequencing and Analysis of 500 Novel Complete Protein Coding Human cDNAs", Genome Res., 2001, 11, 422-435.
Lee, E., "A practical guide to pharmaceutical polymorph screening & selection", Asian Journal of Pharmaceutical Sciences, May 16, 2014, vol. 9, No. 4, pp. 163-175.
Caira, M., "Crystalline Polymorphism of Organic Compounds", Topics in Current Chemistry, vol. 198, pp. 163-208, Jan. 1, 1998.

* cited by examiner

*Primary Examiner* — Yih-Horng Shiao
*Assistant Examiner* — Hoi Yan Lee
(74) *Attorney, Agent, or Firm* — Goodwin Procter LLP

(57) ABSTRACT

Provided are formulations of ivosidenib including a number of polymorphs. Further provided are formulations of ivosidenib containing a number of known impurities. Still further provided are stable compositions of ivosidenib.

5 Claims, 23 Drawing Sheets

IVOSIDENIB FORMS AND PHARMACEUTICAL COMPOSITIONS

CROSS-REFERENCE TO RELATED APPLICATIONS

This application is a U.S. 371 National Stage Application of International Patent Application No. PCT/US2019/040257, filed Jul. 2, 2019, which claims the benefit of U.S. Provisional Patent Application No. 62/694,596, filed Jul. 6, 2018, the entire contents of both are hereby incorporated herein by reference.

BACKGROUND

Isocitrate dehydrogenases (IDHs) catalyze the oxidative decarboxylation of isocitrate to 2-oxoglutarate (i.e., α-ketoglutarate). These enzymes belong to two distinct subclasses, one of which utilizes NAD(+) as the electron acceptor and the other NADP(+). Five isocitrate dehydrogenases have been reported: three NAD(+)-dependent isocitrate dehydrogenases, which localize to the mitochondrial matrix, and two NADP(+)-dependent isocitrate dehydrogenases, one of which is mitochondrial and the other predominantly cytosolic. Each NADP(+)-dependent isozyme is a homodimer.

IDH1 (isocitrate dehydrogenase 1 (NADP+), cytosolic) is also known as IDH; IDP; IDCD; IDPC or PICD. The protein encoded by this gene is the NADP(+)-dependent isocitrate dehydrogenase found in the cytoplasm and peroxisomes. It contains the PTS-1 peroxisomal targeting signal sequence. The presence of this enzyme in peroxisomes suggests roles in the regeneration of NADPH for intraperoxisomal reductions, such as the conversion of 2, 4-dienoyl-CoAs to 3-enoyl-CoAs, as well as in peroxisomal reactions that consume 2-oxoglutarate, namely the alpha-hydroxylation of phytanic acid. The cytoplasmic enzyme serves a significant role in cytoplasmic NADPH production.

The human IDH1 gene encodes a protein of 414 amino acids. The nucleotide and amino acid sequences for human IDH1 can be found as GenBank entries NM_005896.2 and NP_005887.2 respectively. The nucleotide and amino acid sequences for IDH1 are also described in, e.g., Nekrutenko et al., Mol. Biol. Evol. 15:1674-1684(1998); Geisbrecht et al., J. Biol. Chem. 274:30527-30533(1999); Wiemann et al., Genome Res. 11:422-435(2001); The MGC Project Team, Genome Res. 14:2121-2127(2004); Lubec et al., Submitted (December 2008) to UniProtKB; Kullmann et al., Submitted (June 1996) to the EMBL/GenBank/DDBJ databases; and Sjoeblom et al., Science 314:268-274(2006).

Non-mutant, e.g., wild type, IDH1 catalyzes the oxidative decarboxylation of isocitrate to α-ketoglutarate.

It has been discovered that mutations of IDH1 present in certain cancer cells result in a new ability of the enzyme to catalyze the NADPH-dependent reduction of α-ketoglutarate to R(−)-2-hydroxyglutarate (2HG). The production of 2HG is believed to contribute to the formation and progression of cancer (Dang, L et al., Nature 2009, 462:739-44).

IDH2 (isocitrate dehydrogenase 2 (NADP+), mitochondrial) is also known as IDH; IDP; IDHM; IDPM; ICD-M; or mNADP-IDH. The protein encoded by this gene is the NADP(+)-dependent isocitrate dehydrogenase found in the mitochondria. It plays a role in intermediary metabolism and energy production. This protein may tightly associate or interact with the pyruvate dehydrogenase complex. Human IDH2 gene encodes a protein of 452 amino acids. The nucleotide and amino acid sequences for IDH2 can be found as GenBank entries NM_002168.2 and NP_002159.2 respectively. The nucleotide and amino acid sequence for human IDH2 are also described in, e.g., Huh et al., Submitted (November 1992) to the EMBL/GenBank/DDBJ databases; and The MGC Project Team, Genome Res. 14:2121-2127(2004).

Non-mutant, e.g., wild type, IDH2 catalyzes the oxidative decarboxylation of isocitrate to α-ketoglutarate (α-KG).

It has been discovered that mutations of IDH2 present in certain cancer cells result in a new ability of the enzyme to catalyze the NADPH-dependent reduction of α-ketoglutarate to R(−)-2-hydroxyglutarate (2HG). 2HG is not formed by wild-type IDH2. The production of 2HG is believed to contribute to the formation and progression of cancer (Dang, L et al, Nature 2009, 462:739-44).

Mutations in IDH1 or IDH2 occur in over 70% of diffuse low grade glioma (LGG) tumors. IDH mutations result in accumulation of 2-HG, which is believed to facilitate tumorigenesis through DNA hypermethylation, increased repressive histone methylation, and inhibition of differentiation processes. Studies performed with a tool compound known as AGI-5198, which has been shown to inhibit mutant IDH1 (mIDH1), but not mutant IDH2 (mIDH2), have demonstrated that inhibition of mIDH1 proteins can repress growth of mIDH1-driven gliomas in some model systems (D. Rohle et al. Science 340:626-630 (2013)).

U.S. Publication No. 2013/0190249 A1 discloses a compound described by the chemical name (S)—N—((S)-1-(2-Chlorophenyl)-2-(3,3-difluorocyclobutylamino)-2-oxo-ethyl)-1-(4-cyanopyridin-2-yl)-N-(5-fluoropyridin-3-yl)-5-oxopyrrolidine-2-carboxamide, which has been shown to act as an inhibitor of mutant IDH1 proteins in biochemical and cellular assays. Depending upon naming convention, this compound also may be referred to as (2S)—N-{(1S)-1-(2-chlorophenyl)-2-[(3,3-difluorocyclobutyl)amino]-2-oxo-ethyl}-1-(4-cyanopyridin-2-yl)-N-(5-fluoropyridin-3-yl)-5-oxopyrrolidine-2-carboxamide. Further, in 2015, the INN assigned the compound to the name: ivosidenib. The structure of ivosidenib is described herein as formula (I):

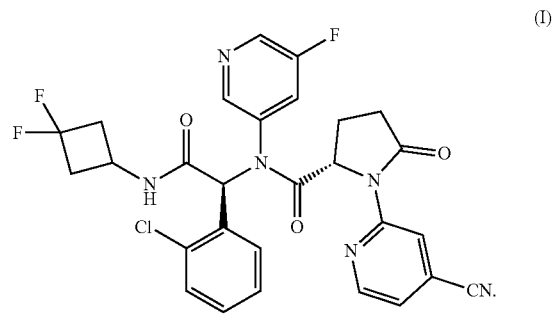 [SMILES: N#Cc1ccnc(N2C(=O)CC[C@H]2C(=O)N(c2cncc(F)c2)[C@H](C(=O)NC2CC(F)(F)C2)c2ccccc2Cl)c1]

In this application, "ivosidenib" and a "compound of formula (I)" are used interchangeably.

SUMMARY OF INVENTION

One aspect of the present disclosure provides various solid state forms of a compound of formula (I):

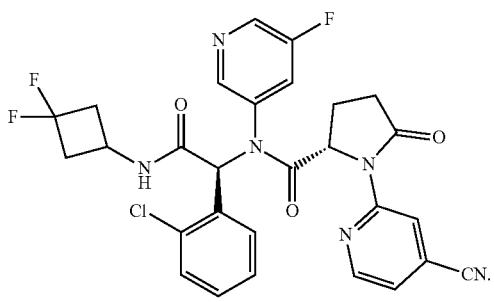

(I)

wherein each solid state form individually may be anhydrous, a hydrate or a solvate. In some embodiments the solid state forms are denoted Forms E, G, M, or N wherein each form individually may be anhydrous, a hydrate or a solvate. One embodiment of the present disclosure is Form E of a compound of formula (I):

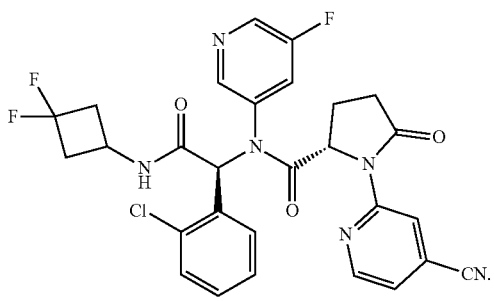

(I)

or a hydrate or solvate thereof. In one embodiment Form E is a solvated form. In another embodiment Form E is an isopropyl acetate solvate of a compound of Formula I.

One embodiment of the present disclosure is Form G of a compound of formula (I):

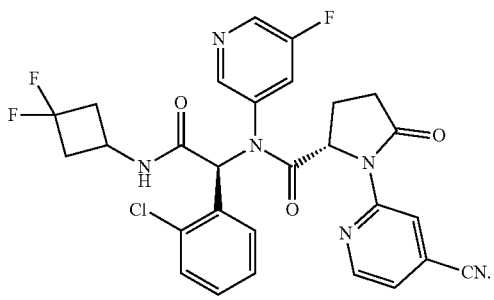

(I)

or a hydrate or solvate thereof. In another embodiment Form G is a solvated or hydrated form of the compound of Formula I.

One embodiment of the present disclosure is Form M of a compound of formula (I):

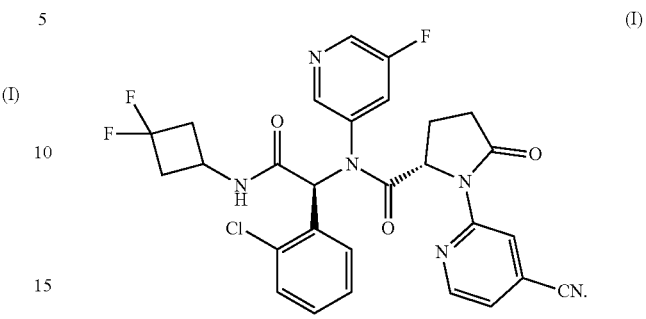

(I)

or a hydrate or solvate thereof. In another embodiment Form M is an anhydrous form of the compound of Formula I.

One embodiment of the present disclosure is a Form N of a compound of formula (I):

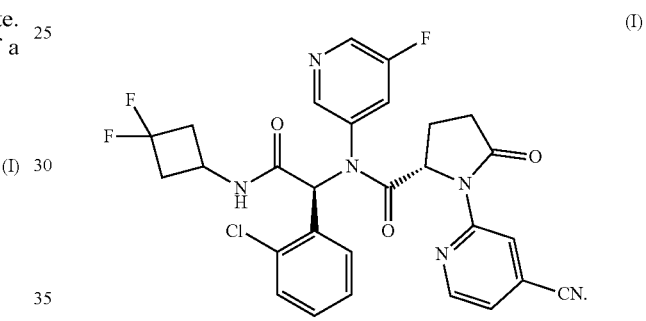

(I)

or a hydrate or solvate thereof. In another embodiment Form N is an anhydrous form of a compound of Formula I.

One embodiment of the present disclosure is a pharmaceutical composition comprising one or more of the Forms E, G, M, or N, each individually in an anhydrous, hydrated, or solvated form.

Another aspect of the present disclosure provides one or more solid state forms of the compound of Formula I

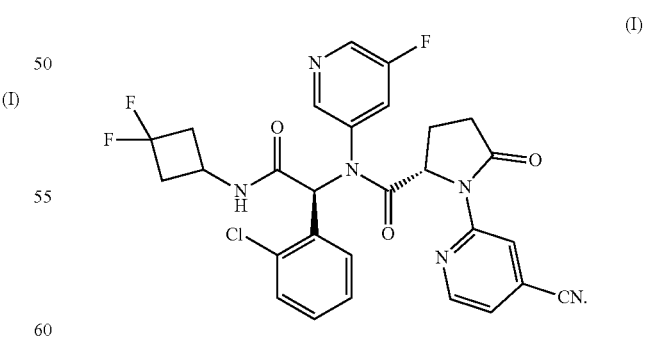

(I)

that are partially crystalline. In one embodiment, the one or more partially crystalline forms are chosen from A, C, D, E, F, G, H, I, J, K, M, or N or a hydrate or solvate thereof. In one embodiment, the one or more partially crystalline form is chosen from Forms A, I, or K, each individually in an anhydrous, hydrated or solvated form. In other embodiments, the one or more partially crystalline form is chosen from Form L or Form B, each individually in an anhydrous, hydrated or solvated form.

In one embodiment of the present disclosure, the partially crystalline form is at least 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, or 99.9% crystalline form B. In another embodiment, the partially crystalline form is at least 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, or 99.9% crystalline form L. In another embodiment, the partially crystalline form is at least 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, or 99.9% crystalline form A. In another embodiment, the partially crystalline form is at least 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, or 99.9% crystalline form I. In another embodiment, the partially crystalline form is at least 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, or 99.9% crystalline form K.

In another aspect, the present disclosure provides a process for making Form L of ivosidenib comprising making one or more meta-stable forms of ivosidenib in an anhydrous, hydrated, or solvated form, and allowing such one or more meta-stable form of ivosidenib to convert to Form L. One aspect provides a process where the one or more meta-stable form is selected from forms C, D, E, F, H, J, M, or N, each individually in an anhydrous, hydrated, or solvated form.

In another aspect, the present disclosure provides a pharmaceutical composition comprising ivosidenib in a mixture of two or more solid state forms chosen from Form L, Form B, Form A, Form C, Form D, Form E, Form F, Form G, Form H, Form I, Form J, Form K, Form M, and Form N, each individually in an anhydrous, hydrated, or solvated form. In one aspect, the pharmaceutical composition comprises no more than 0.15% (area % by HPLC) of a compound selected from: (i) 2-((2S)-2-((1-(2-chlorophenyl)-2-((3,3-difluorocyclobutyl)amino)-2-oxoethyl)(5-fluoropyridin-3-yl)carbamoyl)-5-oxopyrrolidin-1-yl)isonicotinamide; (ii) (S)—N—((S)-1-(2-chlorophenyl)-2-((3,3-difluorocyclobutyl)amino)-2-oxoethyl)-1-(4-cyanopyridin-2-yl)-5-oxo-N-(pyridin-3-yl)pyrrolidine-2-carboxamide; (iii) (S)—N—((R)-1-(2-Chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide; (iv) (R)—N—((S)-1-(2-Chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide; and (v) (R)—N—((R)-1-(2-Chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide. In one aspect, the pharmaceutical composition comprises Form L together with one or more of Form B, Form A, Form C, Form D, Form E, Form F, Form G, Form H, Form I, Form J, Form K, Form M, and Form N, each individually in an anhydrous, hydrated, or solvated form. In another aspect, the pharmaceutical composition may optionally contain amorphous ivosidenib. In yet another aspect, the pharmaceutical composition comprises one or more forms of ivosidenib that are chosen from Form B, Form A, Form C, Form D, Form E, Form F, Form G, Form H, Form I, Form J, Form K, Form M, or Form N, each individually in an anhydrous, hydrated, or solvated form and the pharmaceutical composition is substantially free of Form L. In other embodiments, such compositions may optionally contain amorphous ivosidenib. In another embodiment, the pharmaceutical composition comprises one of Form L or Form B, each individually in an anhydrous, hydrated, or solvated form, together with amorphous ivosidenib. In some embodiments Form L is an anhydrous form. In other embodiments Form B is a hydrate or a solvate form. In still other embodiments, the pharmaceutical composition comprises up to about 10% w/w of either Form L or Form B, each individually in an anhydrous, hydrated, or solvated form, together with amorphous ivosidenib. In yet other embodiments, the pharmaceutical composition comprises up to about 6% w/w of either Form L or Form B, each individually in an anhydrous, hydrated, or solvated form, together with amorphous ivosidenib.

In another aspect, the present disclosure provides a solid dosage form comprising a Form L drug product, where the Form L drug product is created via any one or more of Form B, Form A, Form C, Form D, Form E, Form F, Form G, Form H, Form I, Form J, Form K, Form M, or Form N, each individually in an anhydrous, hydrated, or solvated form. In another aspect, the solid dosage form includes a Form L drug product, which contains Form L and one or more of Form B, Form A, Form C, Form D, Form E, Form F, Form G, Form H, Form I, Form J, Form K, Form M, or Form N, each individually in an anhydrous, hydrated, or solvated form. In some embodiments the solid dosage form optionally contains amorphous ivosidenib.

In another aspect, the present disclosure provides a solid dosage form comprising a substantially amorphous drug product intermediate and further comprising any one or more of Form A, Form C, Form D, Form E, Form F, Form G, Form H, Form I, Form J, Form K, Form M, or Form N, each individually in an anhydrous, hydrated, or solvated form.

In another aspect, the present disclosure provides a solid dosage form comprising ivosidenib in a substantially amorphous form and further comprising any one or more of crystalline Form L, Form B, Form A, Form C, Form D, Form E, Form F, Form G, Form H, Form I, Form J, Form K, Form M, or Form N, each individually in anhydrous, hydrated, or solvated form, and one or more pharmaceutically acceptable excipients. In one aspect, the present disclosure provides a solid dosage form comprising ivosidenib in a substantially amorphous form that comprises no more than 0.15% (area % by HPLC) of a compound selected from: (i) 2-((2S)-2-((1-(2-chlorophenyl)-2-((3,3-difluorocyclobutyl)amino)-2-oxoethyl)(5-fluoropyridin-3-yl)carbamoyl)-5-oxopyrrolidin-1-yl)isonicotinamide; (ii) (S)—N—((S)-1-(2-chlorophenyl)-2-((3,3-difluorocyclobutyl)amino)-2-oxoethyl)-1-(4-cyanopyridin-2-yl)-5-oxo-N-(pyridin-3-yl)pyrrolidine-2-carboxamide; (iii) (S)—N—((R)-1-(2-Chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide; (iv) (R)—N—((S)-1-(2-Chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide; and (v) (R)—N—((R)-1-(2-Chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide. In another aspect, the solid dosage form further comprises a polymer chosen from hydroxypropylmethylcellulose (HPMC), hydroxypropylmethylcellulose phthalate (HPMCP), hydroxypropylmethylcellulose acetate succinate (HPMCAS), hydroxypropylcellulose (HPC), ethylcellulose, or cellulose acetate phthalate; polyvinylpyrrolidones (PVP); polyethylene glycols (PEG); polyvinyl alcohols (PVA), Polyvinyl Acetate Phthalate (PVAP); acrylates, polyvinylpyrrolidone-vinyl acetate (PVP-VA), polyvinyl caprolactam-polyvinyl, and acetate-polyethyleneglycol copolymer, Methylacrylate/methacrylic acid copolymer; Soluplus; Copovidone; and mixtures thereof. In another aspect, the polymer is chosen from HPMC, HPMCP, HPMCAS, PVAP and copovidone In another aspect, the present disclosure provides a solid dosage form comprising a substantially amorphous drug product intermediate that is made from any one or more of Form A, Form C, Form D, Form E, Form F, Form G, Form H, Form I, Form J, Form K, Form M, or Form N, each individually in an anhydrous, hydrated, or solvated form. In some embodiments the substantially amorphous drug product intermediate is a solid dispersion.

In another aspect, the present disclosure provides a compound selected from one of forms E, G, M, or N, of a compound of formula (I)

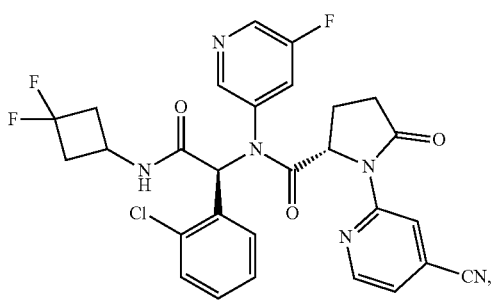

(I)

each individually in an anhydrous, hydrated, or solvated form that is substantially free of one or more of any other solid state forms of the compound of formula (I).

One aspect of the present disclosure provides a solid state form of ivosidenib that is Form E having an x-ray powder diffraction pattern comprising one peak, or two peaks, or three peaks, or four peaks, or five peaks, or six peaks, or seven peaks, or eight peaks, or nine peaks, in terms of 2-theta, said peaks being present at 6.3±0.2° 2θ and one or more of the following peaks 11.6±0.2° 2θ, 12.0±0.2° 2θ, 17.1±0.2° 2θ, and 21.0±0.2° 2θ.

One aspect of the present disclosure provides a solid state form of ivosidenib that is Form M having an x-ray powder diffraction pattern comprising one peak, or two peaks, or three peaks, or four peaks, or five peaks, or six peaks, or seven peaks, or eight peaks, or nine peaks, in terms of 2-theta, said peaks being present at 11.4±0.2° 2θ, 17.7±0.2° 2θ, 17.8±0.2° 2θ, 19.7±0.2° 2θ, and 21.4±0.2° 2θ.

One aspect of the present disclosure provides a solid state form of ivosidenib that is Form N having an x-ray powder diffraction pattern comprising one peak, or two peaks, or three peaks, or four peaks, or five peaks, or six peaks, or seven peaks, or eight peaks, or nine peaks, in terms of 2-theta, said peaks being present at 8.6±0.2° 2θ, 14.4±0.2° 2θ, 18.6±0.2° 2θ, 20.3±0.2° 2θ and 22.9±0.2° 2θ.

One aspect of the present disclosure provides a solid form of ivosidenib (Form M) having a differential scanning calorimetry thermogram comprising an endothermic peak at 170.0° C.

One aspect of the present disclosure provides a solid form of ivosidenib (Form M) having a differential scanning calorimetry thermogram comprising an endothermic peak at 170.5° C.

One aspect of the present disclosure provides a solid form of ivosidenib (Form N) having a differential scanning calorimetry thermogram comprising an endothermic peak at 214.8° C.

One aspect of the present disclosure provides a solid form of ivosidenib (Form N) having a differential scanning calorimetry thermogram comprising an endothermic peak at 215.4° C.

One aspect of the present disclosure provides a pharmaceutical composition comprising any solid state form of ivosidenib described herein, wherein the pharmaceutical composition comprises at least 1% by weight of the total sample of ivosidenib.

One aspect of the present disclosure provides a pharmaceutical composition comprising any solid state form of ivosidenib described herein, wherein the pharmaceutical composition comprises at least 2% by weight of the total sample of ivosidenib.

One aspect of the present disclosure provides a pharmaceutical composition comprising any solid state form of ivosidenib described herein, wherein the pharmaceutical composition comprises at least 3% by weight of the total sample of ivosidenib.

One aspect of the present disclosure provides a pharmaceutical composition comprising any solid state form of ivosidenib described herein, wherein the pharmaceutical composition comprises at least 4% by weight of the total sample of ivosidenib.

One aspect of the present disclosure provides a pharmaceutical composition comprising any solid state form of ivosidenib described herein, wherein the pharmaceutical composition comprises at least 5% by weight of the total sample of ivosidenib.

One aspect of the present disclosure provides a pharmaceutical composition comprising any solid state form of ivosidenib herein described, each individually in an anhydrous, hydrate or solvate thereof, and one or more pharmaceutically acceptable excipients.

In one aspect, the present disclosure provides a pharmaceutical composition including ivosidenib and a second molecule, the second molecule being selected from among 2-((2S)-2-((1-(2-chlorophenyl)-2-((3,3-difluorocyclobutyl)amino)-2-oxoethyl)(5-fluoropyridin-3-yl)carbamoyl)-5-oxopyrrolidin-1-yl)isonicotinamide; (S)—N—((S)-1-(2-chlorophenyl)-2-((3,3-difluorocyclobutyl)amino)-2-oxoethyl)-1-(4-cyanopyridin-2-yl)-5-oxo-N-(pyridin-3-yl)pyrrolidine-2-carboxamide; (S)—N—((R)-1-(2-Chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide; (R)—N—((S)-1-(2-Chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide; and (R)—N—((R)-1-(2-Chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide, wherein the second molecule is present at a quantity of not more than 0.15% area % or less as determined by HPLC analysis.

In another aspect, the present disclosure provides a pharmaceutical composition including ivosidenib and a second molecule, the second molecule being selected from among 3-amino-5-fluoropyridine, 2-chloro-4-cyanopyridine, (S)—N—((S)-1-(2-Chlorophenyl)-2-((3,3-difluorocyclobutyl)

amino)-2-oxoethyl)-N-(5-fluoropyridin-3-yl)-5-oxopyrrolidine-2-carboxamide, 2-(2-Chlorophenyl)-N-(3,3-difluorocyclobutyl)-2-((5-fluoropyridin-3-yl)amino)acetamide, (S)-5-(((S)-1-(2-Chlorophenyl)-2-((3,3-difluorocyclobutyl)amino)-2-oxoethyl)(5-fluoropyridin-3-yl)amino)-4-((4-cyanopyridin-2-yl)amino)-5-oxopentanoic acid, (S)-4-(bis(4-cyanopyridin-2-yl)amino)-5-(((S)-1-(2-chlorophenyl)-2-((3,3-difluorocyclobutyl)amino)-2-oxoethyl)(5-fluoropyridin-3-yl)amino)-5-oxopentanoic acid, (S)-2-(2-Chlorophenyl)-2-((54(4-cyanopyridin-2-yl) amino)-2-oxo-3,4-dihydro-2H-pyran-6-yl)(5-fluoropyridin-3-yl)amino)-N-(3,3-difluorocyclobutyl)acetamide, (2S)—N-((1S)-2-((2-chloro-3,3-difluorocyclobutyl)amino)-1-(2-chlorophenyl)-2-oxoethyl)-1-(4-cyanopyridin-2-yl)-N-(5-fluoropyridin-3-yl)-5-oxopyrrolidine-2-carboxamide, (S)-1-(4-Cyanopyridin-2-yl)-N—((S)-1-(2,4-dichlorophenyl)-2-((3,3-difluorocyclobutyl)amino)-2-oxoethyl)-N-(5-fluoropyridin-3-yl)-5-oxopyrrolidine-2-carboxamide, (S)-1-(4-Cyanopyridin-2-yl)-N—((S)-1-(2,3-dichlorophenyl)-2-((3,3-difluorocyclobutyl)amino)-2-oxoethyl)-N-(5-fluoropyridin-3-yl)-5-oxopyrrolidine-2-carboxamide, (S)—N—((S)-1-(4-Chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide, 3-((2S)-1-(4-carbamoylpyridin-2-yl)-N-(1-(2-chlorophenyl)-2-((3,3-difluorocyclobutyl)amino)-2-oxoethyl)-5-oxopyrrolidine-2-carboxamido)-5-fluoropyridine 1-oxide, and 4-carbamoyl-2-((2S)-2-((1-(2-chlorophenyl)-2-((3,3-difluorocyclobutyl)amino)-2-oxoethyl)(5-fluoropyridin-3-yl)carbamoyl)-5-oxopyrrolidin-1-yl)pyridine 1-oxide, wherein the second molecule is present at a quantity of 0.15% area % or less as determined by HPLC analysis.

In another aspect, the present disclosure provides a pharmaceutical composition including ivosidenib and a second molecule, the second molecule being selected from among benzaldehyde, benzyl chloride, 2-chlorobenzyl chloride, 1-chloro-2-(chloromethyl)benzene, 1-chloro-2-(dichloromethyl)benzene, phenol, and benzene, wherein the second molecule is present at a quantity of 2 ppm or less.

In another aspect, the present disclosure provides a pharmaceutical composition comprising ivosidenib and one or more pharmaceutically acceptable excipients, wherein the composition contains no more than trace palladium, molybdenum, cadmium, lead, arsenic, mercury, cobalt, vanadium, and nickel.

In another aspect, the present disclosure provides a pharmaceutical composition comprising ivosidenib and one or more pharmaceutically acceptable excipients, wherein the composition contains no more than each of: 5000 ppm of isopropyl acetate, 5000 ppm n-heptane, 600 ppm dichloromethane, and 2 ppm benzene.

In another aspect, the present disclosure provides a process for making ivosidenib comprising testing at one or more stage of the process for one or more of:
2-((2S)-2-((1-(2-chlorophenyl)-2-((3,3-difluorocyclobutyl) amino)-2-oxoethyl)(5-fluoropyridin-3-yl)carbamoyl)-5-oxopyrrolidin-1-yl)isonicotinamide; (S)—N—((S)-1-(2-chlorophenyl)-2-((3,3-difluorocyclobutyl)amino)-2-oxoethyl)-1-(4-cyanopyridin-2-yl)-5-oxo-N-(pyridin-3-yl)pyrrolidine-2-carboxamide; (S)—N—((R)-1-(2-Chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide; (R)—N—((S)-1-(2-Chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide; and (R)—N—((R)-1-(2-Chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide, or a salt, hydrate, or solvate thereof.

In another aspect, the present disclosure provides a process for making ivosidenib comprising testing at one or more stage of the process for one or more of:
3-amino-5-fluoropyridine;
2-chloro-4-cyanopyridine;
(S)—N—((S)-1-(2-Chlorophenyl)-2-((3,3-difluorocyclobutyl)amino)-2-oxoethyl)-N-(5-fluoropyridin-3-yl)-5-oxopyrrolidine-2-carboxamide;
2-(2-Chlorophenyl)-N-(3,3-difluorocyclobutyl)-2-((5-fluoropyridin-3-yl)amino)acetamide;
(S)-5-(((S)-1-(2-Chlorophenyl)-2-((3,3-difluorocyclobutyl) amino)-2-oxoethyl)(5-fluoropyridin-3-yl)amino)-4-((4-cyanopyridin-2-yl)amino)-5-oxopentanoic acid;
(S)-4-(bis(4-cyanopyridin-2-yl)amino)-5-(((S)-1-(2-chlorophenyl)-2-((3,3-difluorocyclobutyl)amino)-2-oxoethyl) (5-fluoropyridin-3-yl)amino)-5-oxopentanoic acid;
(S)-2-(2-Chlorophenyl)-2-((5-((4-cyanopyridin-2-yl) amino)-2-oxo-3,4-dihydro-2H-pyran-6-yl)(5-fluoropyridin-3-yl)amino)-N-(3,3-difluorocyclobutyl)acetamide;
(2S)—N-((1S)-2-((2-chloro-3,3-difluorocyclobutyl)amino)-1-(2-chlorophenyl)-2-oxoethyl)-1-(4-cyanopyridin-2-yl)-N-(5-fluoropyridin-3-yl)-5-oxopyrrolidine-2-carboxamide;
(S)-1-(4-Cyanopyridin-2-yl)-N—((S)-1-(2,4-dichlorophenyl)-2-((3,3-difluorocyclobutyl)amino)-2-oxoethyl)-N-(5-fluoropyridin-3-yl)-5-oxopyrrolidine-2-carboxamide;
(S)-1-(4-Cyanopyridin-2-yl)-N—((S)-1-(2,3-dichlorophenyl)-2-((3,3-difluorocyclobutyl)amino)-2-oxoethyl)-N-(5-fluoropyridin-3-yl)-5-oxopyrrolidine-2-carboxamide;
(S)—N—((S)-1-(4-Chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide;
3-((2S)-1-(4-carbamoylpyridin-2-yl)-N-(1-(2-chlorophenyl)-2-((3,3-difluorocyclobutyl)amino)-2-oxoethyl)-5-oxopyrrolidine-2-carboxamido)-5-fluoropyridine 1-oxide;
4-carbamoyl-2-((2S)-2-((1-(2-chlorophenyl)-2-((3,3-difluorocyclobutyl)amino)-2-oxoethyl)(5-fluoropyridin-3-yl) carbamoyl)-5-oxopyrrolidin-1-yl)pyridine 1-oxide; and
(S)-1-(4-Cyanopyridin-2-yl)-N—((S)-1-(3,3-difluorocyclobutyl)-2-oxoindolin-3-yl)-N-(5-fluoropyridin-3-yl)-5-oxopyrrolidine-2-carboxamide, or salts, hydrates, or solvates thereof.

In another aspect, the present disclosure provides a process for making ivosidenib comprising testing at one or more stage of the process for one or more of: benzaldehyde, benzyl chloride, 2-chlorobenzyl chloride, 1-chloro-2-(chloromethyl)benzene, 1-chloro-2-(dichloromethyl)benzene, phenol, benzene, palladium, and molybdenum.

One or more aspects and embodiments may be incorporated in a different embodiment although not specifically described. That is, all aspects and embodiments can be combined in any way or combination.

DETAILED DESCRIPTION

Figure 1:
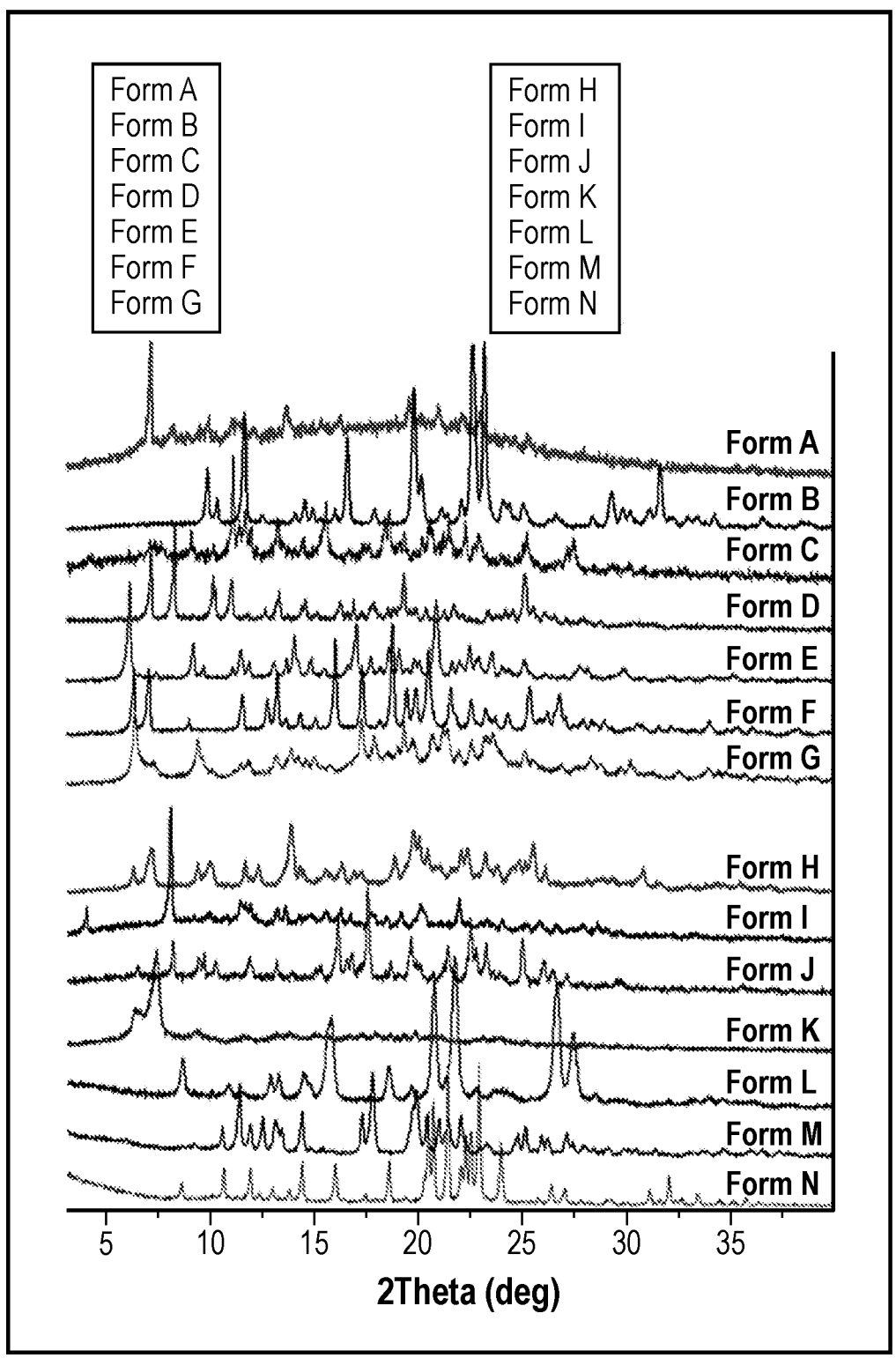
FIG. 1 is an X-ray powder diffraction (XRPD) overlay showing the characteristic peak readouts from conducting XRPD on a variety of polymorphs of ivosidenib.

The details of construction and the arrangement of components set forth in the following description or illustrated in the drawings are not meant to be limiting. Other embodiments and different ways to practice the invention are expressly included. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

Definitions

As used above, and throughout the description of different aspects of the disclosure, the following terms, unless otherwise indicated, shall be understood to have the following meanings.

As used herein, "solid state form" refers to one of Form L, Form B, Form A, Form C, Form D, Form E, Form F, Form G, Form H, Form I, Form J, Form K, Form M, or Form N of ivosidenib as characterized herein. The term "form" when used without a modifier refers to a solid state form. The term solid state form encompasses anhydrous, hydrated, and solvated forms, unless expressly stated otherwise. Solid state form is a general term that refers to both crystalline and amorphous material. Crystalline forms can include polymorphs, hydrates, solvates, salts, and cocrystals.

As used herein, "crystalline" refers to a solid having a highly regular chemical structure. In particular, a crystalline free base or salt form may be produced as one or more single crystalline forms. For the purposes of this application, the terms "crystalline form", "single crystalline form" and "polymorph" are synonymous; the terms distinguish between crystals that have different properties (e.g., different XRPD patterns and/or different DSC scan results). The term "polymorph" includes pseudopolymorphs, which are typically different solvates of a material, and thus their properties differ from one another. Thus, each distinct polymorph and pseudopolymorph of a free base or salt form is considered to be a distinct single crystalline form herein.

The term "substantially crystalline" refers to forms that may be at least a particular weight percent crystalline. Particular weight percentages are 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 100%. In some embodiments, substantially crystalline refers a solid state form of a compound of Formula I that is at least 70% crystalline. In other embodiments, substantially crystalline refers to a free base or salt form that is at least 90% crystalline. In some embodiments, a form of a compound of formula I that is less than about 90% crystalline may be referred to as being "partially crystalline" to distinguish from "substantially crystalline". In other embodiments, a partially crystalline form of a compound of formula I may be anywhere between about 5%-90% crystalline.

"Form L" or "ivosidenib Form L" may be used interchangeably, and describe the crystalline form synthesized in Example 2, in the Examples section below, and as described below, and represented by data shown in FIGS. 1, 2, and 3.

"Form B" or "ivosidenib Form B" are used interchangeably, and describe the crystalline form synthesized in Example 3, in the Examples section below, and as described below, and represented by data shown in FIGS. 4, 5, and 6.

As used herein, "amorphous" refers to a solid material having no long range order in the position of its atoms. Amorphous solids are generally isotropic, i.e., exhibit similar properties in all directions and do not have definite melting points. For example, an amorphous material is a solid material having no sharp characteristic crystalline peak(s) in its X-ray powder diffraction (XRPD) pattern (i.e., is not crystalline as determined by XRPD). Instead, one or several broad peaks (e.g., halos) appear in its XRPD pattern. Broad peaks are characteristic of an amorphous solid. An amorphous preparation of a compound described herein is substantially free of any crystalline forms of the same compound. The term "amorphous form" refers to a solid form which is amorphous.

The term "substantially free" refers to forms and compositions that may be at least a particular weight percent free of impurities or is free of other crystalline forms of the same compound. Particular weight percentages that indicate that a particular form is substantially free of other crystalline forms of the same compound occurs if that particular form is present at about 60%, 70%, 75%, 80%, 85%, 87%, 88%, 89%, 90%, 91%, 92%, 93%, 94%, 95%, 96%, 97%, 98%, 99%, 99.5%, or at about 99.9% weight percent. In other embodiments a particular form is substantially free of other crystalline forms of the same compound if the particular form is present in an amount between about 60% and 100% free (w/w), which may be expressed as the particular crystalline form being between about 60% to 100% phase pure. The phrase "phase purity" refers to the degree to which a material is uncontaminated or unmixed with other crystalline forms of the same material. In some embodiments, substantially free refers to a crystalline form of a compound of Formula (I) that is at least 70% phase pure. In other embodiments, substantially crystalline refers to a crystalline form of a compound of Formula I that is at least 90% phase pure. In other embodiments, substantially free of other crystalline forms refers to a crystalline form of a compound of Formula I, or a composition comprising the same, having less than about 30%, less than about 20%, less than about 15%, less than about 10%, less than about 5%, less than about 1% of another crystalline form of a compound of Formula I.

As used herein, the term "chemical purity" refers to the degree to which a compound of Formula I is uncontaminated or unmixed with extraneous materials, i.e., materials that are not a compound of Formula I. In various embodiments described herein, it should be understood that when compositions are described as containing one or more other compounds present in a particular amount or percentage, such as, for example "not more than x percent by weight" or "not more than x percent as measured by HPLC", that such expressions are a description of chemical purity. In some instances these other compounds are expressly identified as impurities.

As used herein, the terms "isolated" refers to forms that may be at least a particular weight percent of a particular crystalline form of a compound. Particular weight percentages are 90%, 91%, 92%, 93%, 94%, 95%, 96%, 97%, 98%, 99%, 99.5%, 99.9%, or any percentage between 90% and 100%.

The term "solvate or solvated" means a physical association of a compound, including a crystalline form thereof, of this invention with one or more solvent molecules. This physical association includes hydrogen bonding in a crystal lattice as well as adventitious (or loosely associated on the surface) solvent molecules. The term includes solvent molecules in stoichiometric and non-stoichiometric amounts. In certain instances the solvate form of a compound of Formula I will be capable of isolation, for example when one or more solvent molecules are incorporated in the crystal lattice of the crystalline solid. Solvates of the present disclosure include, for example, hydrates, ethanolates or methanolates. Non-limiting examples of the present disclosure include isopropanol, acetonitrile, isopropyl acetate, and methyl isobutyl ketone solvates. The terms "solvate" and "solvated form" are used interchangeably throughout this disclosure.

The term "hydrate" is a solvate wherein the solvent molecule is $H_2O$ that is present in a defined stoichiometric or non-stoichiometric amount. Stoichiometric solvates may, for example, include hemihydrate, monohydrate, dihydrate, or trihydrate forms, among others. Non-stoichiometric solvates may include, for example, channel hydrates, including where water content may change depending on humidity of the environment. The terms "hydrate" and "hydrated form" are used interchangeably throughout this disclosure.

The term "mixture" is used to refer to two or more elements or forms in intimate association regardless of the phase-state of the combination (e.g., liquid or liquid/crystalline).

The term "seeding" is used to refer to the addition of a crystalline material to initiate recrystallization or crystallization.

The term "antisolvent" is used to refer to a solvent in which compounds, including crystalline forms thereof, are poorly soluble.

As used herein, the term "about" means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

As used herein, the term "elevated levels of 2HG" means 10%, 20% 30%, 50%, 75%, 100%, 200%, 500% or more 2HG than is present in a subject that does not carry a mutant IDH1 allele. The term "elevated levels of 2HG" may refer to the amount of 2HG within a cell, within a tumor, within an organ comprising a tumor, or within a bodily fluid.

The term "bodily fluid" includes one or more of amniotic fluid surrounding a fetus, aqueous humour, blood (e.g., blood plasma), serum, Cerebrospinal fluid, cerumen, chyme, Cowper's fluid, female ejaculate, interstitial fluid, lymph, breast milk, mucus (e.g., nasal drainage or phlegm), pleural fluid, pus, saliva, sebum, semen, serum, sweat, tears, urine, vaginal secretion, or vomit.

As used herein, the terms "inhibit" or "prevent" include both complete and partial inhibition and prevention. An inhibitor may completely or partially inhibit the intended target.

The term "treat" means decrease, suppress, attenuate, diminish, arrest, or stabilize the development or progression of a disease/disorder (i.e., an advanced solid tumor, such as glioma, intrahepatic cholangiocarcinomas (IHCC), chondrosarcoma, prostate cancer, colon cancer, melanoma, or non-small cell lung cancer (NSCLC), each characterized by the presence of a mutant allele of IDH1), lessen the severity of the disease/disorder (i.e., an advanced solid tumor, such as glioma, intrahepatic cholangiocarcinomas (IHCC), chondrosarcoma, prostate cancer, colon cancer, melanoma, or non-small cell lung cancer (NSCLC), each characterized by the presence of a mutant allele of IDH1) or improve the symptoms associated with the disease/disorder (i.e., an advanced solid tumor, such as glioma, intrahepatic cholangiocarcinomas (IHCC), chondrosarcoma, prostate cancer, colon cancer, melanoma, or non-small cell lung cancer (NSCLC), each characterized by the presence of a mutant allele of IDH1.

As used herein, an amount of a compound effective to treat a disorder, or a "therapeutically effective amount" refers to an amount of the compound, which is effective, upon single or multiple dose administration to a subject, in treating a cell, or in curing, alleviating, relieving or improving a subject with a disorder beyond that expected in the absence of such treatment.

As used herein, "% w/w" is used to mean by weight as a percentage of a total weight that is used as the basis for calculating the weight percentage of an individual component. By way of example, for a bulk composition, the % w/w of an individual component may be calculated as a percentage of the total weight of all of the components of the bulk composition. By way of another example, for a single oral dosage form, the % w/w of an individual component may be calculated as a percentage of the total weight of all of the components of the single oral dosage form. For example, when the single oral dosage form is a tablet, the total weight may be the total weight of all the components of the tablet.

As used herein, the term "subject" is intended to mean human. Exemplary human subjects include a human patient (referred to as a patient) having a disorder, e.g., a disorder described herein or a normal subject. The term "subject" includes a pediatric population, where the pediatric population has a disorder as herein described. In other embodiments the subject is an adult human.

The term "physically stable," as used herein, means that a particular free base or salt form does not change into one or more different physical forms (e.g., different solid forms as measured by XRPD, DSC, etc.) when subjected to specified conditions, e.g., room temperature ambient humidity or 40° C./75% relative humidity, for a specified period of time, e.g., 1 day, 2 days, 3 days, 1 week, 2 weeks, 1 month, 2 months, 3 months, 6 months, 12 months, 18 months, 24 months, or longer. In some embodiments, less than 25% of the form of a compound changes into one or more different physical forms when subjected to specified conditions. In some embodiments, less than about 20%, less than about 15%, less than about 10%, less than about 5%, less than about 3%, less than about 1%, less than about 0.5% of the form of a particular compound changes into one or more different physical forms of that particular compound when subjected to specified conditions. In some embodiments, no detectable amount of the particular form of a compound changes into one or more different physical forms of the compound.

The term "chemically stable," as used herein, means that the chemical structure of a particular compound, does not change into another compound (e.g., decompose) when subjected to specified conditions, e.g., room temperature ambient humidity or 40° C./75% relative humidity, for a specified period of time, e.g., 1 day, 2 days, 3 days, 1 week, 2 weeks, 1 month, 2 months, 3 months, 6 months, 12 months, 18 months, 24 months, or longer. In some embodiments, less than 25% of the form of a particular compound changes into one or more other compounds when subjected to specified conditions. In some embodiments, less than about 20%, less than about 15%, less than about 10%, less than about 5%, less than about 3%, less than about 1%, less than about 0.5% of the form of a particular compound changes into one or more other compounds when subjected to specified conditions. In some embodiments, no detectable amount of the form of a particular compound changes into one or more different physical forms of that particular compound.

The term "dispersion" refers to a disperse system in which one substance, the dispersed phase, is distributed, in discrete units, throughout a second substance (the continuous phase or vehicle). The size of the dispersed phase can vary considerably (e.g., colloidal particles of nanometer dimension, to multiple microns in size). In general, the dispersed phases can be solids, liquids, or gases. In the case of a solid dispersion, the dispersed and continuous phases are both solids. In pharmaceutical applications, a solid dispersion can include a crystalline therapeutically active compound (dispersed phase) in an amorphous polymer(s) (continuous phase), or alternatively, an amorphous therapeutically active compound (dispersed phase) in an amorphous polymer (continuous phase).

The term "amorphous solid dispersion" generally refers to a solid dispersion of two or more components, usually a therapeutically active compound and polymer (or plurality of polymers), but possibly containing other components such as surfactants or other pharmaceutical excipients, where the therapeutically active compound is in the amorphous phase, and the physical stability and/or dissolution and/or solubility of the amorphous therapeutically active compound is enhanced by the other components. In some embodiments, an amorphous solid dispersion includes the polymer(s) (and optionally a surfactant) constituting the dispersed phase, and the therapeutically active compound constitutes the continuous phase. In some embodiments, an amorphous solid dispersion includes the polymer(s) (and optionally a surfactant) constituting the continuous phase, and the therapeutically active compound constitutes the dispersed phase.

An exemplary solid dispersion is a co-precipitate or a co-melt of a particular therapeutically active compound with one or more polymer(s). A "co-precipitate" is produced after dissolving a therapeutically active compound and one or more polymer(s) in a solvent or solvent mixture followed by the removal of the solvent or solvent mixture. Sometimes the one or more polymer(s) can be suspended in the solvent or solvent mixture. The solvent or solvent mixture includes organic solvents and supercritical fluids. The solvent or solvent mixture can also contain a non-volatile solvent. A "co-melt" is produced after heating a therapeutically active compound and one or more polymer(s) to melt, optionally in the presence of a solvent or solvent mixture, followed by mixing, removal of at least a portion of the solvent if applicable, and cooling to room temperature at a selected rate. In some cases, solid dispersions are prepared by adding a solution of a therapeutically active compound and solid polymers followed by mixing and removal of the solvent or solvent mixture. To remove the solvent or solvent mixture, vacuum drying, spray drying, tray drying, lyophilization, and other drying procedures may be applied. Applying any of these methods using appropriate processing parameters, according to this disclosure, would provide the particular therapeutically active compound in an amorphous state in the final solid dispersion product.

As used herein, the term "directly compressed dosage form" generally refers to a form (e.g., a tablet) that is obtained by the compression of a dry blend of powders (e.g., solid dispersion or agglomerated dispersion) that comprise a compound, namely a therapeutic compound (e.g., a poorly soluble therapeutic compound, ivosidenib, amorphous ivosidenib) in a solid dispersion, for example, that also includes one or more polymer(s) and optionally one or more surfactant(s)) and optionally one or more excipients. For example, the product (e.g., solid dispersion) resulting from a process described herein can have improved properties (e.g., flowability) that allow it to be directly compressed, e.g., into an oral dosage form, e.g., tablets, or to be formulated into capsules or sachets.

Pharmaceutical Compositions and Methods of Treatment

Provided is a method of treating advanced solid tumors, such as glioma, intrahepatic cholangiocarcinomas (IHCC), chondrosarcoma, prostate cancer, colon cancer, melanoma, or non-small cell lung cancer (NSCLC), each characterized by the presence of a mutant allele of IDH1 comprising administering to a subject in need thereof a pharmaceutical composition comprising: (a) a compound (S)—N—((S)-1-(2-chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide (ivosidenib), or a pharmaceutically acceptable salt thereof, as part of a solid dispersion, and optionally (b) one or more pharmaceutically acceptable carrier(s).

Also provided are compositions containing ivosidenib, or a pharmaceutically acceptable salt thereof, as part of a solid dispersion (e.g., an amorphous solid dispersion). Also provided are pharmaceutical compositions, comprising: (a) ivosidenib, or a pharmaceutically acceptable salt thereof, as part of a solid dispersion, and (b) one or more pharmaceutically acceptable carrier(s).

These methods of treatment and pharmaceutical compositions are further illustrated by the detailed descriptions and illustrative examples given below.

Pharmaceutical compositions comprising solid dispersions of a therapeutically active compound in a matrix can provide improved chemical and physical properties and can be prepared by forming a homogeneous solution or melt of the therapeutically active compound and matrix material followed by solidifying the mixture by cooling, or removal of the solvent. Such solid dispersions of therapeutically active compounds often show enhanced bioavailability when administered orally relative to oral compositions comprising the undispersed compound.

Spray drying is the most widely used industrial process involving particle formation and drying, and can be used to produce solid dispersions of therapeutically active compounds. It is highly suited for the continuous production of dry solids in either powder, granulate or agglomerate form from liquid feedstocks as solutions, emulsions and pumpable suspensions. Therefore, spray drying is a useful process where the end-product must comply with precise quality standards regarding particle size distribution, residual moisture content, bulk density, and particle shape.

Critical quality attributes of a spray-dried dispersion include potency, related substances, residual solvent content, homogeneity, lack of crystallinity, dissolution performance, particle morphology, and bulk powder flow properties.

Process parameters include spray solution composition and viscosity, nozzle type and dimensions, atomization pressure, spray solution feed rate, drying gas flow rate, inlet and outlet temperatures, condenser temperature (e.g., for closed-loop drying processes), and secondary drying parameters.

In one embodiment, at least a particular percentage by weight of ivosidenib is crystalline. Particular weight percentages may be 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 100%. When a particular percentage by weight of ivosidenib is crystalline, the remainder of ivosidenib is the amorphous form of ivosidenib. In some embodiments the particular percentage by weight of ivosidenib may comprise one crystalline form of ivosidenib or a mixture of two or more crystalline forms of ivosidenib. In some embodiments, ivosidenib is at least 90% by weight crystalline. In some other embodiments, ivosidenib is at least 95% by weight crystalline. In some other embodiments, ivosidenib is at least 99% by weight crystalline.

In another embodiment, a particular percentage by weight of the ivosidenib is a specific single form or a combination of forms. Particular weight percentages may be about 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 100%. In another embodiment, ivosidenib is at least 90% by weight of a single form. In another embodiment, ivosidenib is at least 95% by weight of a single form. In another embodiment, ivosidenib is at least 99% by weight of a single form.

In the following description of ivosidenib, embodiments of the disclosure may be described with reference to a particular form of ivosidenib, as characterized by one or more properties as discussed herein. The descriptions characterizing the forms may also be used to describe the mixture of different forms that may be present in an ivosidenib drug product. However, the particular forms of ivosidenib may also be characterized by one or more of the characteristics of the form as disclosed herein, with or without regard to referencing a particular form itself.

The forms are further illustrated by the detailed descriptions and illustrative examples given below. The XRPD peaks described in Tables pertaining to each form may vary by ±0.2 depending upon the instrument used to obtain the data.

Forms of Ivosidenib

At least 15 different polymorphs of ivosidenib have been identified and characterized. A polymorph screening was performed by generating solid ivosidenib under a variety of conditions and characterizing the samples obtained. Multiple crystalline forms of ivosidenib have been identified through solution evaporation, slurry, recrystallization, and solvent/anti-solvent precipitation experiments as listed in Table 1.

TABLE 1

Summary of polymorphs of AG-120 (freebase)

| Form | Identity | Melting point (DSC, °C.) | Weight loss (TGA, %) |
| --- | --- | --- | --- |
| Form A | Anhydrate/Hydrate | 67 | 1.6 |
| Form B | Channel hydrate | 154 | 2.0 |
| Form C | Isopropanol solvate | 65, 117, 142 | 8.3 |
| Form D | Acetonitrile solvate | 108 | 8.1 |
| Form E | Isopropyl acetate solvate | 93 | 9.5 |
| Form F | Solvate/Hydrate | 108 | 11.5 |
| Form G | Solvate/Hydrate | 58, 120, 145 | 5.1 |
| Form H | Solvate/Hydrate | 96, 163 | 3.7 |
| Form I | Anhydrate/Solvate | 97, 139 | 1.1 |
| Form J | Solvate/Hydrate | 81 | 15.5 |
| Form K | Unknown | N/A | N/A |
| Form L | Anhydrate | 150 | 0.5 |
| Form M | Anhydrate | 170 | <1% |
| Form N | Anhydrate | 214 | <1% |
| Pattern 3 | Solvate | | |

The forms were characterized by x-ray powder diffraction (XRPD), which are overlaid together in FIG. 1. The forms were further characterized by differential scanning calorimetry (DSC), and by thermogravimetric analysis (TGA).

Figure 2:
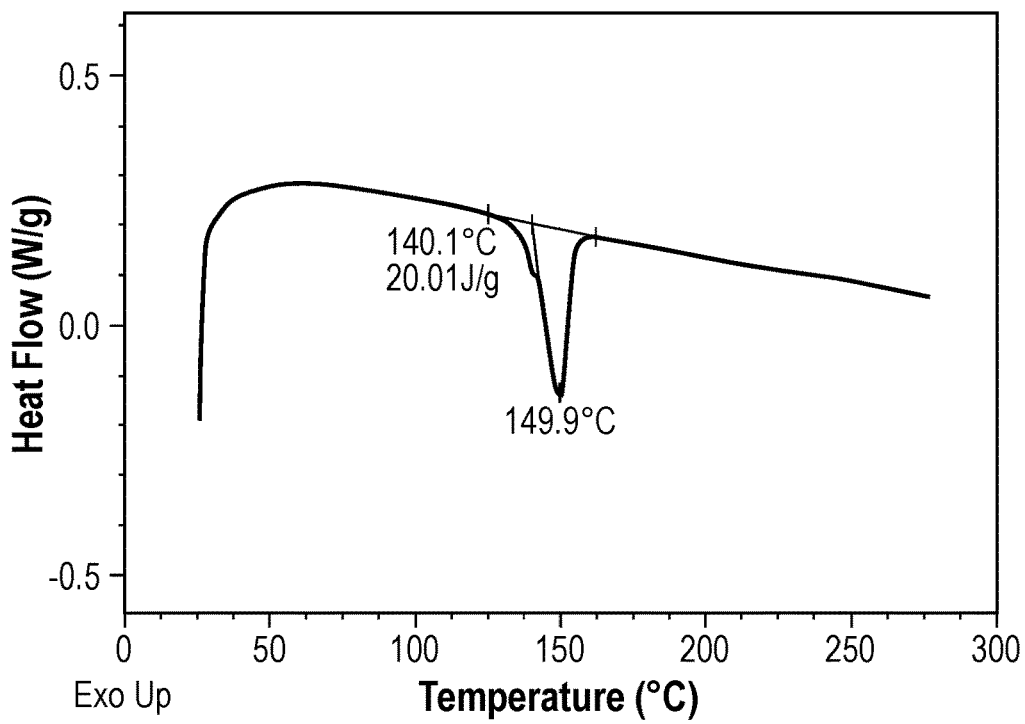
FIG. 2 is a differential scanning calorimetry (DSC) profile of Form L of ivosidenib.

Certain of the polymorphs of ivosidenib as disclosed herein are interconvertible, as is shown in FIG. 2. For instance, the anhydrate Form L can be converted to anhydrate Form N by treating with an isopropyl acetate (iPrOAc):heptane mixture, containing at most 25% iPrOAc at 70° C.

Form L

Form L is an anhydrous form of ivosidenib having a melting point as determined by differential scanning calorimetry (DSC) of 150 C, and a weight loss in thermogravimetric analysis (TGA) of 0.44%.

In one embodiment, to synthesize Form L of ivosidenib, a mixture of ivosidenib (3.5 kg, 7.28 mol) in 1,4-dioxane (35 L) is degassed by $N_2$ bubbling for a maximum of 20 min. 2-chloro-4-cyanopyridine (1.21 kg, 8.73 mol), tris(dibenzylideneacetone)-dipalladium(0) (167 g, 0.18 mol), and 4,5-bis(diphenylphosphino)-9,9-dimethylxanthene (xantphos) (211 g, 0.36 mol) are added and the reaction mixture is degassed by $N_2$ bubbling for a maximum of 10 min. K2CO3 (1.21 kg, 8.73 mol) is added and the reaction mixture is degassed by $N_2$ bubbling for a maximum of 30 min. The reaction mixture is heated at 90-100° C. for 4 to 24 hours until the reaction is complete. The reaction mixture is then cooled to 15-25° C. and filtered through Celite and is washed with ethyl acetate, and the combined filtrate and wash are concentrated.

The 1,4-dioxane is removed, and the residual solid is dissolved in ethyl acetate (77.5 L). The ethyl acetate solution is washed successively with a 5% aqueous solution of NaHSO3, a 2% aqueous solution of EDTA disodium, and a 1% aqueous solution of EDTA disodium salt. The organic phase is treated with activated carbon at 55-65° C. for a maximum of 2 h, and is purified by silica gel chromatography. After chromatography, the resulting product is purified by two recrystallizations: first compound 1 is dissolved in ethyl acetate and heated to 60-70° C. and heptane is added. The reaction mixture is cooled to 15-25° C. and stirred for 1-3 h. The product is filtered and is dissolved in dichloromethane, then is filtered and is precipitated with heptane, is filtered and dried to produce Form L.

In one embodiment, a single crystalline form, Form L, of ivosidenib is characterized by the X-ray powder diffraction (XRPD) pattern shown in FIG. 1, and data shown in Table 2, obtained using CuKa radiation. In a particular embodiment, the polymorph can be characterized by one or more of the peaks taken from FIG. 1, and as shown in Table 2. For example, the polymorph can be characterized by one or two or three or four or five or six or seven or eight or nine of the peaks shown in Table 2.

TABLE 2

Peaks of Form L by XRPD

| Angle (2-Theta°) | Intensity (%) |
| --- | --- |
| 8.7 | 90.3 |
| 13.2 | 60.0 |
| 15.7 | 85.5 |
| 18.5 | 72.5 |
| 19.6 | 31.5 |
| 20.7 | 71.6 |
| 21.5 | 100.0 |
| 26.4 | 64.2 |
| 27.3 | 45.6 |

In another embodiment, Form L can be characterized by the peaks identified at 2θ angles of 8.7, 15.7, 18.5, 20.7, 21.5, and 26.4°. In another embodiment, Form L can be characterized by the peaks identified at 2θ angles of 8.7, 15.7, 18.5, and 21.5°.

Figure 3:
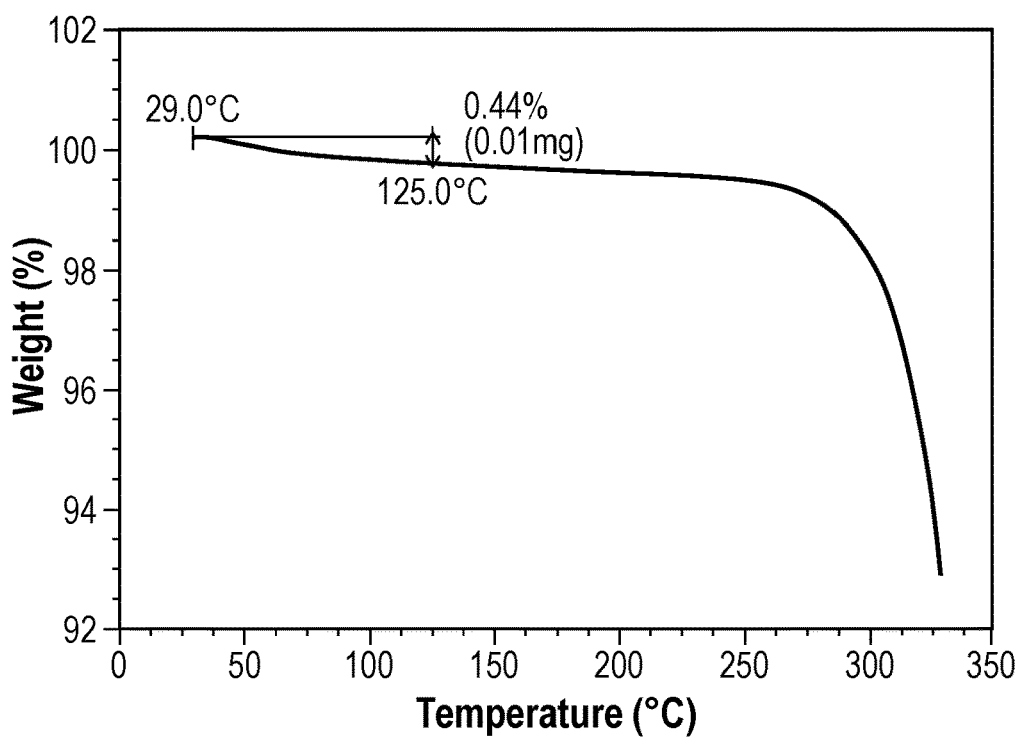
FIG. 3 is a thermogravimetric analysis (TGA) result of a study of Form L of ivosidenib.

In another embodiment, Form L can be characterized by the differential scanning calorimetry profile (DSC) shown in FIG. 3. The DSC graph plots the heat flow as a function of temperature from a sample, the temperature rate change being about 10° C./min. The profile is characterized by an endothermic transition with an onset temperature of about 140.1° C. with a melt at about 149.9° C.

Figure 4:
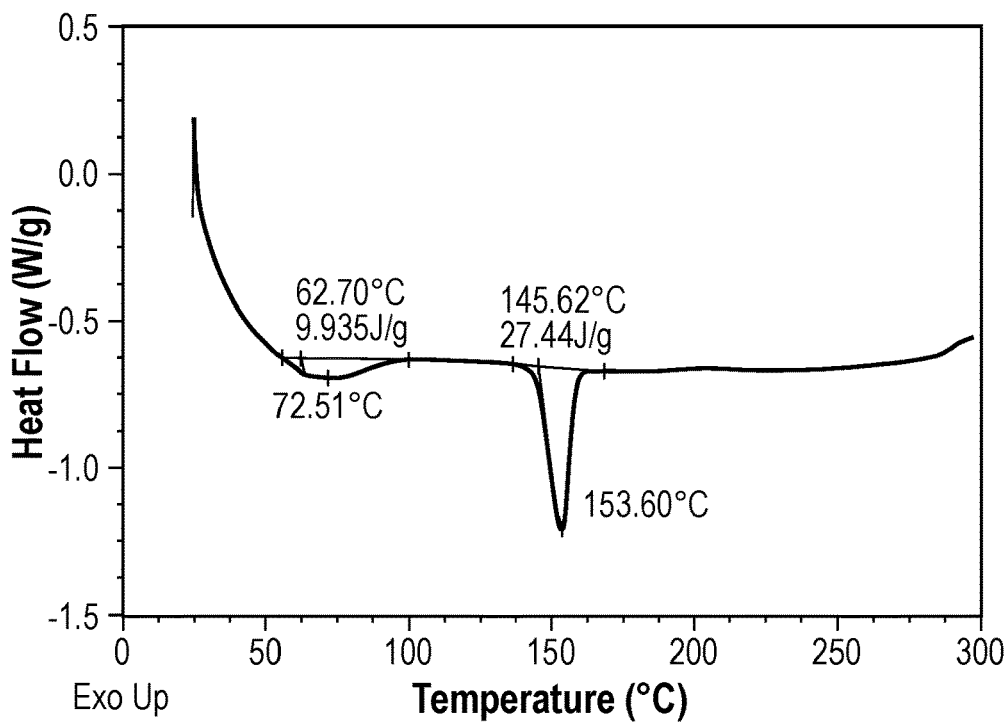
FIG. 4 is a DSC profile of Form B of ivosidenib.

In another embodiment, Form L can be characterized by thermal gravimetric analysis (TGA) shown in FIG. 4. The TGA profile graphs the percent loss of weight of the sample as a function of temperature, the temperature rate change being about 10° C./min. The weight loss represents a loss of about 0.44% of the weight of the sample as the temperature is changed from about 29.0° C. to 125.0° C.

Form B

Form B of ivosidenib is a channel hydrate form, which has a melting point by DSC of 154 C and a weight loss by TGA of 2.0%.

Form B may be synthesized in a number of ways. In a first method, about 100 mg of ivosidenib is mixed with 0.4 mL MeOH and stirred at room temperature for 12 h. The suspension is subsequently centrifuged, and the white solid is isolated.

In a second method, about 10 mg of ivosidenib is mixed in 0.2-0.4 mL of a mixture of MeOH:$H_2O$ (9:1) in a 3-mL glass vial. The resulting visually clear solution is covered with a cap and subjected to slow evaporation to induce precipitation. The solid is isolated.

In a third method, about 15 mg of compound 1 is dissolved in a mixture of EtOH:$H_2O$ (8:7 volume/volume) or Methyl ethyl ketone (MEK) at 50° C. and stirred at 50° C. for 30 min. Then the solution is cooled slowly to 5° C. at 0.1° C./min, and is stirred at 5° C. overnight. The solid is isolated.

In one embodiment, a single crystalline form, Form B, of the ivosidenib is characterized by the X-ray powder diffraction (XRPD) pattern shown in FIG. 1, and data shown in Table 3, obtained using CuKa radiation. In a particular embodiment, the polymorph can be characterized by one or more of the peaks taken from FIG. 1, as shown in Table 2. For example, the polymorph can be characterized by one or two or three or four or five or six or seven or eight or nine or ten of the peaks shown in Table 2.

TABLE 3

XRPD peaks associated with Form B of ivosidenib

| Angle (2-Theta°) | Intensity (%) |
| --- | --- |
| 9.9 | 85.6 |
| 10.4 | |
| 11.7 | 100.0 |
| 14.9 | 11.4 |
| 16.5 | 15.3 |
| 19.6 | 75.2 |
| 20.1 | 7.3 |
| 22.5 | 32.6 |
| 23.0 | 69.4 |
| 25.0 | 8.9 |
| 31.4 | 22.0 |

In another embodiment, Form B can be characterized by the peaks identified at 2θ angles of 9.9, 11.7, 19.6, 22.5, 23.0, and 31.4°. In another embodiment, Form B can be characterized by the peaks identified at 20 angles of 9.9, 11.7, 19.6, and 23.0°.

Figure 5:
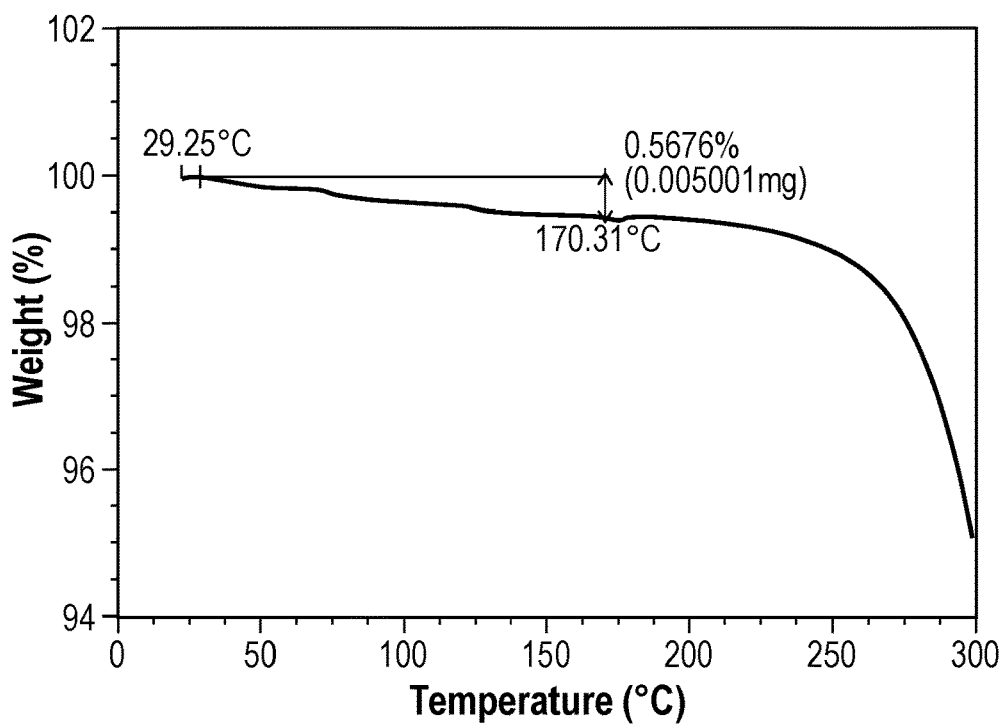
FIG. 5 is a TGA result of a study of Form B of ivosidenib.

In another embodiment, Form B can be characterized by the differential scanning calorimetry profile (DSC) shown in FIG. 5. The DSC graph plots the heat flow as a function of temperature from a sample, the temperature rate change being about 10° C./min. The profile is characterized by an endothermic transition with an onset temperature of about 62.7° C. with a melt at about 72.5° C., and an endothermic transition with an onset temperature of about 145.6° C. with a melt at about 153.6° C.

Figure 6:
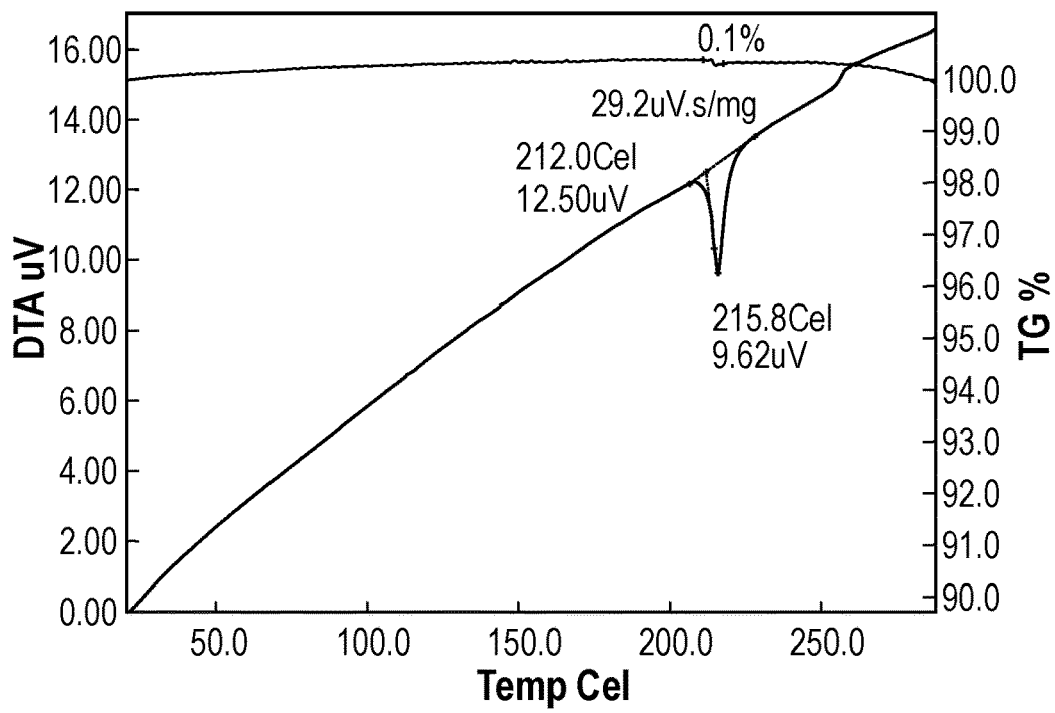
FIG. 6 is a TGA/differential thermal analysis (DTA) result of a study of Form N of ivosidenib.

In another embodiment, Form B can be characterized by thermal gravimetric analysis (TGA) shown in FIG. 6. The TGA profile graphs the percent loss of weight of the sample as a function of temperature, the temperature rate change being about 10° C./min. The weight loss represents a loss of about 0.57% of the weight of the sample as the temperature is changed from about 29.3° C. to 170.3° C.

Form M and Form N

Forms M and N of ivosidenib are anhydrous forms obtained at high heptane concentrations. Form N is obtained at a high heptane concentration of between 75-95% at 70° C., and Form M is obtained at very high heptane concentrations (95%) at 40° C.

To determine the most stable anhydrous form, competitive slurries using Form L, Form M, and Form N were carried out in dichloromethane, heptane, tBME and acetone. These experiments indicated that Form N was a stable anhydrous form under the conditions assessed, correlating with the thermal data obtained which indicated a significantly higher melting temperature of ca. 215° C. and melting enthalpy of ca. 53 mJ/mg for Form N compared with the melting temperature (ca. 170° C.) and enthalpy (ca. 33 mJ/mg) of Form M. To determine the likelihood of obtaining these forms during the crystallization, slurry conversion experiments were carried out, employing a crystallization procedure involving mixing 141.6 g of Form B ivosidenib and 432 mL iPrOAc in a 1 L vessel and stirring at 50° C. and 210 rpm. The temperature was increased to 70° C. to dissolve material. Anti-solvent addition (60 mL heptane) at 60 mL/h was carried out at 70° C. Once the anti-solvent addition was complete, the reaction was cooled to 60° C. and seeded with 0.63 g of Form B ivosidenib, which was stirred at 60° C. for 4 h then cooled to 15° C. over 10 h. An anti-solvent addition was started (308 mL heptane) at 75 mL/h, 15° C., 200 rpm. When the anti-solvent addition finished, the mixture was stirred at 15° C. for 2 h then isolated solid through filtration using a Buchner funnel (120 mm Ø) and washed with 246 mL of iPrOAc:heptane (1:1 v/v). In isopropyl acetate:heptane 5:95 v/v, Form N was retained, while in isopropyl acetate:heptane 20:80 v/v, a mixture of Form B and Form N was obtained.

The following procedure was followed for competitive slurry trials of the Form L, Form M, and Form N polymorphs: Approximately 50 or 75 mg of each different solid form was weighed out into 1.5 mL screw-cap vials. 75 mg of each form was used for experiments at elevated temperature; 50 mg of each form was used for experiments at ambient temperature, except for experiments in acetone which used 100 mg of each form.

Appropriate 50:50 wt/wt combinations prepared of Forms L, M, and N (see Table 4 for details).

Aliquots (100 μL or 25 μL) of appropriate solvent added as required to obtain a mobile slurry which was then stirred at either ambient (ca. 23° C.) or elevated (35 or 50° C.) temperature for ca. 21 or 68.5 h (see Table 4 for details). Solids were isolated by centrifugation and analyzed by XRPD. If a mixture of patterns was still present, the experiment was continued until a single form was obtained (see Table 4 for details of experiment times). An additional 1 mL of appropriate solvent added to experiments that were continued at elevated temperature.

TABLE 4

Experimental details for competitive slurries

| Solvent | Input material | Elevated temperature/° C. | Solvent volume/μL Elevated | Solvent volume/μL Ambient | Total stirring time/h Elevated | Total stirring time/h Ambient |
|---|---|---|---|---|---|---|
| DCM | Form L + Form N | 35 | 200 | 200 | 20.5 | 68.5 |
|  | Form L + Form M |  | 200 | 200 | 20.5 | 68.5 |
|  | Form N + Form M |  | 200 | 200 | 20.5 | 68.5 |
| Heptane | Form L + Form N | 50 | 1300 | 500 | 20.5 | 68.5 |
|  | Form L + Form M |  | 1300 | 500 | 20.5 | 68.5 |
|  | Form N + Form M |  | 1300 | 500 | 42.5 | 68.5 |
| tBME | Form L + Form N | 50 | 1100 | 500 | 20.5 | 68.5 |
|  | Form L + Form M |  | 900 | 500 | 42.5 | 114 |
|  | Form N + Form M |  | 1200 | 500 | 20.5 | 68.5 |
| Acetone | Form L + Form N | 50 | 100 | 175 | 20.5 | 68.5 |
|  | Form L + Form M |  | 100 | 125 | 20.5 | 68.5 |
|  | Form N + Form M |  | 100 | 175 | 20.5 | 68.5 |

Characterization of Form N

A sample of Form N was poorly soluble in 5:95 v/v iPrOAc:heptane and remained a thick slurry throughout the experiment. XRPD analysis of both the centrifuged sample (taken after 15 h at 70° C.) and the dried product was consistent with Form N and there was excellent agreement between the diffractograms of the scale-up material and the sample isolated from the solid form mapping experiments.

Figure 7:
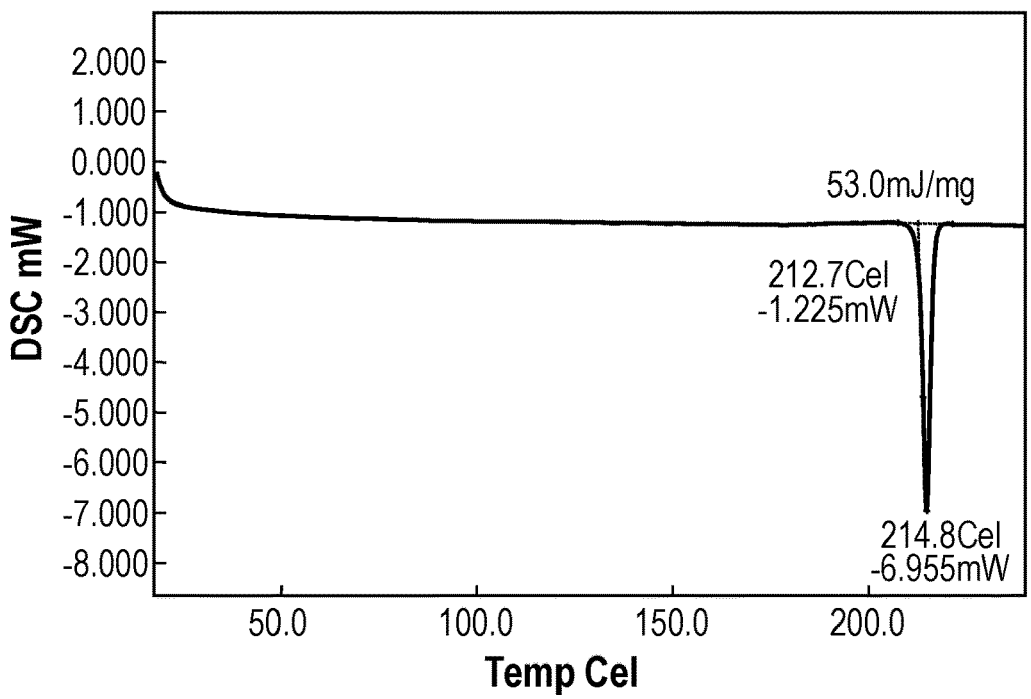
FIG. 7 is a DSC profile of Form N of ivosidenib.

Both the slurry and the dried material were birefringent by PLM analysis, with a needle-like morphology. TG analysis of the dried material showed essentially no weight loss, consistent with the Form N anhydrous form (see FIG. 7). DTA showed an endothermic event at onset ca. 212.0° C. (peak at ca. 215.8° C.), likely due to melting of the material as shown in FIG. 7.

Figure 8:
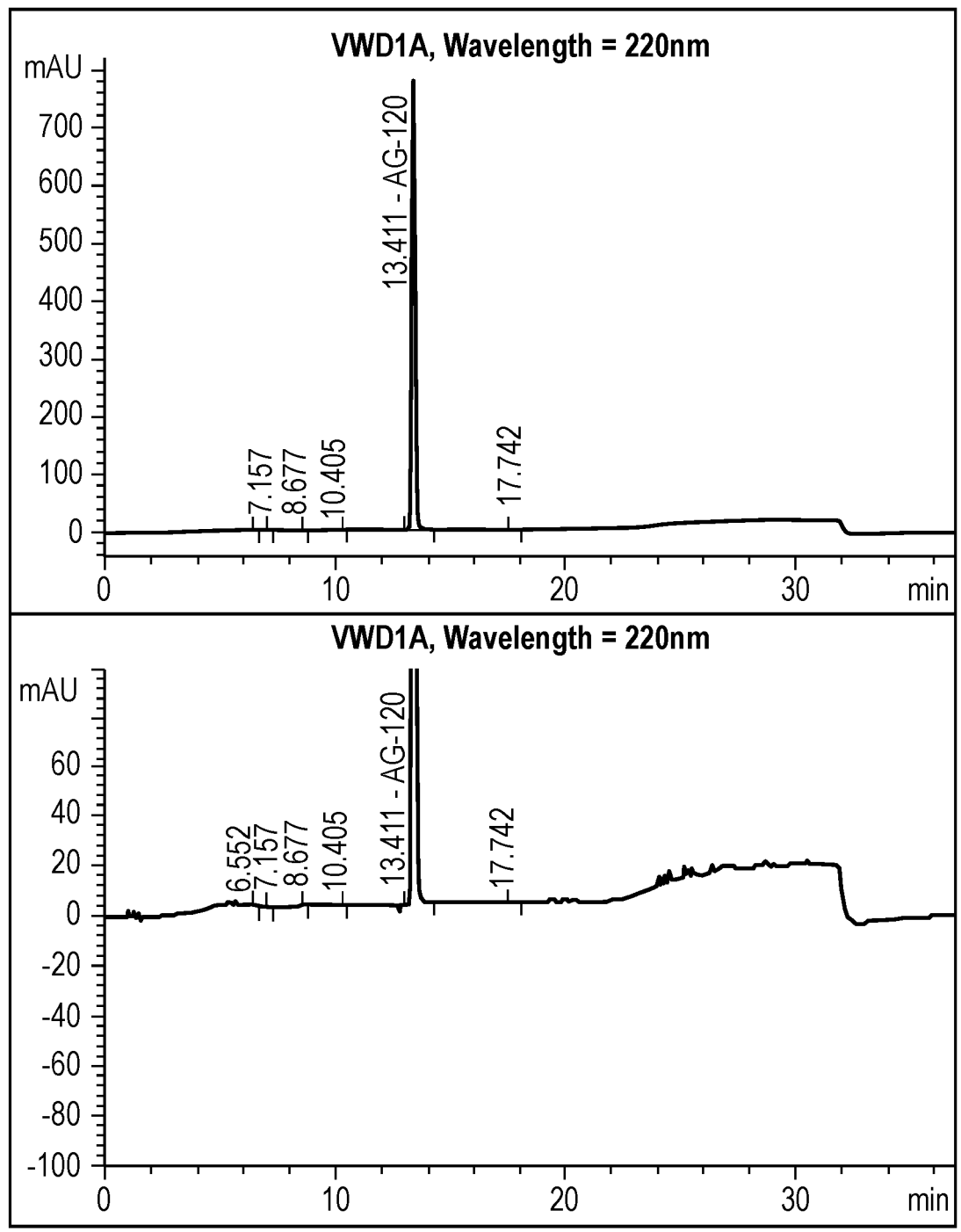
FIG. 8 is a HPLC profile of Form N of ivosidenib.

DSC analysis of the small sample removed after 15 h and dried for ca. 2 h under vacuum showed an endothermic event at onset ca. 212.7° C. (peak at ca. 214.8° C., enthalpy of 53.0 mJ/mg), likely due to melting of the material, as shown in FIG. 8. DSC analysis of the bulk dried material showed an endothermic event at onset ca. 212.6° C. (peak at ca. 215.4° C., enthalpy of 52.7 mJ/mg), likely due to melting of the material, as shown in FIG. 8.

Figure 9:
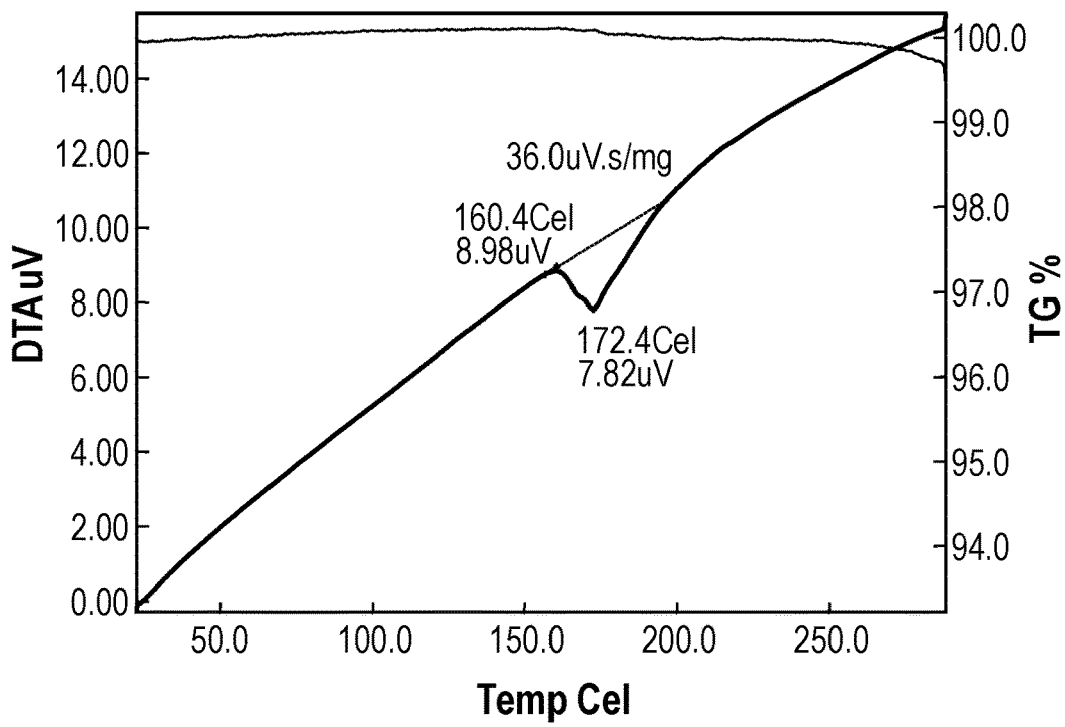
FIG. 9 is a TGA/DTA result of a study of Form M of ivosidenib.

HPLC analysis was carried out on the filtrate (<1 min filtration time, 80 mm diameter Buchner funnel, 101 mL mother liquor isolated), giving a mother liquor purity of 91.4%. The isolated yield was 4.66 g, 93%. The purity of the isolated solid was found to be 99.9% by HPLC analysis. See FIG. 9.

GC analysis of the material indicated that both iPrOAc and heptane content was <LOQ (LOQ solutions of iPrOAc (100 ppm) and heptane (200 ppm) run).

The solubility of Form N in methanol was found to be 113 mg/ml.

The peaks by XRPD of Form N of ivosidenib are defined as follows. Form N may be characterized by one or two or three or four or five or six or seven or eight or nine of the peaks shown in Table 5.

TABLE 5

XRPD Peaks of Form N of ivosidenib

| No. | Pos. [°2θ] | Area [cts*°2θ] | Backgr. [cts] | d-spacing [Å] | Height [cts] | Rel. Int. [%] |
|---|---|---|---|---|---|---|
| 1.00 | 3.3 | 31.92 | 593.65 | 26.71 | 39.53 | 1.06 |
| 2.00 | 6.2 | 9.12 | 346.97 | 14.30 | 120.42 | 3.24 |
| 3.00 | 8.6 | 328.22 | 278.29 | 10.23 | 3715.86 | 100.00 |
| 4.00 | 10.2 | 33.17 | 279.74 | 8.71 | 438.17 | 11.79 |
| 5.00 | 10.7 | 17.05 | 291.71 | 8.31 | 193.00 | 5.19 |
| 6.00 | 11.9 | 36.56 | 319.42 | 7.41 | 289.73 | 7.80 |
| 7.00 | 12.4 | 23.63 | 326.33 | 7.16 | 312.05 | 8.40 |
| 8.00 | 13.0 | 28.62 | 334.25 | 6.80 | 378.04 | 10.17 |
| 9.00 | 13.8 | 17.79 | 338.27 | 6.40 | 176.27 | 4.74 |
| 10.00 | 14.4 | 168.19 | 337.58 | 6.16 | 1332.90 | 35.87 |
| 11.00 | 16.0 | 177.16 | 326.12 | 5.54 | 1559.97 | 41.98 |
| 12.00 | 16.2 | 96.38 | 324.03 | 5.49 | 1091.15 | 29.36 |
| 13.00 | 16.4 | 63.71 | 319.60 | 5.39 | 631.08 | 16.98 |
| 14.00 | 17.5 | 52.69 | 298.92 | 5.08 | 521.92 | 14.05 |
| 15.00 | 18.0 | 13.05 | 288.87 | 4.93 | 86.18 | 2.32 |
| 16.00 | 18.6 | 152.23 | 280.50 | 4.77 | 1507.97 | 40.58 |
| 17.00 | 19.4 | 34.33 | 268.34 | 4.58 | 453.43 | 12.20 |
| 18.00 | 20.3 | 70.61 | 263.55 | 4.38 | 1119.13 | 30.12 |
| 19.00 | 20.7 | 55.90 | 263.98 | 4.28 | 442.98 | 11.92 |
| 20.00 | 21.4 | 87.71 | 262.91 | 4.15 | 992.94 | 26.72 |
| 21.00 | 22.0 | 32.54 | 261.10 | 4.03 | 322.38 | 8.68 |
| 22.00 | 22.3 | 77.83 | 259.58 | 3.99 | 616.80 | 16.60 |
| 23.00 | 22.5 | 44.21 | 256.87 | 3.95 | 583.95 | 15.71 |
| 24.00 | 22.9 | 183.99 | 251.40 | 3.89 | 1769.16 | 47.61 |
| 25.00 | 22.9 | 135.86 | 249.68 | 3.88 | 1538.09 | 41.39 |
| 26.00 | 23.2 | 23.98 | 243.80 | 3.83 | 190.00 | 5.11 |
| 27.00 | 24.0 | 84.35 | 225.02 | 3.71 | 835.59 | 22.49 |
| 28.00 | 25.4 | 10.00 | 214.59 | 3.51 | 66.04 | 1.78 |
| 29.00 | 25.8 | 9.25 | 215.38 | 3.45 | 61.11 | 1.64 |
| 30.00 | 26.3 | 100.46 | 215.59 | 3.38 | 568.67 | 15.30 |
| 31.00 | 27.0 | 108.77 | 211.47 | 3.30 | 430.98 | 11.60 |
| 32.00 | 27.4 | 46.59 | 205.17 | 3.25 | 263.71 | 7.10 |
| 33.00 | 28.2 | 15.21 | 188.64 | 3.17 | 100.45 | 2.70 |
| 34.00 | 29.2 | 146.14 | 171.85 | 3.06 | 482.55 | 12.99 |
| 35.00 | 29.9 | 28.13 | 163.65 | 2.99 | 139.30 | 3.75 |
| 36.00 | 31.1 | 47.09 | 161.44 | 2.88 | 207.34 | 5.58 |
| 37.00 | 32.1 | 21.83 | 164.72 | 2.79 | 216.20 | 5.82 |
| 38.00 | 32.6 | 31.48 | 164.74 | 2.75 | 249.48 | 6.71 |
| 39.00 | 33.5 | 30.06 | 167.90 | 2.68 | 170.18 | 4.58 |
| 40.00 | 34.0 | 19.88 | 175.52 | 2.64 | 98.49 | 2.65 |
| 41.00 | 34.4 | 28.21 | 181.73 | 2.61 | 139.72 | 3.76 |

Characterization of Form M

Form M material was poorly soluble in 5:95 v/v iPrOAc:heptane and remained a thick slurry throughout experiment. XRPD analysis of both the centrifuged sample (taken after 13 h at 40° C.) and the dried product was consistent with Pattern 5 and there was excellent agreement between the diffractograms of the scale-up material and the sample isolated from the solid form mapping experiments. (See FIG. 1.)

Both the slurry and the dried material were very slightly birefringent by PLM analysis, with no clearly defined morphology.

Figure 10:
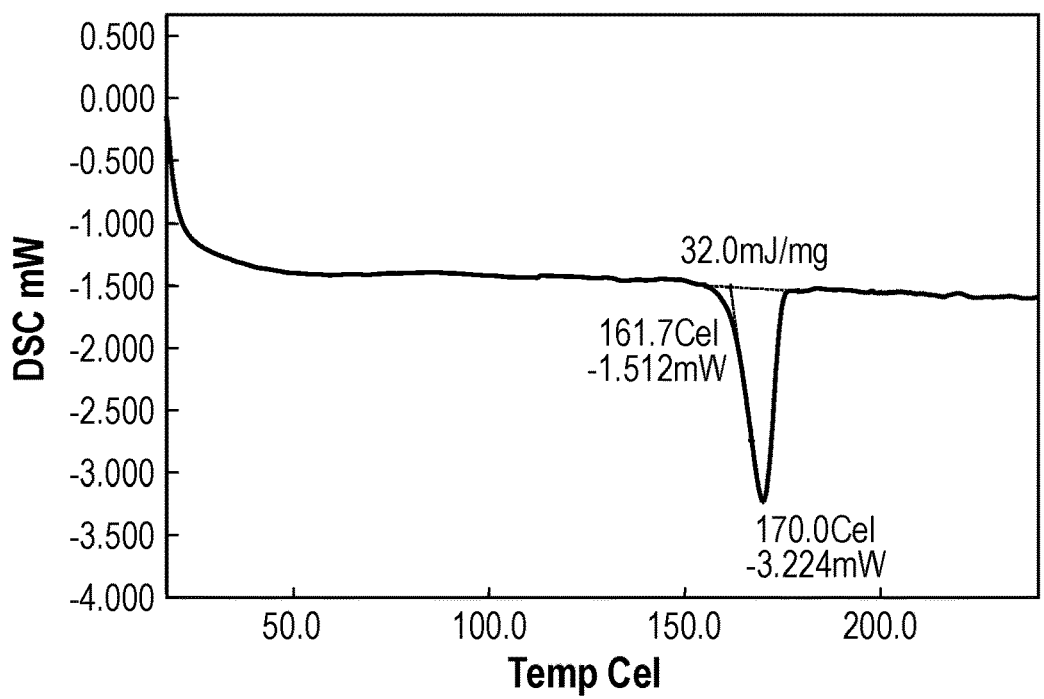
FIG. 10 is a DSC profile of Form M of ivosidenib.

TG analysis of the dried material showed essentially no weight loss, consistent with the Pattern 5 anhydrous form. (See FIG. 10.) DTA showed a broad endothermic event at onset ca. 160.4° C. (peak at ca. 172.4° C.), likely due to melting of the material, as can be seen in FIG. 10.

Figure 11:
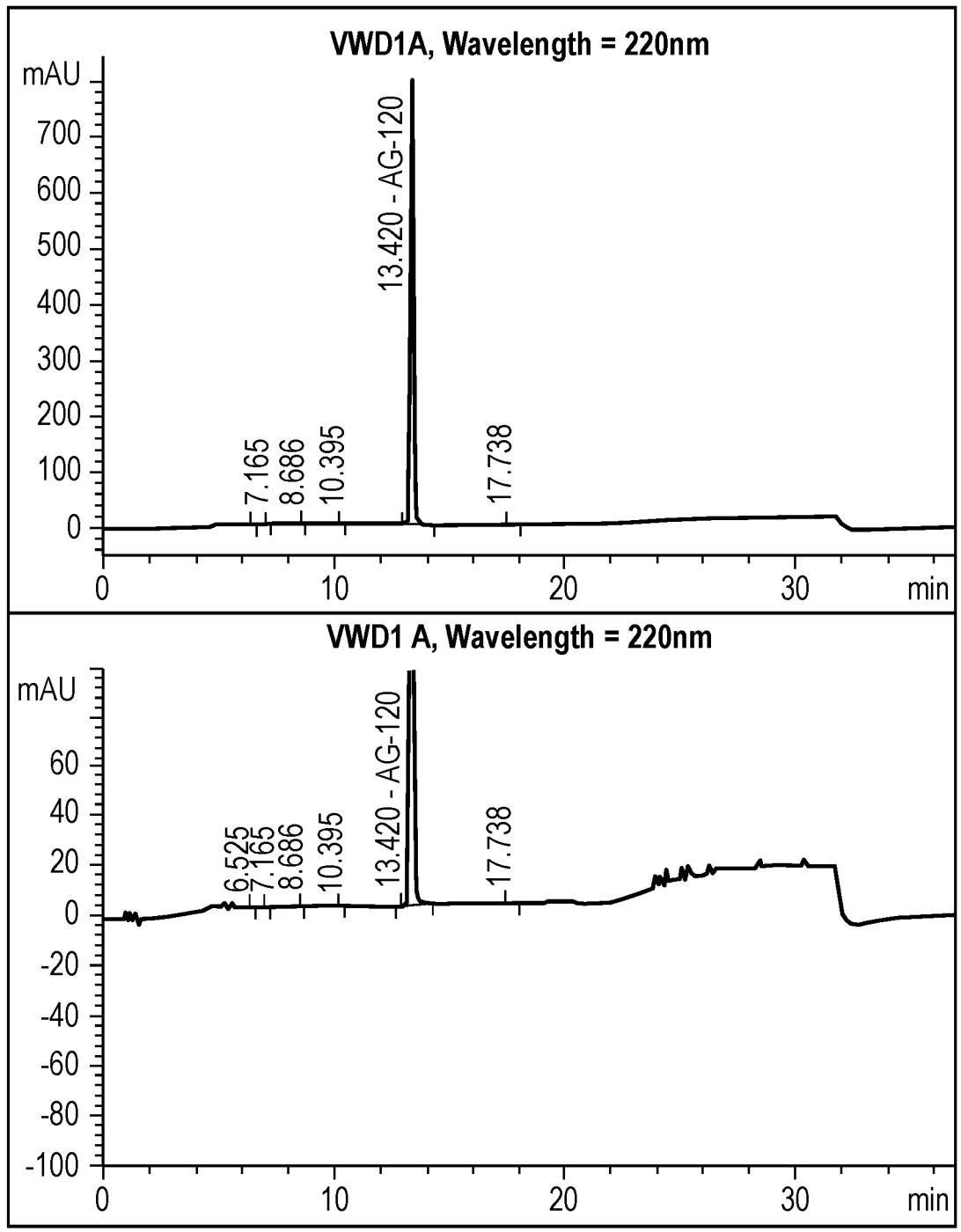
FIG. 11 is a HPLC profile of Form M of ivosidenib.

DSC analysis of the small sample removed after 13 h and dried for ca. 1.5 h under vacuum showed an endothermic event at onset ca. 161.7° C. (peak at ca. 170.0° C., enthalpy of 32.0 mJ/mg), likely due to melting of the material. DSC analysis of the bulk dried material showed an endothermic event at onset ca. 161.5° C. (peak at ca. 170.5° C., enthalpy of 33.9 mJ/mg), likely due to melting of the material, which is shown in FIG. 11.

Figure 12:
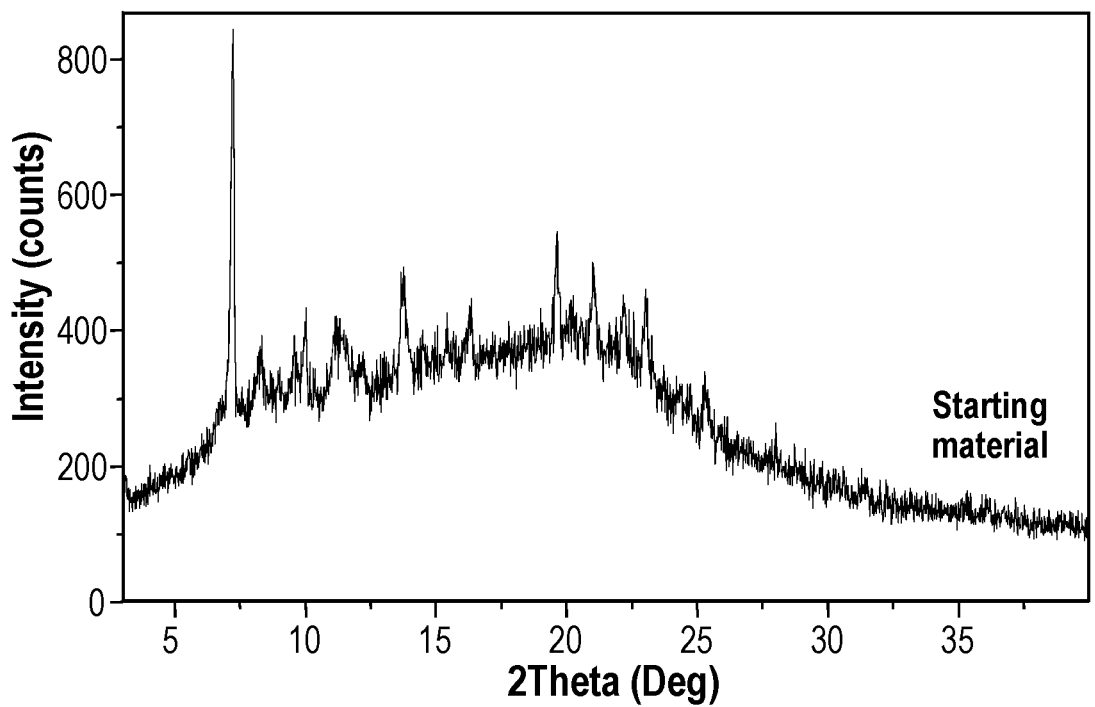
FIG. 12 is an XRPD diffractogram of Form A of ivosidenib.

HPLC analysis was carried out on the filtrate (<1 min filtration time, 80 mm diameter Buchner funnel, 110 mL mother liquor isolated), giving a mother liquor purity of 91.8%. The isolated yield was 4.63 g, 92%. The purity of the isolated solid was found to be 99.9% by HPLC analysis. (See FIG. 12.)

GC analysis of the Pattern 5 material indicated that the iPrOAc content was ca. 299 ppm, while the heptane content was ca. 339 ppm. (LOQ solutions of iPrOAc (100 ppm) and heptane (200 ppm) run).

The solubility of Form M in methanol was found to be 109 mg/ml.

The peaks by XRPD of Form M of ivosidenib are defined as follows. Form M may be characterized by one or two or three or four or five or six or seven or eight or nine of the peaks shown in Table 6.

TABLE 6

XRPD Peaks of Form M of ivosidenib

| No. | Pos. [°2θ] | Area [cts*°2θ] | Backgr. [cts] | d-spacing [Å] | Height [cts] | Rel. Int. [%] |
|---|---|---|---|---|---|---|
| 1.00 | 9.2 | 19.95 | 257.65 | 9.59 | 158.09 | 6.45 |
| 2.00 | 10.1 | 13.92 | 248.93 | 8.75 | 91.91 | 3.75 |
| 3.00 | 10.6 | 53.57 | 244.91 | 8.37 | 606.50 | 24.73 |
| 4.00 | 11.4 | 247.59 | 237.87 | 7.77 | 2452.62 | 100.00 |
| 5.00 | 11.9 | 34.22 | 233.65 | 7.45 | 271.21 | 11.06 |
| 6.00 | 12.5 | 60.49 | 228.30 | 7.09 | 684.83 | 27.92 |
| 7.00 | 13.1 | 77.19 | 223.33 | 6.78 | 1019.54 | 41.57 |
| 8.00 | 13.4 | 71.75 | 220.43 | 6.61 | 812.33 | 33.12 |
| 9.00 | 14.4 | 184.33 | 211.98 | 6.16 | 1460.74 | 59.56 |
| 10.00 | 15.3 | 11.46 | 205.63 | 5.77 | 90.81 | 3.70 |
| 11.00 | 15.8 | 9.60 | 204.08 | 5.61 | 63.40 | 2.58 |
| 12.00 | 17.2 | 37.55 | 199.54 | 5.14 | 595.09 | 24.26 |
| 13.00 | 17.7 | 101.15 | 198.29 | 5.01 | 1603.20 | 65.37 |
| 14.00 | 17.8 | 149.01 | 198.02 | 4.99 | 1476.07 | 60.18 |
| 15.00 | 18.5 | 8.65 | 195.95 | 4.80 | 57.13 | 2.33 |
| 16.00 | 19.5 | 66.46 | 192.92 | 4.56 | 752.35 | 30.68 |
| 17.00 | 19.7 | 130.54 | 192.29 | 4.52 | 1477.82 | 60.25 |
| 18.00 | 19.9 | 117.55 | 191.52 | 4.46 | 1164.47 | 47.48 |
| 19.00 | 20.4 | 95.23 | 189.93 | 4.36 | 943.37 | 38.46 |
| 20.00 | 20.9 | 153.35 | 187.92 | 4.25 | 1350.34 | 55.06 |
| 21.00 | 21.4 | 209.76 | 186.30 | 4.16 | 1662.33 | 67.78 |
| 22.00 | 22.0 | 209.40 | 184.00 | 4.05 | 1382.87 | 56.38 |
| 23.00 | 22.2 | 41.80 | 183.05 | 4.00 | 552.13 | 22.51 |
| 24.00 | 22.9 | 21.04 | 180.39 | 3.89 | 208.46 | 8.50 |
| 25.00 | 23.2 | 83.10 | 179.21 | 3.84 | 470.41 | 19.18 |
| 26.00 | 24.6 | 57.81 | 174.82 | 3.63 | 381.76 | 15.57 |
| 27.00 | 24.7 | 39.38 | 174.73 | 3.60 | 390.15 | 15.91 |
| 28.00 | 25.0 | 75.71 | 174.50 | 3.56 | 749.98 | 30.58 |
| 29.00 | 25.8 | 26.59 | 173.78 | 3.45 | 301.07 | 12.28 |
| 30.00 | 26.2 | 78.80 | 173.38 | 3.41 | 567.68 | 23.15 |
| 31.00 | 26.6 | 14.52 | 172.76 | 3.35 | 143.82 | 5.86 |
| 32.00 | 27.0 | 61.99 | 171.92 | 3.30 | 982.50 | 40.06 |
| 33.00 | 27.3 | 26.28 | 171.32 | 3.26 | 260.33 | 10.61 |
| 34.00 | 27.8 | 65.45 | 170.26 | 3.21 | 432.24 | 17.62 |
| 35.00 | 29.1 | 55.22 | 166.43 | 3.07 | 243.10 | 9.91 |
| 36.00 | 29.7 | 26.99 | 163.89 | 3.00 | 133.68 | 5.45 |
| 37.00 | 30.3 | 40.11 | 161.43 | 2.95 | 264.89 | 10.80 |
| 38.00 | 31.3 | 15.98 | 157.13 | 2.86 | 105.52 | 4.30 |
| 39.00 | 31.9 | 16.52 | 154.19 | 2.80 | 54.56 | 2.22 |
| 40.00 | 33.1 | 29.14 | 176.92 | 2.71 | 144.32 | 5.88 |
| 41.00 | 33.6 | 21.01 | 200.37 | 2.67 | 166.53 | 6.79 |
| 42.00 | 33.8 | 14.99 | 214.98 | 2.65 | 98.97 | 4.04 |
| 43.00 | 34.6 | 58.60 | 235.18 | 2.60 | 290.23 | 11.83 |

Form A

Figure 13:
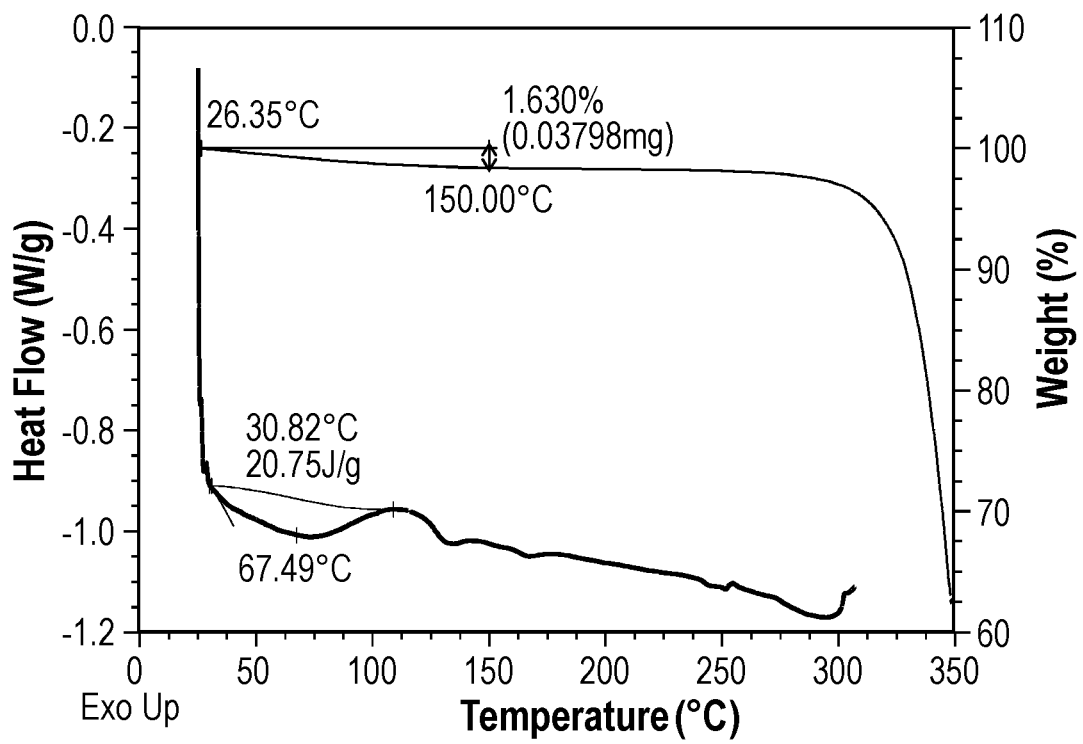
FIG. 13 is a combined plot of TGA and DSC analyses of Form A of ivosidenib.
Figure 14:
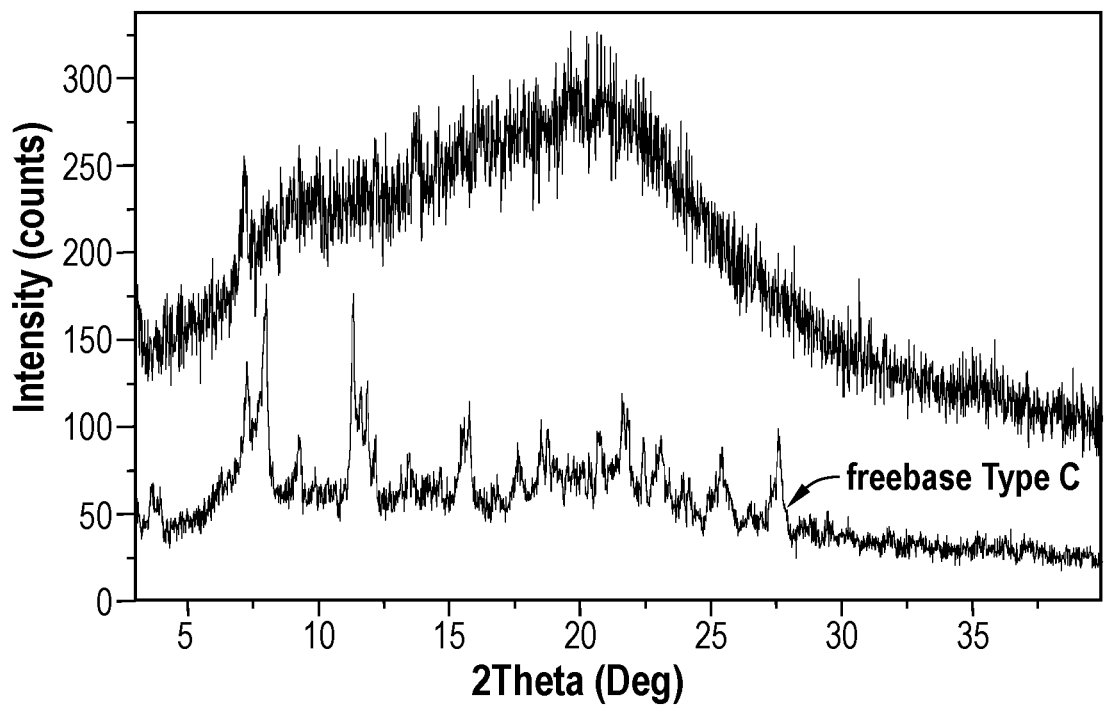
FIG. 14 is an XRPD diffractogram of Form C of ivosidenib.

From a sample of ivosidenib, which was partially crystalline as evidenced by the XRPD pattern shown in FIG. 13, the crystalline form was named as freebase Form A. DSC and TGA data are displayed in FIG. 14. The DSC curve exhibits an endothermic peak at 30.8° C. (onset). About 1.6% of weight loss was observed below ~150.0° C. in the TGA data shown in FIG. 14.

Screening to Discover Additional Polymorphs

Different crystallization or solid transition methods were applied to discover the various crystalline forms of freebase of ivosidenib, with part of experiments intended to identify a stable form. The methods utilized in the present study are summarized in Table 7, which include slow evaporation, slurry conversion at RT, anti-solvent addition and slow cooling (from 50° C. to 5° C.).

TABLE 7

Experiment types for polymorph screening

| Method | Number of Experiments | Crystalline Forms identified |
| --- | --- | --- |
| Slurry conversion at RT | 10 | freebase Form C, D, E, F, G, H, I |
| Anti-solvent addition | 8 | freebase Form B, K |
| Slow cooling (50° C.-5° C.) | 15 | freebase Form B, C, E, G, J |
| Slow evaporation | 15 | freebase Form B, C |

Approximate solubility of ivosidenib freebase was determined in 20 solvent systems at RT. In the experiment, ~2 mg of ivosidenib was added into a 3-mL glass vial, followed by the addition of corresponding solvent. The solvent was added by 100 μL step wise until the solution was visually clear or a total volume of 2 mL was reached. The results are listed in Table 8. This solubility information was used to select solvents for the polymorph screening.

TABLE 8

Solubility of ivosidenib

| Solvent | Solubility (mg/mL) |
| --- | --- |
| MeOH | >47.6 |
| EtOH | >39.4 |
| IPA | 38.8~19.4 |
| Acetic acid | 40.4~20.2 |
| ACN | >36.8 |
| Acetone | >36.4 |
| MIBK | 18.6~12.0 |
| EtOAc | >41.8 |
| IPAC | 40.2~20.1 |
| MTBE | >37.8 |
| THF | >39.0 |
| 2-MeTHF | >41.4 |
| 1,4-Dioxane | >41.6 |
| NMP | >42.0 |
| DMSO | 46.6~23.2 |
| $CHCl_3$ | >38.2 |
| Toluene | 18.6~12.4 |
| Heptane | <0.95 |
| DMA | >24.5 |
| $H_2O$ | <1.26 |

Slurry Conversion at Room Temperature (RT)

Slurry conversion experiments were conducted in 10 solvents or mixed solvents by suspending approximately 15 mg of ivosidenib in about 0.5 mL of solvent in a 1.5-mL glass vial at RT. After the suspension was stirred for 48 h, the remaining solids were centrifuged for XRPD analysis. Results summarized in Table 9 indicate seven forms of ivosidenib freebase (Forms C, D, E, F, G, H and I) were generated at RT.

TABLE 9

Slurry conversion experiments

| Solvent, v/v | Solid Form |
| --- | --- |
| MIBK | freebase Form E |
| Toluene | freebase Form F |
| EtOH/Heptane, 4:1 | freebase Form I |

TABLE 9-continued

Slurry conversion experiments

| Solvent, v/v | Solid Form |
| --- | --- |
| IPA/$H_2O$, 4:1 | freebase Form C |
| Dioxane/Heptane, 4:1 | amorphous |
| Acetone/$H_2O$, 4:1 | freebase Form I + amorphous |
| THF/Heptane, 4:1 | freebase Form G |
| ACN/$H_2O$, 4:1 | freebase Form D |
| Acetic acid/Heptane, 4:1 | freebase Form H |
| $CHCl_3$/$H_2O$, 4:1 | freebase Form G + amorphous |

Anti-Solvent Addition

A total of eight anti-solvent addition experiments were carried out by dissolving about 10 mg of ivosidenib freebase in 0.1-0.2 mL solvent to obtain a saturated solution, followed by addition of 0.1-0.7 mL anti-solvent. The precipitate was isolated for XRPD analysis. Results summarized in Table 10 indicate that two crystalline forms (freebase Form B and Form K) were generated.

TABLE 10

Anti-solvent trials

| Solvent/Anti-solvent | Solid Form |
| --- | --- |
| NMP/$H_2O$ | amorphous |
| DMA/$H_2O$ | amorphous |
| MeOH/$H_2O$ | freebase Form B |
| DMSO/$H_2O$ | amorphous |
| IPA/Heptane | amorphous |
| $CHCl_3$/Heptane | amorphous |
| THF/Heptane | freebase Form K |
| Acetone/Heptane | amorphous |

Slow Cooling

Slow cooling experiments were performed in 15 solvents or mixture solvents. Saturated solutions were prepared by dissolving about 15 mg of ivosidenib freebase in various solvents at 50° C. and stirred at 50° C. for 30 min. Then the solutions were cooled slowly to 5° C. at 0.1° C./min, and subsequently stirred at 5° C. overnight. The solids were isolated for XRPD analysis. The clear solutions were evaporated at RT for a week and the solids were tested by XRPD. Results summarized in Table 11 show five forms of ivosidenib freebase (Forms B, C, G, E and J) were discovered in slow cooling experiments.

TABLE 11 polymorph screenind by slow cooling

| Solvent, v/v | Solid Form |
| --- | --- |
| DMF/$H_2O$, 2:1 | clear |
| EtOH/$H_2O$, 8:7 | freebase Form B* |
| IPA | freebase Form C |
| ACN | oil |
| Acetone | amorphous |
| EtOAc | freebase Form G |
| IPAC | freebase Form E |
| MIBK | freebase Form E |
| 2-MeTHF | freebase Form J |
| MEK | freebase Form B |
| MTBE | amorphous |
| $CH_2Cl_2$ | oil |
| Dioxane/Heaptane, 9:1 | oil |
| Acetone/Heptane, 2:1 | oil |
| THF/$H_2O$, 4:1 | oil |

Slow Evaporation

Slow evaporation experiments were performed in 15 solvents by dissolving ~10 mg of ivosidenib freebase in 0.2-0.4 mL of solvent in a 3 mL glass vial. The resulting visually clear solutions were covered with caps and subjected to slow evaporation to induce precipitation. The solids were isolated for XRPD analysis and the results summarized in Table 12 indicate that freebase Type B and Type C were generated.

TABLE 12 polymorph screening by slow evaporation

| Solvent, v/v | Solid Form |
|---|---|
| MeOH | amorphous |
| EtOH | amorphous |
| IPA | freebase Form C |
| ACN | amorphous |
| Acetone | amorphous |
| EtOAc | oil |
| IPAC | amorphous |
| MTBE | oil |
| THF | oil |
| CHCl$_3$ | amorphous |
| 1,4-Dioxane | amorphous |
| Acetic acid | amorphous |
| MeOH/H$_2$O, 9:1 | freebase Form B |
| ACN/H$_2$O, 4:1 | amorphous |
| Acetone/Heptane, 9:1 | amorphous |

Characterization of Form C

Figure 15:
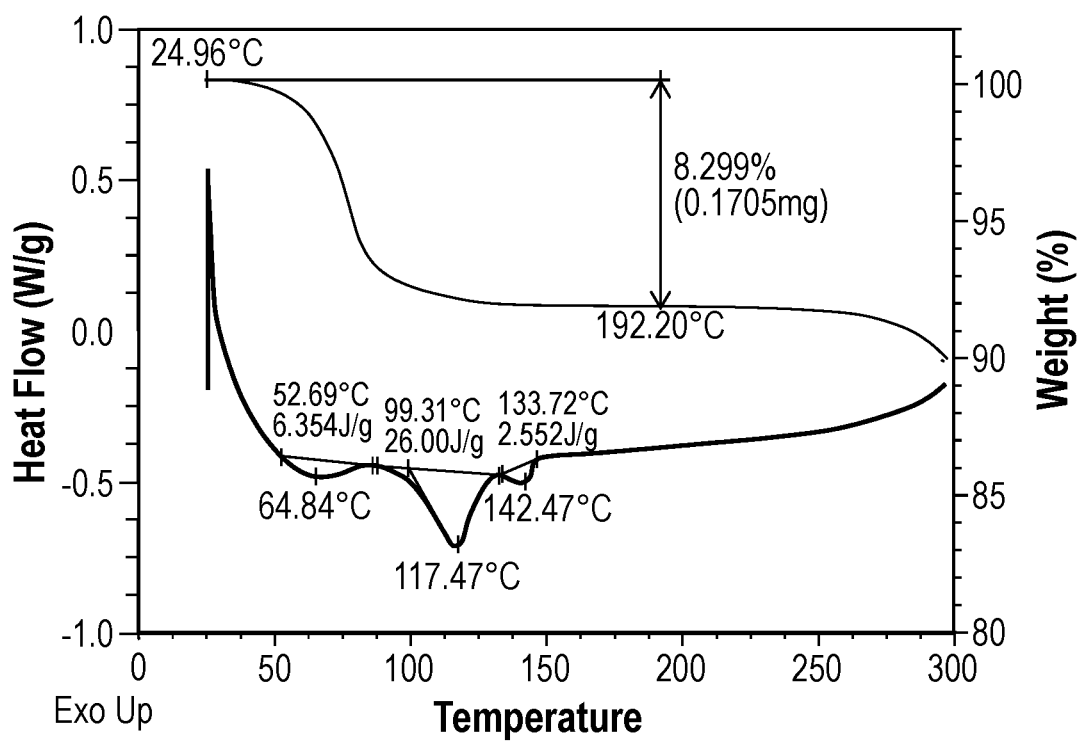
FIG. 15 is a combined plot of TGA and DSC analyses of Form C of ivosidenib.
Figure 16:
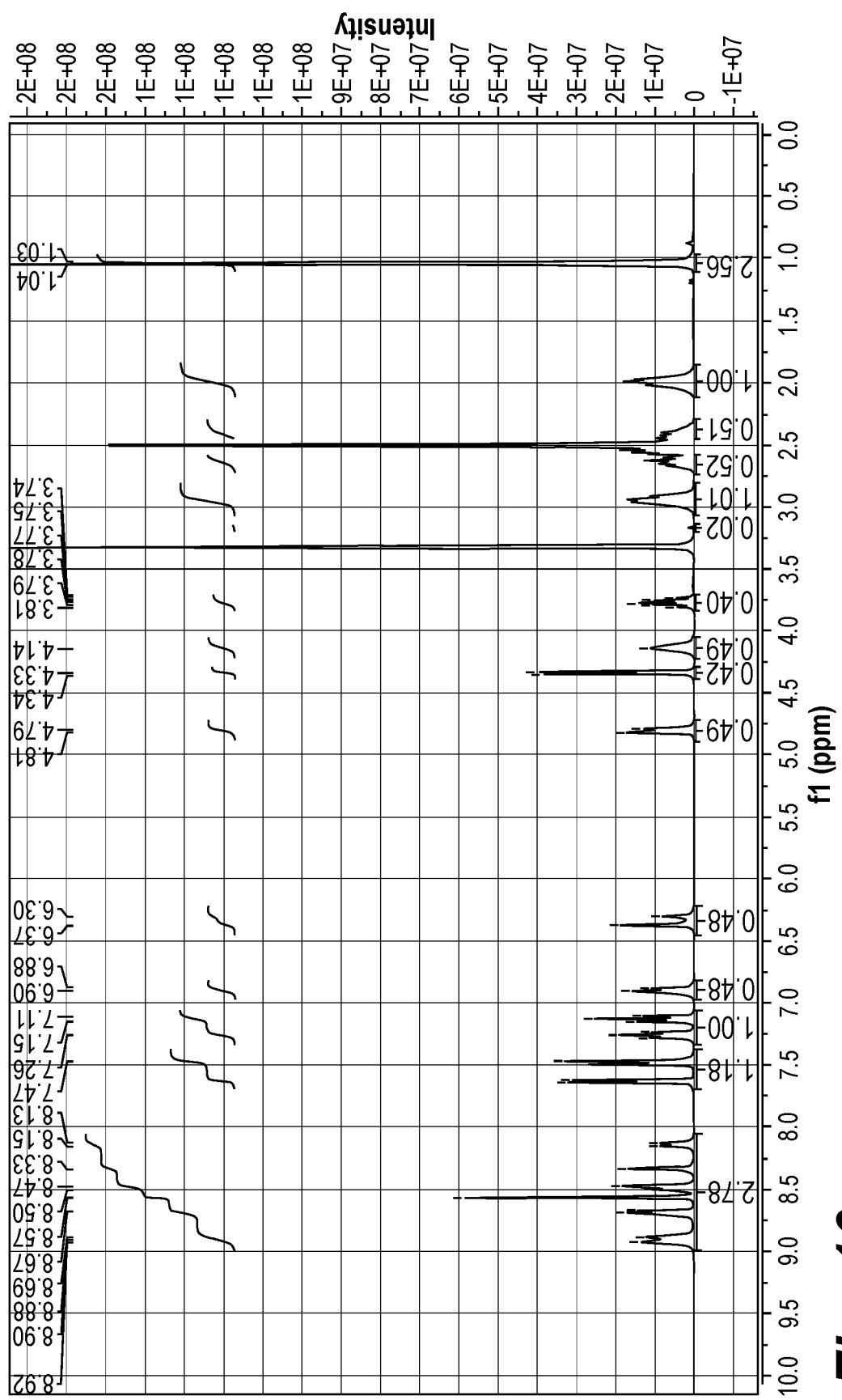
FIG. 16 is an NMR spectrum of Form C of ivosidenib.
Figure 17:
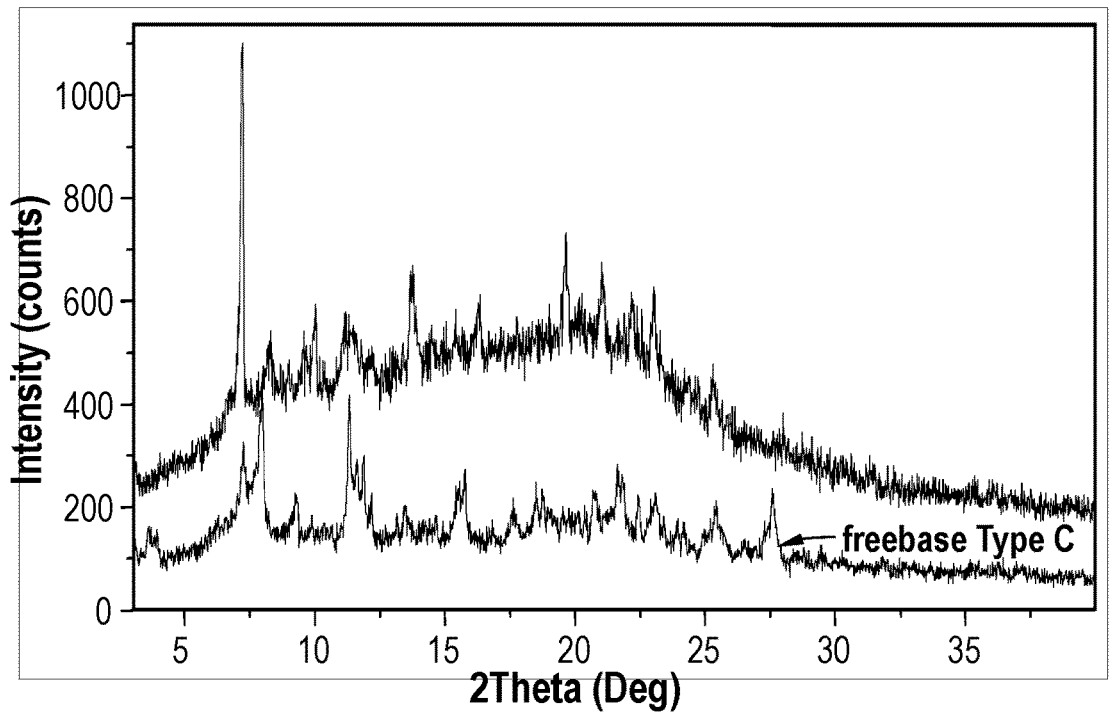
FIG. 17 is an XRPD diffractogram of Form D of ivosidenib.

The XRPD pattern of ivosidenib freebase Form C sample shown in FIG. 15 indicates that it is a crystalline form. The DSC and TGA overlay of ivosidenib freebase Form C is displayed in FIG. 16. The TGA data shows ~8.3 wt % weight loss before 192.2° C. Three endothermic peaks were observed at 52.7° C., 99.3° C. and 133.7° C. (onset) in DSC curve due to the evaporation of remaining solvent. The H$^1$ NMR spectrum (FIG. 17) shows that IPA is the main solvent contained in freebase Form C. The NMR results indicate that the IPA content is 8.0% which conforms to 8.3 wt % weight loss in TGA curve. The results suggest freebase Form C is an IPA solvate.

TABLE 13

XRPD peaks of Form C of ivosidenib

| Pos. [°2Th.] | Height [cts] | FWHM Left [°2Th.] | d-spacing [Å] | Rel. Int. [%] |
|---|---|---|---|---|
| 3.8 | 46.300740 | 0.401472 | 23.46889 | 11.71 |
| 7.3 | 241.140300 | 0.133824 | 12.13444 | 60.99 |
| 8.0 | 395.400100 | 0.050184 | 11.02412 | 100.00 |
| 9.3 | 113.455600 | 0.100368 | 9.51782 | 28.69 |
| 11.3 | 374.029900 | 0.083640 | 7.81079 | 94.60 |
| 11.9 | 219.648500 | 0.066912 | 7.45421 | 55.55 |
| 12.2 | 104.524200 | 0.100368 | 7.27595 | 26.44 |
| 13.5 | 86.832810 | 0.200736 | 6.56156 | 21.96 |
| 15.8 | 182.680700 | 0.100368 | 5.61815 | 46.20 |
| 17.7 | 101.392400 | 0.267648 | 5.02136 | 25.64 |
| 18.6 | 117.819400 | 0.535296 | 4.76330 | 29.80 |
| 20.7 | 156.030500 | 0.200736 | 4.28895 | 39.46 |
| 21.6 | 217.857800 | 0.100368 | 4.10828 | 55.10 |
| 22.5 | 151.701700 | 0.133824 | 3.95953 | 38.37 |
| 23.1 | 150.989000 | 0.401472 | 3.85292 | 38.19 |
| 25.4 | 121.780700 | 0.200736 | 3.50233 | 30.80 |
| 27.6 | 172.247100 | 0.133824 | 3.23157 | 43.56 |

Peaks were searched in X'Pert HighScore Plus (version 3.0) with the following parameters: minimum significance=2.0, minimum tip width=0.01 degree 2 theta, maximum tip width=1.00 degree 2 theta, peak base width=2.00 degrees 2 theta, method=minimum 2$^{nd}$ derivative.

Form D

Figure 18:
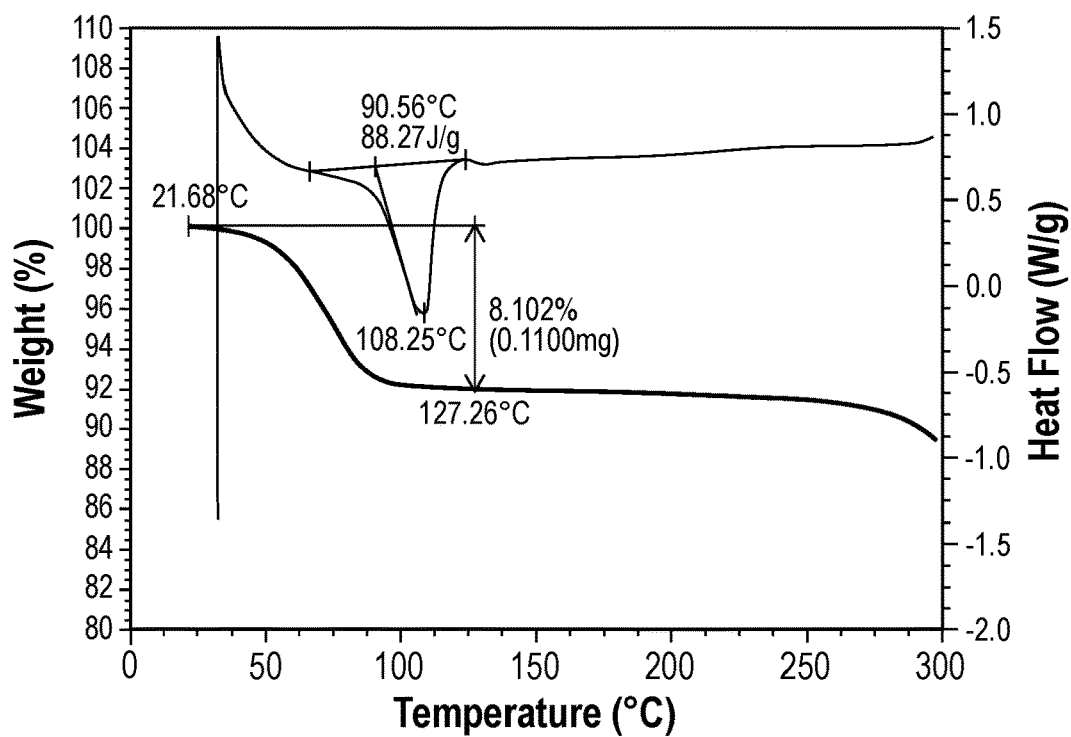
FIG. 18 is a combined plot of TGA and DSC analyses of Form D of ivosidenib.
Figure 19:
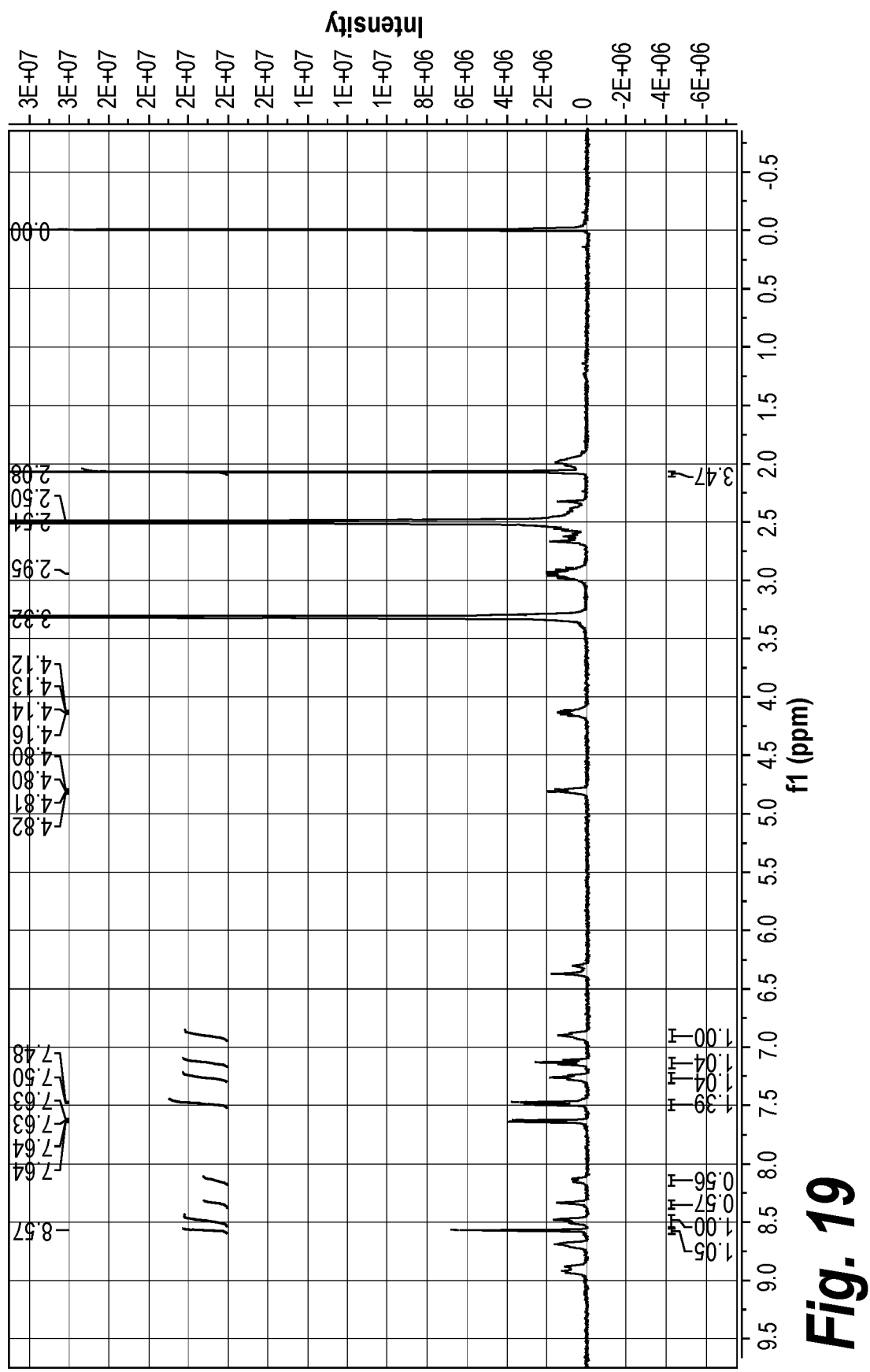
FIG. 19 is an NMR spectrum of Form D of ivosidenib.
Figure 20:
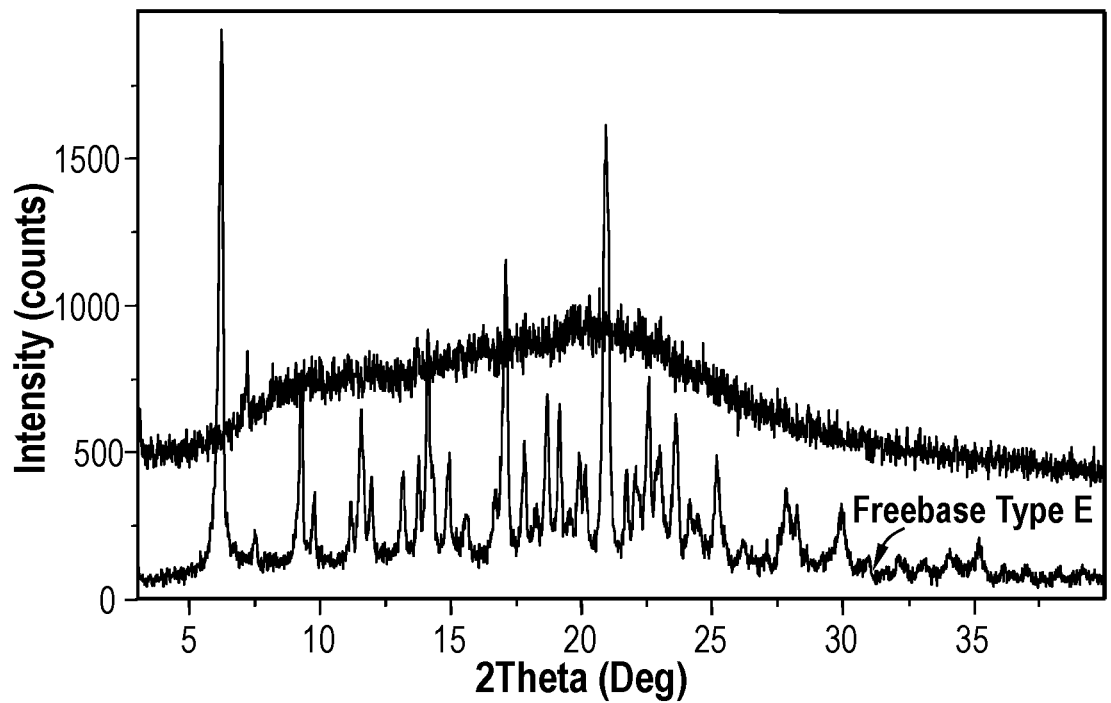
FIG. 20 is an XRPD diffractogram of Form E of ivosidenib.

The XRPD pattern of ivosidenib freebase Form D sample shown in FIG. 18 indicates that it is a crystalline form which differs from that of ivosidenib freebase Form A. The DSC and TGA overlay of Form D is displayed in FIG. 19. The TGA data shows ~8.1 wt % weight loss before 127.3° C. An endotherm was observed at 90.6° C. in DSC curve due to the evaporation of remaining solvent. The $^1$H NMR result displayed in FIG. 20 shows $^1$H peaks of methyl of acetonitrile (ACN) is at 2.08 ppm, and $^1$H NMR peaks of (2S)—N-{(1S)-1-(2-chlorophenyl)-2-[(3,3-difluorocyclobutyl)amino]-2-oxoethyl}-1-(4-cyanopyridin-2-yl)-N-(5-fluoropyridin-3-yl)-5-oxopyrrolidine-2-carboxamide are at 8.57-7.48 ppm. According to the area ratio, the mole equivalent of (2S)—N-{(1S)-1-(2-chlorophenyl)-2-[(3,3-difluorocyclobutyl)amino]-2-oxoethyl}-1-(4-cyanopyridin-2-yl)-N-(5-fluoropyridin-3-yl)-5-oxopyrrolidine-2-carboxamide and ACN is about 1:1.2, which conforms to the weight loss of TGA curve, demonstrating that freebase Form D is an acetontrile solvate, more particularly a mono-ACN solvate.

TABLE 14

XRPD peaks of Form D of ivosidenib

| Pos. [°2Th.] | Height [cts] | FWHM Left [°2Th.] | d-spacing [Å] | Rel. Int. [%] |
|---|---|---|---|---|
| 7.3 | 548.365400 | 0.083640 | 12.18129 | 61.38 |
| 8.4 | 893.350500 | 0.066912 | 10.54354 | 100.00 |
| 10.2 | 393.378200 | 0.083640 | 8.65353 | 44.03 |
| 10.3 | 274.857400 | 0.050184 | 8.55365 | 30.77 |
| 11.1 | 384.949100 | 0.100368 | 7.93789 | 43.09 |
| 12.7 | 101.483700 | 0.100368 | 6.95793 | 11.36 |
| 13.4 | 253.768000 | 0.066912 | 6.60043 | 28.41 |
| 14.6 | 221.405200 | 0.066912 | 6.04679 | 24.78 |
| 16.3 | 184.781600 | 0.133824 | 5.42473 | 20.68 |
| 17.0 | 203.753100 | 0.050184 | 5.22714 | 22.81 |
| 17.9 | 157.137500 | 0.267648 | 4.96587 | 17.59 |
| 19.4 | 427.650200 | 0.100368 | 4.57537 | 47.87 |
| 20.4 | 133.373700 | 0.133824 | 4.34441 | 14.93 |
| 21.3 | 127.376300 | 0.133824 | 4.17020 | 14.26 |
| 21.8 | 181.819900 | 0.133824 | 4.08091 | 20.35 |
| 23.4 | 116.862800 | 0.200736 | 3.79763 | 13.08 |
| 24.6 | 137.311200 | 0.100368 | 3.61604 | 15.37 |
| 25.2 | 469.609200 | 0.150552 | 3.53474 | 52.57 |
| 25.6 | 168.041400 | 0.133824 | 3.48081 | 18.81 |
| 26.1 | 109.545600 | 0.133824 | 3.41465 | 12.26 |
| 26.6 | 85.400340 | 0.200736 | 3.34803 | 9.56 |
| 28.1 | 51.930940 | 0.401472 | 3.17849 | 5.81 |
| 28.8 | 40.294450 | 0.200736 | 3.10021 | 4.51 |

Peaks were searched in X'Pert HighScore Plus (version 3.0) with the following parameters: minimum significance=2.0, minimum tip width=0.01 degree 2 theta, maximum tip width=1.00 degree 2 theta, peak base width=2.00 degrees 2 theta, method=minimum 2$^{nd}$ derivative.

Form E

Figure 21:
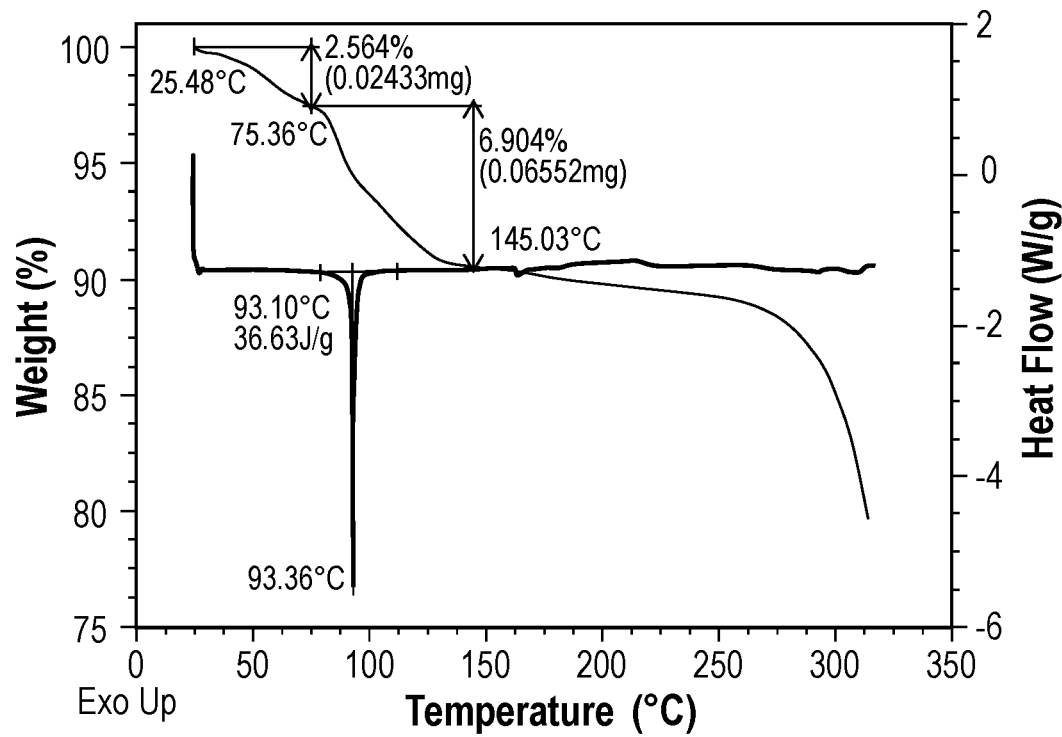
FIG. 21 is a combined plot of TGA and DSC analyses of Form E of ivosidenib.
Figure 22:
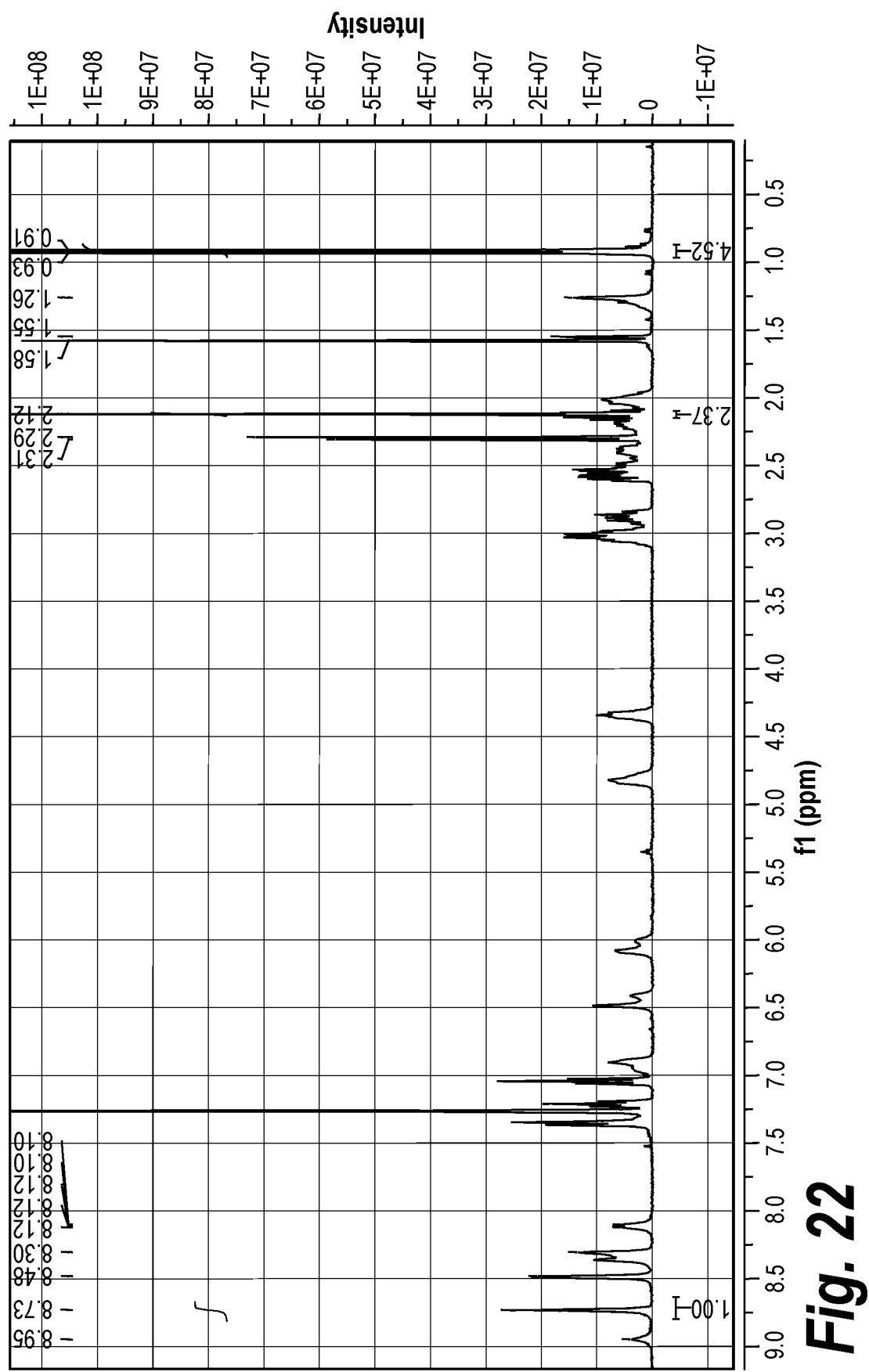
FIG. 22 is an NMR spectrum of Form E of ivosidenib.
Figure 23:
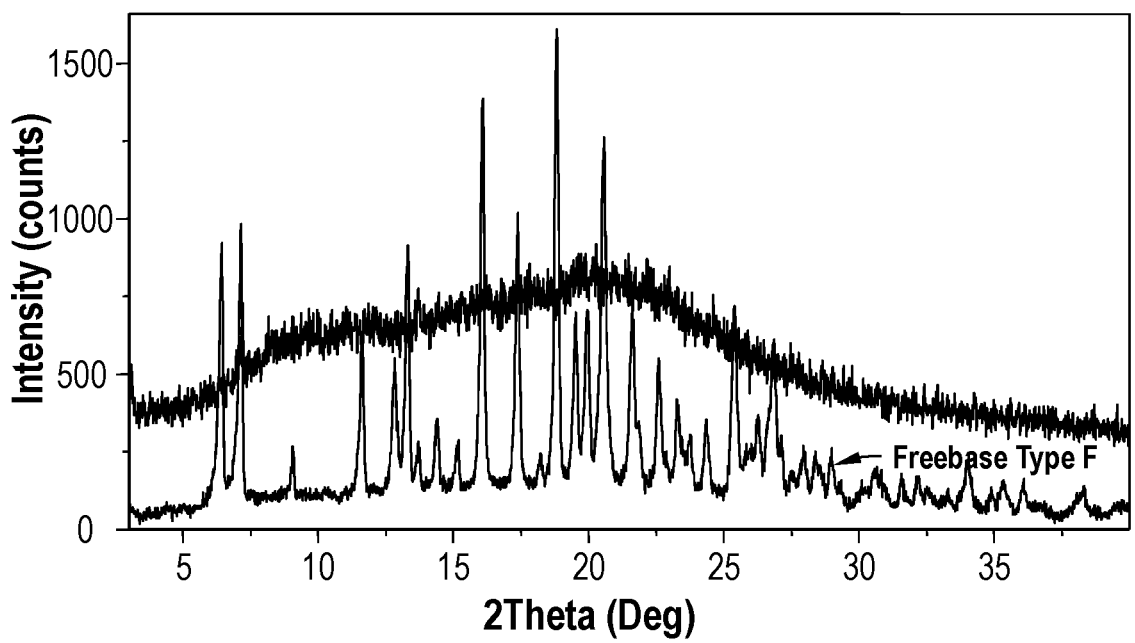
FIG. 23 is an XRPD diffractogram of Form F of ivosidenib.

The XRPD pattern of ivosidenib freebase Type E sample shown in FIG. 21 indicates that it is a crystalline form which differs from that of Form A. The DSC and TGA overlay of ivosidenib freebase Form E is displayed in FIG. 22. The TGA data shows ~9.5 wt % weight loss before 145.0° C. An endotherm was observed at 93.1° C. in DSC curve due to the evaporation of remaining solvent. The TGA and DSC results suggest freebase Form E is a solvate. The $^1$H NMR result displayed in FIG. 23 shows $^1$H NMR peaks representing the two methyl of isobutyl from methyl isobutyl ketone (MIBK) at 0.92 ppm, and one peak representing ivosidenib at 8.73 ppm. According to the area ratio, the mole equivalent of (2S)—N-{(1S)-1-(2-chlorophenyl)-2-[(3,3-difluorocyclobutyl)amino]-2-oxoethyl}-1-(4-cyanopyridin-2-yl)-N-(5-fluoropyridin-3-yl)-5-oxopyrrolidine-2-carboxamide and MIBK is about 1:0.7, which conforms to the weight loss of TGA, suggesting freebase Type E is a MIBK solvate, specifically an isopropyl acetate solvate.

The peaks by XRPD of Form E of ivosidenib are defined as follows. Form E may be characterized by one or two or three or four or five or six or seven or eight or nine of the peaks shown in Table 15.

TABLE 15

XRPD peaks of Form E of ivosidenib

| No. | Pos. [°2θ] | Area [cts*°2θ] | Backgr. [cts] | d-spacing [Å] | Height [cts] | Rel. Int. [%] |
|---|---|---|---|---|---|---|
| 1.00 | 5.5 | 8.39 | 348.16 | 15.96 | 110.75 | 2.42 |
| 2.00 | 6.1 | 18.79 | 343.01 | 14.42 | 496.34 | 10.83 |
| 3.00 | 6.3 | 231.40 | 341.81 | 14.10 | 4584.42 | 100.00 |
| 4.00 | 7.6 | 12.88 | 330.34 | 11.65 | 85.05 | 1.86 |
| 5.00 | 9.3 | 15.38 | 315.88 | 9.56 | 304.67 | 6.65 |
| 6.00 | 9.4 | 20.30 | 314.97 | 9.46 | 321.69 | 7.02 |
| 7.00 | 9.8 | 11.61 | 310.83 | 9.00 | 306.69 | 6.69 |
| 8.00 | 11.2 | 22.11 | 334.83 | 7.89 | 219.06 | 4.78 |
| 9.00 | 11.5 | 30.45 | 340.40 | 7.69 | 804.38 | 17.55 |
| 10.00 | 11.6 | 125.43 | 342.49 | 7.62 | 2485.08 | 54.21 |
| 11.00 | 12.0 | 103.32 | 350.10 | 7.35 | 1637.57 | 35.72 |
| 12.00 | 13.2 | 21.12 | 370.13 | 6.71 | 278.97 | 6.09 |
| 13.00 | 13.9 | 35.95 | 380.50 | 6.39 | 569.80 | 12.43 |
| 14.00 | 14.3 | 70.79 | 386.41 | 6.21 | 1122.04 | 24.48 |
| 15.00 | 14.4 | 25.60 | 387.81 | 6.17 | 676.37 | 14.75 |
| 16.00 | 15.0 | 25.30 | 395.59 | 5.92 | 334.21 | 7.29 |
| 17.00 | 15.3 | 14.93 | 399.41 | 5.80 | 197.19 | 4.30 |
| 18.00 | 15.7 | 32.33 | 403.78 | 5.66 | 366.02 | 7.98 |
| 19.00 | 16.8 | 60.36 | 414.70 | 5.27 | 797.18 | 17.39 |
| 20.00 | 17.1 | 175.05 | 416.44 | 5.19 | 1981.79 | 43.23 |
| 21.00 | 17.8 | 13.12 | 420.58 | 4.99 | 346.58 | 7.56 |
| 22.00 | 17.9 | 83.97 | 421.15 | 4.96 | 950.61 | 20.74 |
| 23.00 | 18.3 | 25.90 | 422.60 | 4.86 | 171.06 | 3.73 |
| 24.00 | 18.8 | 42.11 | 423.95 | 4.72 | 476.69 | 10.40 |
| 25.00 | 19.1 | 28.56 | 424.28 | 4.64 | 565.90 | 12.34 |
| 26.00 | 19.3 | 116.74 | 424.43 | 4.60 | 1156.39 | 25.22 |
| 27.00 | 19.6 | 18.10 | 424.29 | 4.54 | 358.69 | 7.82 |
| 28.00 | 19.9 | 24.11 | 423.97 | 4.46 | 318.46 | 6.95 |
| 29.00 | 20.1 | 52.25 | 423.44 | 4.40 | 837.28 | 18.26 |
| 30.00 | 20.2 | 35.49 | 423.29 | 4.39 | 937.49 | 20.45 |
| 31.00 | 20.9 | 49.08 | 421.03 | 4.26 | 1296.56 | 28.28 |
| 32.00 | 21.0 | 289.13 | 420.27 | 4.23 | 4582.61 | 99.96 |
| 33.00 | 22.0 | 66.16 | 414.11 | 4.04 | 873.80 | 19.06 |
| 34.00 | 22.5 | 42.73 | 410.57 | 3.95 | 684.85 | 14.94 |
| 35.00 | 22.5 | 46.51 | 409.97 | 3.94 | 921.44 | 20.10 |
| 36.00 | 23.0 | 162.81 | 405.63 | 3.86 | 2150.35 | 46.91 |
| 37.00 | 23.6 | 103.15 | 399.76 | 3.77 | 2043.53 | 44.58 |
| 38.00 | 24.2 | 78.95 | 393.23 | 3.68 | 1042.73 | 22.75 |
| 39.00 | 24.5 | 20.21 | 389.59 | 3.64 | 200.19 | 4.37 |
| 40.00 | 25.0 | 27.64 | 383.25 | 3.56 | 547.69 | 11.95 |
| 41.00 | 25.3 | 117.11 | 379.68 | 3.53 | 928.09 | 20.24 |
| 42.00 | 26.2 | 12.62 | 366.25 | 3.40 | 125.03 | 2.73 |
| 43.00 | 27.6 | 33.17 | 346.93 | 3.24 | 328.58 | 7.17 |
| 44.00 | 27.9 | 28.71 | 341.69 | 3.20 | 189.62 | 4.14 |
| 45.00 | 28.3 | 18.94 | 336.10 | 3.16 | 375.32 | 8.19 |
| 46.00 | 29.2 | 14.29 | 321.26 | 3.06 | 94.39 | 2.06 |
| 47.00 | 29.8 | 21.89 | 312.05 | 3.00 | 578.37 | 12.62 |
| 48.00 | 30.3 | 17.32 | 305.15 | 2.96 | 274.59 | 5.99 |
| 49.00 | 30.8 | 14.36 | 297.15 | 2.91 | 71.13 | 1.55 |
| 50.00 | 31.5 | 11.34 | 284.87 | 2.84 | 74.86 | 1.63 |
| 51.00 | 32.5 | 20.41 | 269.47 | 2.76 | 134.77 | 2.94 |
| 52.00 | 33.0 | 20.96 | 268.36 | 2.72 | 83.04 | 1.81 |
| 53.00 | 34.1 | 16.46 | 290.71 | 2.63 | 163.02 | 3.56 |
| 54.00 | 34.5 | 8.94 | 311.74 | 2.60 | 143.32 | 3.13 |
| 55.00 | 34.8 | 19.09 | 325.52 | 2.58 | 378.13 | 8.25 |

Form F

Figure 24:
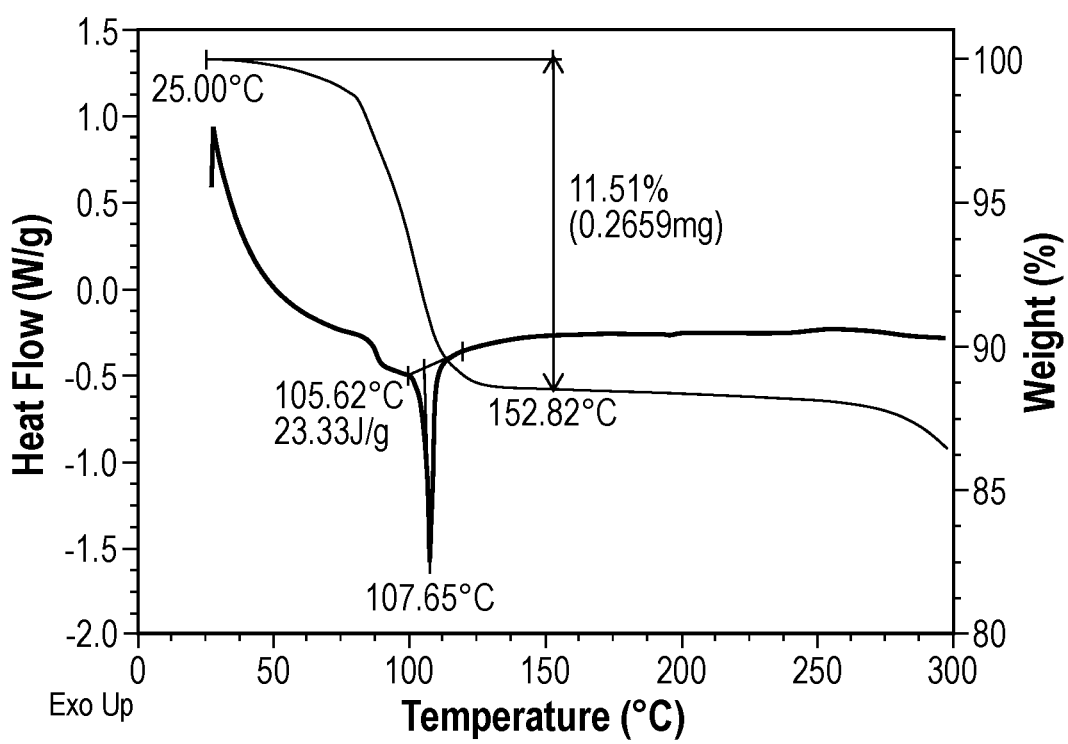
FIG. 24 is a combined plot of TGA and DSC analyses of Form F of ivosidenib.
Figure 25:
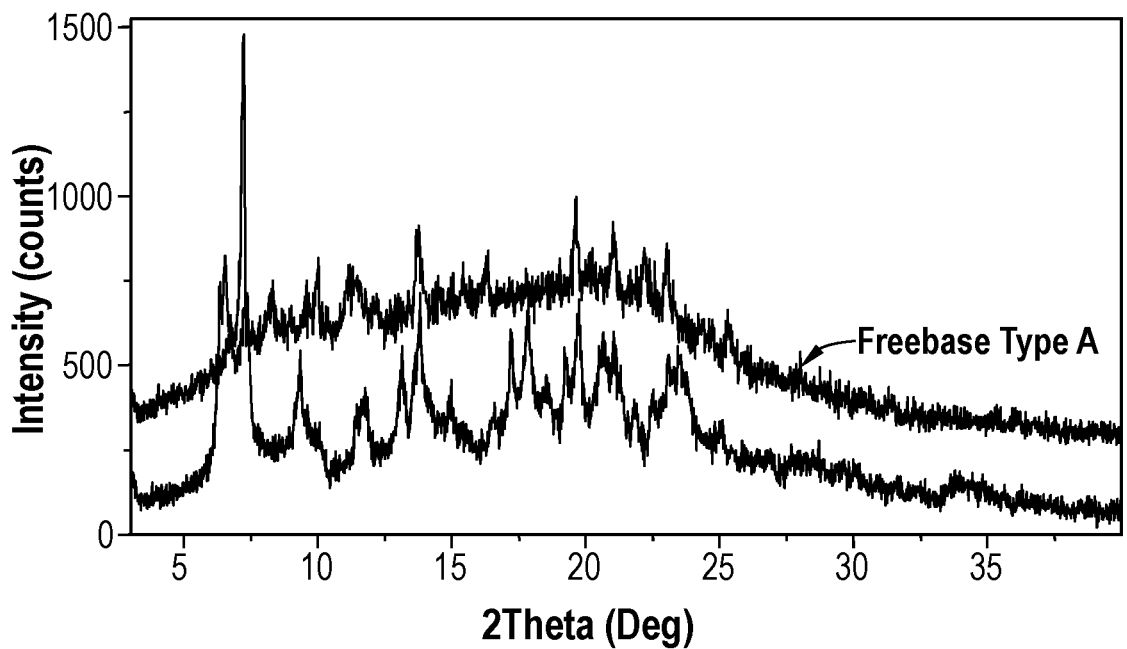
FIG. 25 is an XRPD diffractogram of Form G of ivosidenib.

The XRPD pattern of ivosidenib freebase Form F sample shown in FIG. 24 indicates that it is a crystalline form which differs from that of Form A. The DSC and TGA overlay of ivosidenib freebase Form F is displayed in FIG. 25. The TGA data shows ~11.5 wt % weight loss before 152.8° C. An endotherm was observed at 105.6° C. in DSC curve. The TGA and DSC results suggest freebase Form F is likely a solvate or hydrate.

TABLE 16

XRPD peaks of Form F of ivosidenib

| Pos. [°2Th.] | Height [cts] | FWHM Left [°2Th.] | d-spacing [Å] | Rel. Int. [%] |
|---|---|---|---|---|
| 6.5 | 1086.979000 | 0.117096 | 13.68154 | 52.77 |
| 7.2 | 1151.151000 | 0.100368 | 12.31814 | 55.88 |
| 9.1 | 244.587100 | 0.066912 | 9.72595 | 11.87 |
| 11.7 | 664.987100 | 0.133824 | 7.58351 | 32.28 |
| 12.8 | 650.677100 | 0.133824 | 6.89427 | 31.59 |
| 13.3 | 1130.126000 | 0.133824 | 6.63824 | 54.86 |
| 13.7 | 284.674700 | 0.133824 | 6.45331 | 13.82 |
| 14.4 | 381.854100 | 0.150552 | 6.14904 | 18.54 |
| 15.2 | 287.244300 | 0.133824 | 5.84115 | 13.94 |
| 16.1 | 1772.357000 | 0.117096 | 5.50364 | 86.04 |
| 17.4 | 1200.352000 | 0.167280 | 5.09533 | 58.27 |
| 18.2 | 241.634000 | 0.133824 | 4.86657 | 11.73 |
| 18.8 | 2059.915000 | 0.133824 | 4.70864 | 100.00 |
| 19.5 | 819.051400 | 0.133824 | 4.55089 | 39.76 |
| 20.0 | 870.585800 | 0.133824 | 4.44427 | 42.26 |
| 20.6 | 1626.584000 | 0.117096 | 4.31448 | 78.96 |
| 21.6 | 818.280300 | 0.133824 | 4.10662 | 39.72 |
| 22.6 | 660.516600 | 0.133824 | 3.93602 | 32.07 |
| 23.3 | 471.948900 | 0.100368 | 3.81792 | 22.91 |
| 23.8 | 320.357400 | 0.133824 | 3.74633 | 15.55 |
| 24.3 | 392.720700 | 0.133824 | 3.65617 | 19.06 |
| 25.4 | 897.012000 | 0.117096 | 3.50659 | 43.55 |
| 26.3 | 407.102800 | 0.117096 | 3.38897 | 19.76 |
| 26.8 | 687.800600 | 0.133824 | 3.32176 | 33.39 |
| 28.0 | 263.638700 | 0.167280 | 3.18905 | 12.80 |
| 28.4 | 249.314700 | 0.100368 | 3.14472 | 12.10 |
| 29.0 | 237.219700 | 0.133824 | 3.08287 | 11.52 |
| 30.5 | 168.470800 | 0.167280 | 2.92873 | 8.18 |
| 31.6 | 153.652800 | 0.133824 | 2.83369 | 7.46 |
| 32.2 | 155.988900 | 0.167280 | 2.78108 | 7.57 |
| 34.0 | 220.356200 | 0.200736 | 2.63550 | 10.70 |
| 34.9 | 93.962200 | 0.200736 | 2.57241 | 4.56 |
| 35.3 | 136.162100 | 0.200736 | 2.54045 | 6.61 |
| 36.1 | 135.162000 | 0.167280 | 2.48978 | 6.56 |
| 38.3 | 120.879200 | 0.100368 | 2.34932 | 5.87 |

Peaks were searched in X'Pert HighScore Plus (version 3.0) with the following parameters: minimum significance=2.0, minimum tip width=0.01 degree 2 theta, maximum tip width=1.00 degree 2 theta, peak base width=2.00 degrees 2 theta, method=minimum $2^{nd}$ derivative.

Form G

Figure 26:
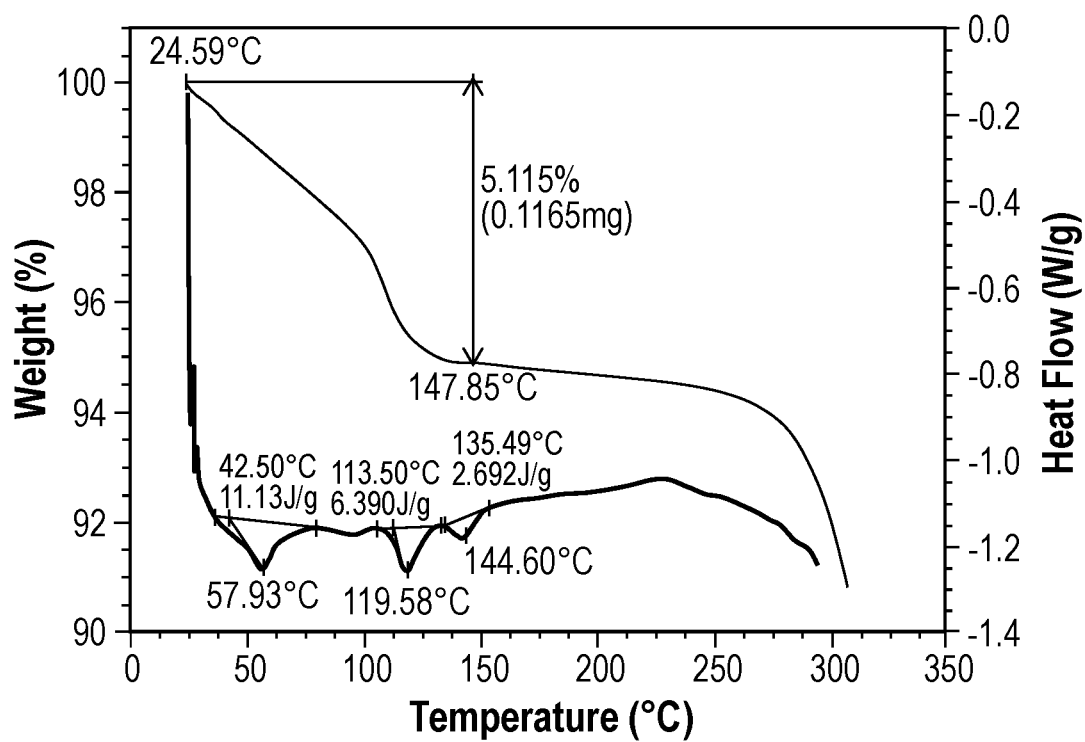
FIG. 26 is a combined plot of TGA and DSC analyses of Form G of ivosidenib.
Figure 27:
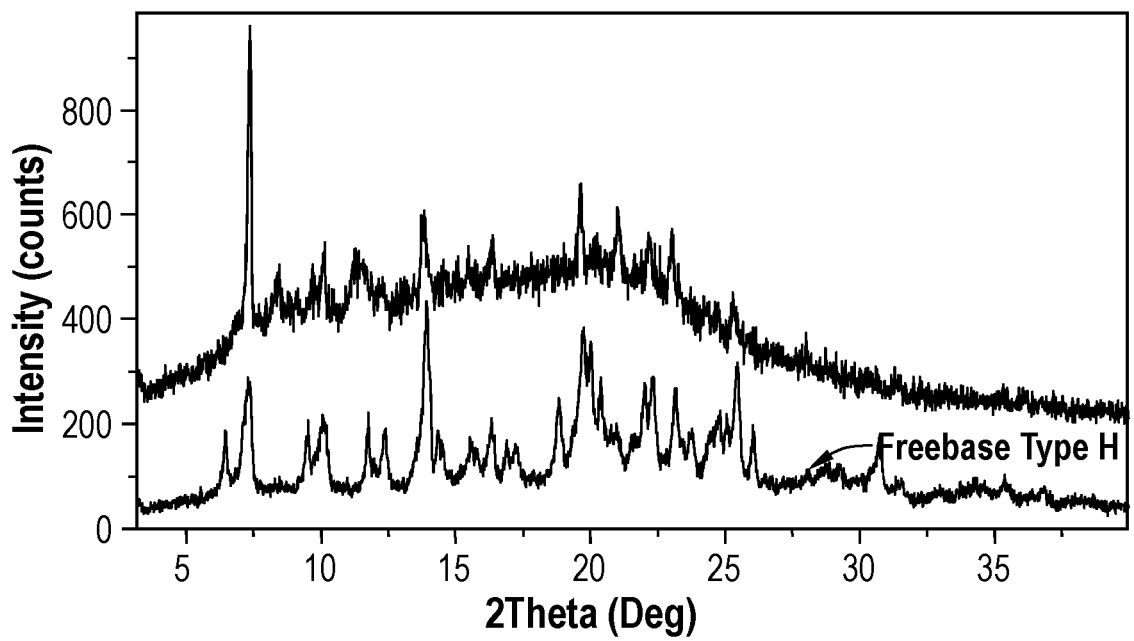
FIG. 27 is an XRPD diffractogram of Form H of ivosidenib.

The XRPD pattern of ivosidenib freebase Form G sample shown in FIG. 26 indicates that it is a crystalline form, which differs from that of Form A. The DSC and TGA overlay of ivosidenib freebase Form G is displayed in FIG. 27. The TGA data shows ~5.1 wt % weight loss before 147.9° C. Three endothermic peaks were observed at 42.5° C., 113.5° C. and 135.5° C. (onset) in DSC curve. The TGA and DSC results suggest freebase Form G is likely a solvate or hydrate.

Form H

Figure 28:
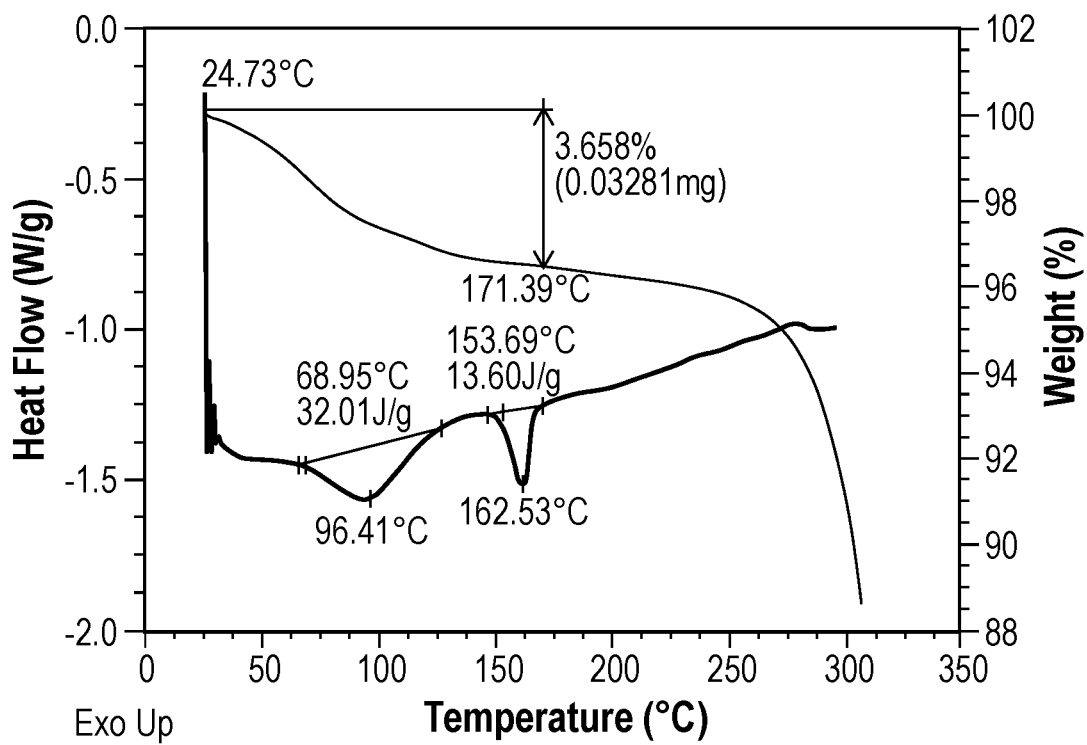
FIG. 28 is a combined plot of TGA and DSC analyses of Form H of ivosidenib.
Figure 29:
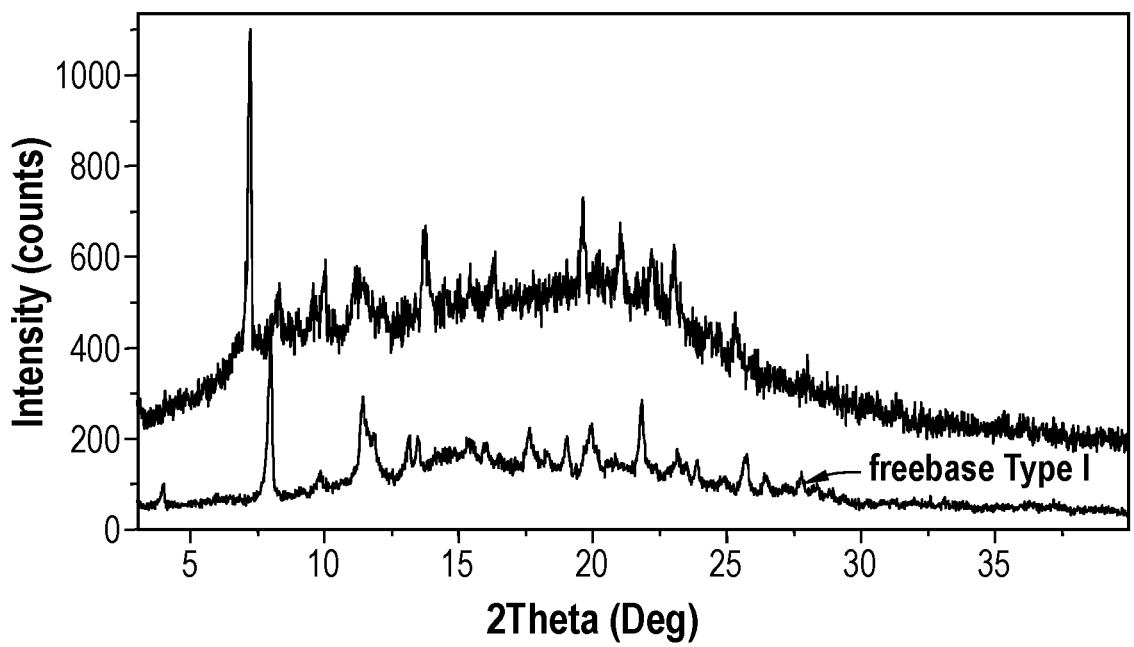
FIG. 29 is an XRPD diffractogram of Form I of ivosidenib.

The XRPD pattern of ivosidenib freebase Form H sample shown in FIG. 28 indicates that it is a crystalline form which differs from that of Form A. The DSC and TGA overlay of ivosidenib freebase Form H is displayed in FIG. 29. The TGA data shows ~3.7 wt % weight loss before 171.4° C. Two endothermic peaks were observed at 69.0° C. and 153.7° C. (onset) in DSC curve. The TGA and DSC results suggest freebase Form H is likely a solvate or hydrate.

Form I

Figure 30:
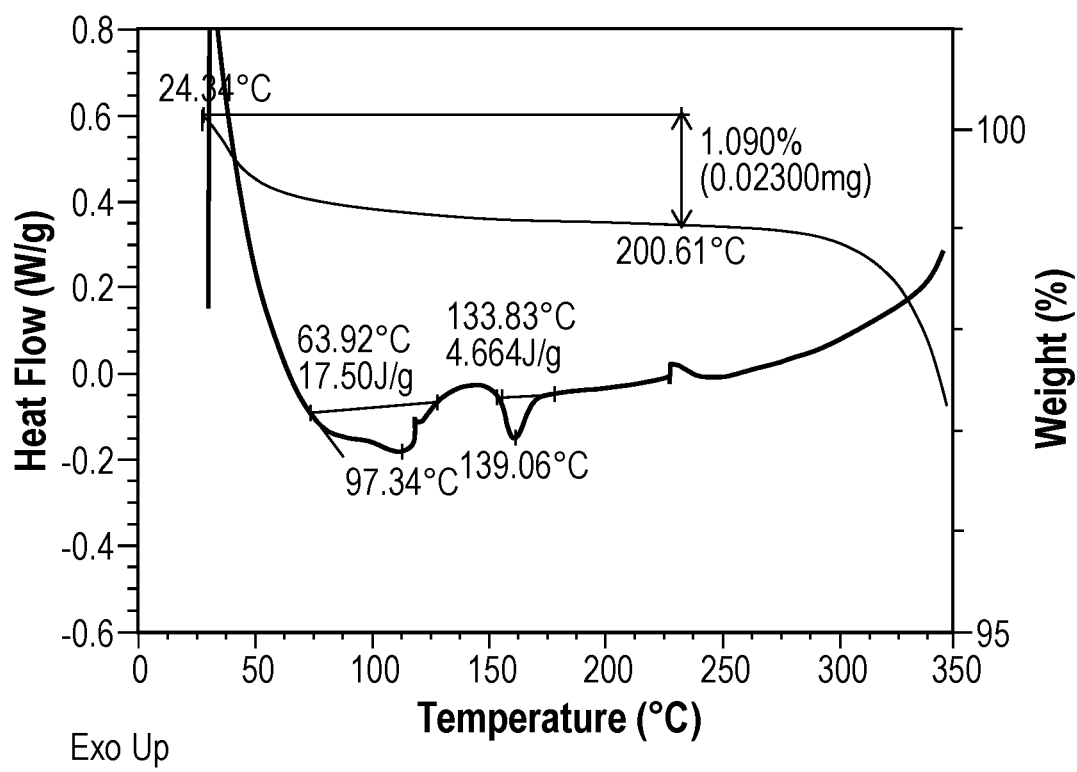
FIG. 30 is a combined plot of TGA and DSC analyses of Form I of ivosidenib.
Figure 31:
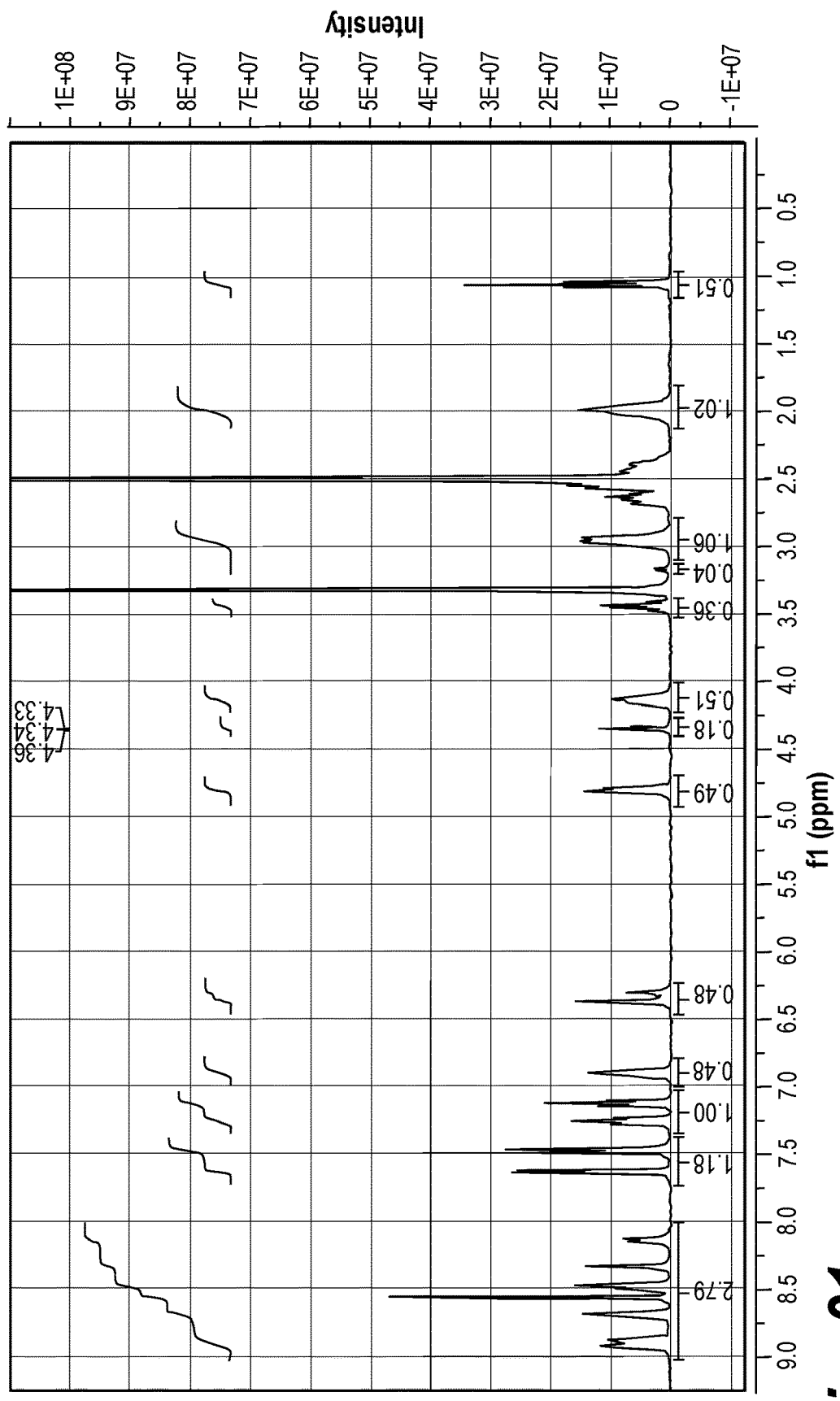
FIG. 31 is an NMR spectrum of Form I of ivosidenib.
Figure 32:
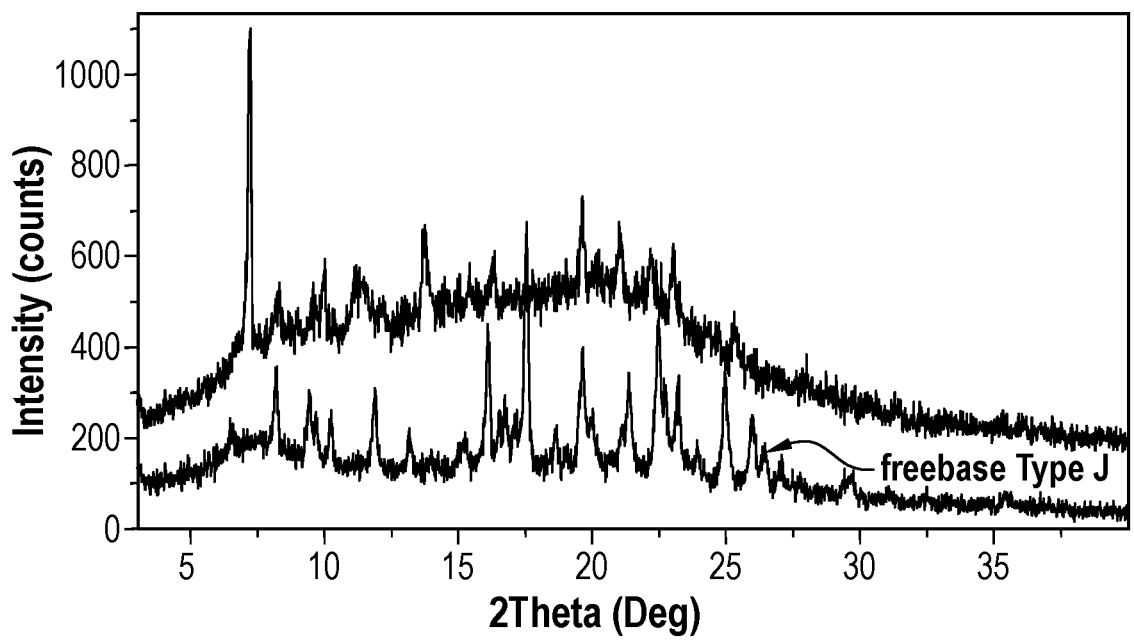
FIG. 32 is an XRPD diffractogram of Form J of ivosidenib.

The XRPD pattern of ivosidenib freebase Form I shown in FIG. 30 indicates that it is a partially crystalline form. The DSC and TGA overlay of ivosidenib freebase Form I is displayed in FIG. 31. The TGA data shows ~1.1 wt % weight loss before 200.6° C. which is probably due to the existence of residual solvent. Two endothermic peaks were observed at 63.9° C. and 133.8° C. (onset) in DSC curve. The H$^1$ NMR spectrum (FIG. 32) shows that EtOH is the main solvent contained in freebase Form I. The peak at 1.0 ppm represents the methyl group from EtOH, and the peak at 7.5 ppm is from (2S)—N-{(1S)-1-(2-chlorophenyl)-2-[(3,3-difluorocyclobutyl)amino]-2-oxoethyl}-1-(4-cyanopyridin-2-yl)-N-(5-fluoropyridin-3-yl)-5-oxopyrrolidine-2-carboxamide. According to the area ratio, the mole equivalent of (2S)—N-{(1S)-1-(2-chlorophenyl)-2-[(3,3-difluorocyclobutyl)amino]-2-oxoethyl}-1-(4-cyanopyridin-2-yl)-N-(5-fluoropyridin-3-yl)-5-oxopyrrolidine-2-carboxamide and EtOH is 1:0.34.

A characteristic XRPD peak by which Form I may be identified occurs at about 8.1°.

Form I of ivosidenib is an anhydrate/solvate form.

Form J

Figure 33:
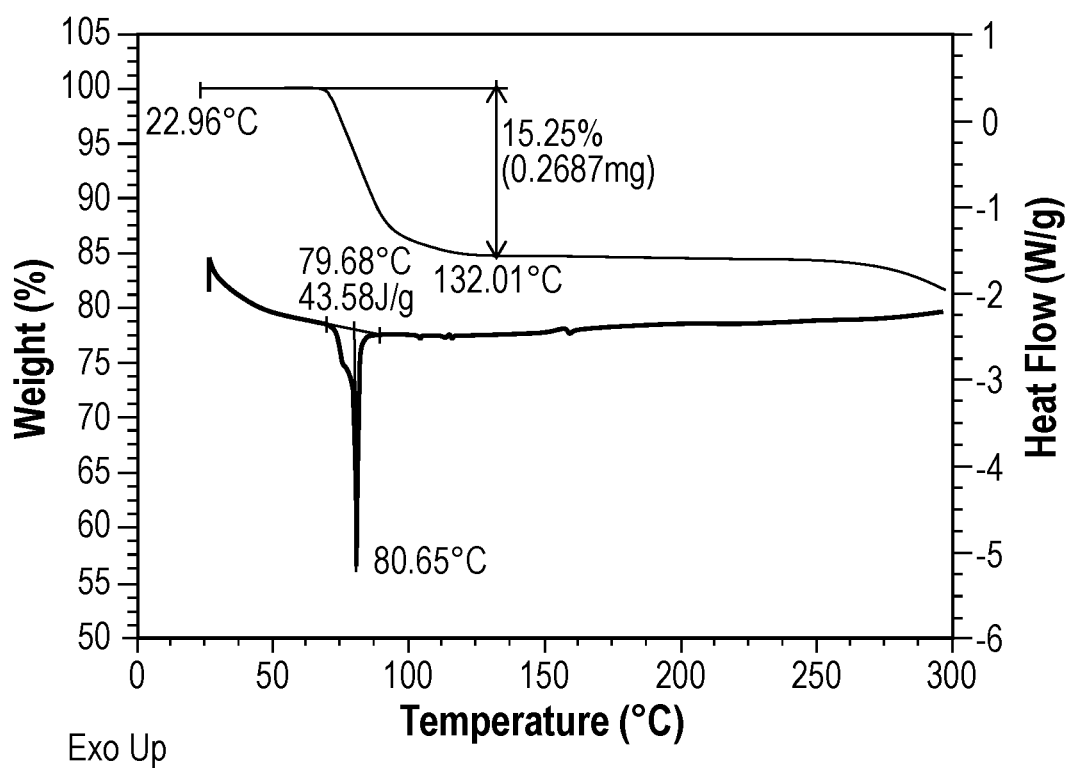
FIG. 33 is a combined plot of TGA and DSC analyses of Form J of ivosidenib.
Figure 34:
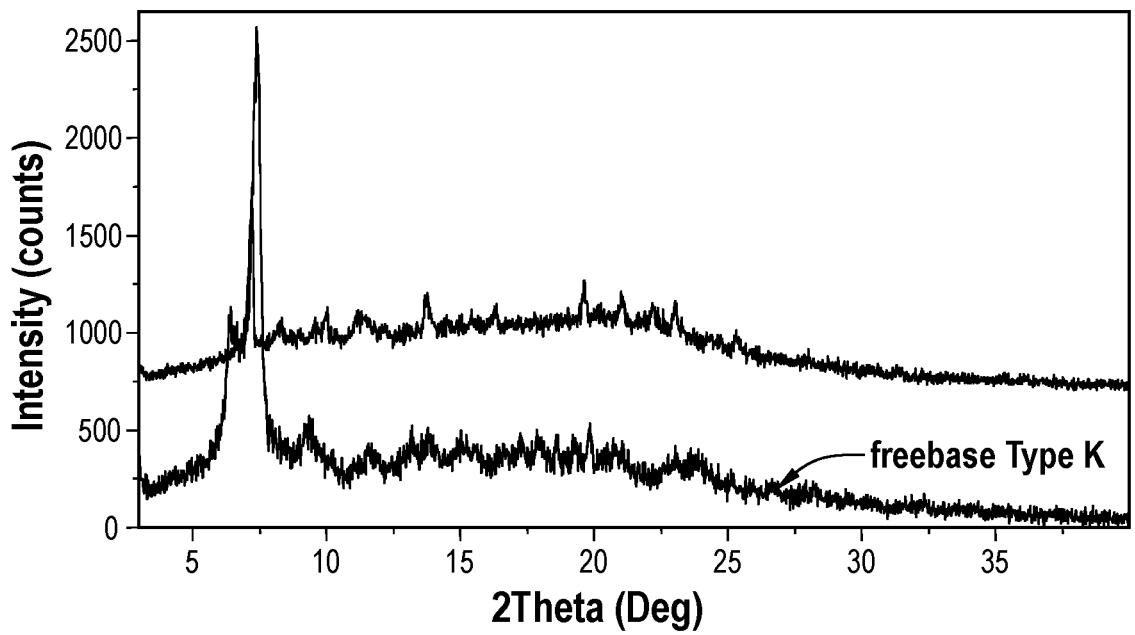
FIG. 34 is an XRPD diffractogram of Form K of ivosidenib.

The XRPD pattern of ivosidenib freebase Form J shown in FIG. 33 indicates that it is a crystalline form, which is different from freebase Form A. The DSC and TGA overlay of ivosidenib freebase Type J is displayed in FIG. 34. The TGA data shows ~15.3 wt % weight loss before 132.0° C. which is probably due to the existence of residual solvent. An endotherm was observed at 79.7° C. (onset) in DSC curve demonstrating that freebase Form J is a solvate or hydrate.

TABLE 17

XRPD peaks of Form J of ivosidenib

| Pos. [°2Th.] | Height [cts] | FWHM Left [°2Th.] | d-spacing [Å] | Rel. Int. [%] |
|---|---|---|---|---|
| 6.4 | 35.574370 | 0.802944 | 13.82161 | 7.21 |
| 8.2 | 181.636100 | 0.133824 | 10.76889 | 36.81 |
| 9.4 | 176.789900 | 0.100368 | 9.36099 | 35.83 |
| 10.3 | 123.932900 | 0.100368 | 8.60983 | 25.12 |
| 11.9 | 172.761300 | 0.100368 | 7.44210 | 35.01 |
| 13.2 | 79.875150 | 0.200736 | 6.72240 | 16.19 |
| 16.1 | 286.665700 | 0.100368 | 5.49963 | 58.10 |
| 16.8 | 137.992300 | 0.133824 | 5.29035 | 27.97 |
| 17.6 | 493.415200 | 0.083640 | 5.04965 | 100.00 |
| 18.6 | 114.006700 | 0.200736 | 4.76137 | 23.11 |
| 19.7 | 219.114300 | 0.200736 | 4.51583 | 44.41 |
| 21.4 | 219.063600 | 0.117096 | 4.15665 | 44.40 |
| 22.5 | 277.427700 | 0.200736 | 3.95958 | 56.23 |
| 23.2 | 192.926300 | 0.133824 | 3.82946 | 39.10 |
| 25.0 | 218.797700 | 0.133824 | 3.56786 | 44.34 |
| 26.0 | 115.162400 | 0.267648 | 3.42523 | 23.34 |
| 27.1 | 64.280120 | 0.200736 | 3.29216 | 13.03 |
| 29.6 | 38.778450 | 0.334560 | 3.01888 | 7.86 |
| 35.5 | 21.745430 | 0.401472 | 2.52854 | 4.41 |

Peaks were searched in X'Pert HighScore Plus (version 3.0) with the following parameters: minimum significance=2.0, minimum tip width=0.01 degree 2 theta, maximum tip width=1.00 degree 2 theta, peak base width=2.00 degrees 2 theta, method=minimum 2$^{nd}$ derivative.

Form K

Figure 35:
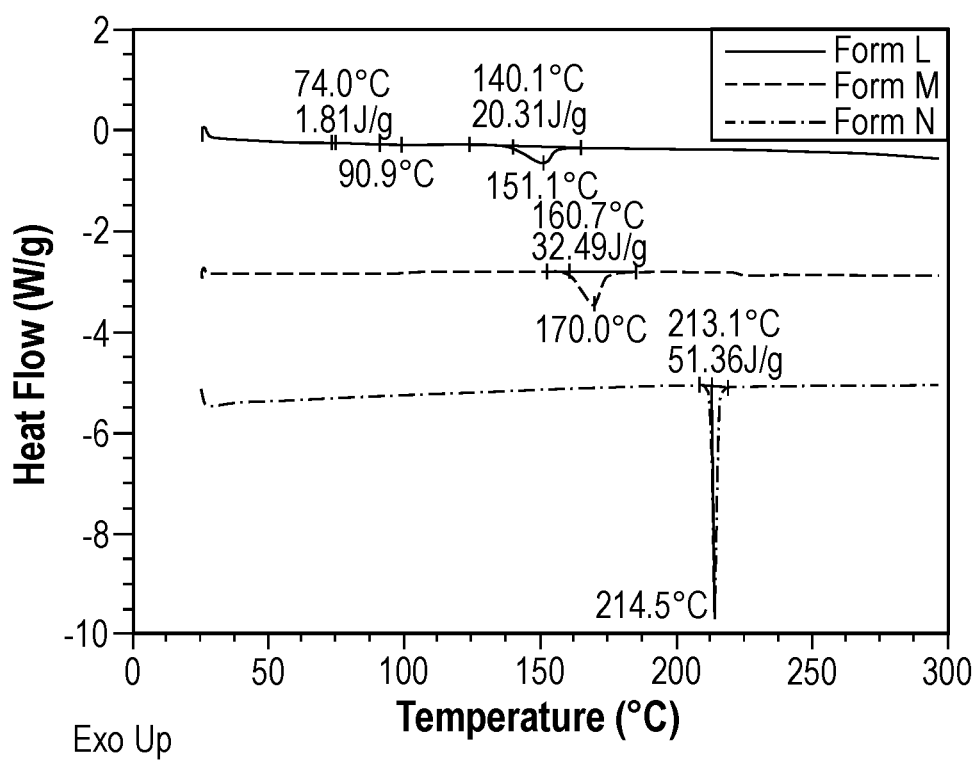
FIG. 35 is an overlay of DSC curves of Form L, Form M, and Form N showing the interconversion of these forms as described herein.

The XRPD pattern of ivosidenib freebase Form K is shown in FIG. 35 and indicates that it is a partially crystalline form.

Pattern 3

A solvate form of ivosidenib referred to as Pattern 3 is observed when a slurry of any of the anhydrous forms (that is, one or more of Form L, Form M, and Form N) in DCM convert to Pattern 3. However, upon drying under vacuum, Pattern 3 converts to Form L.

Interconversion of Forms of Ivosidenib

Figure 36:
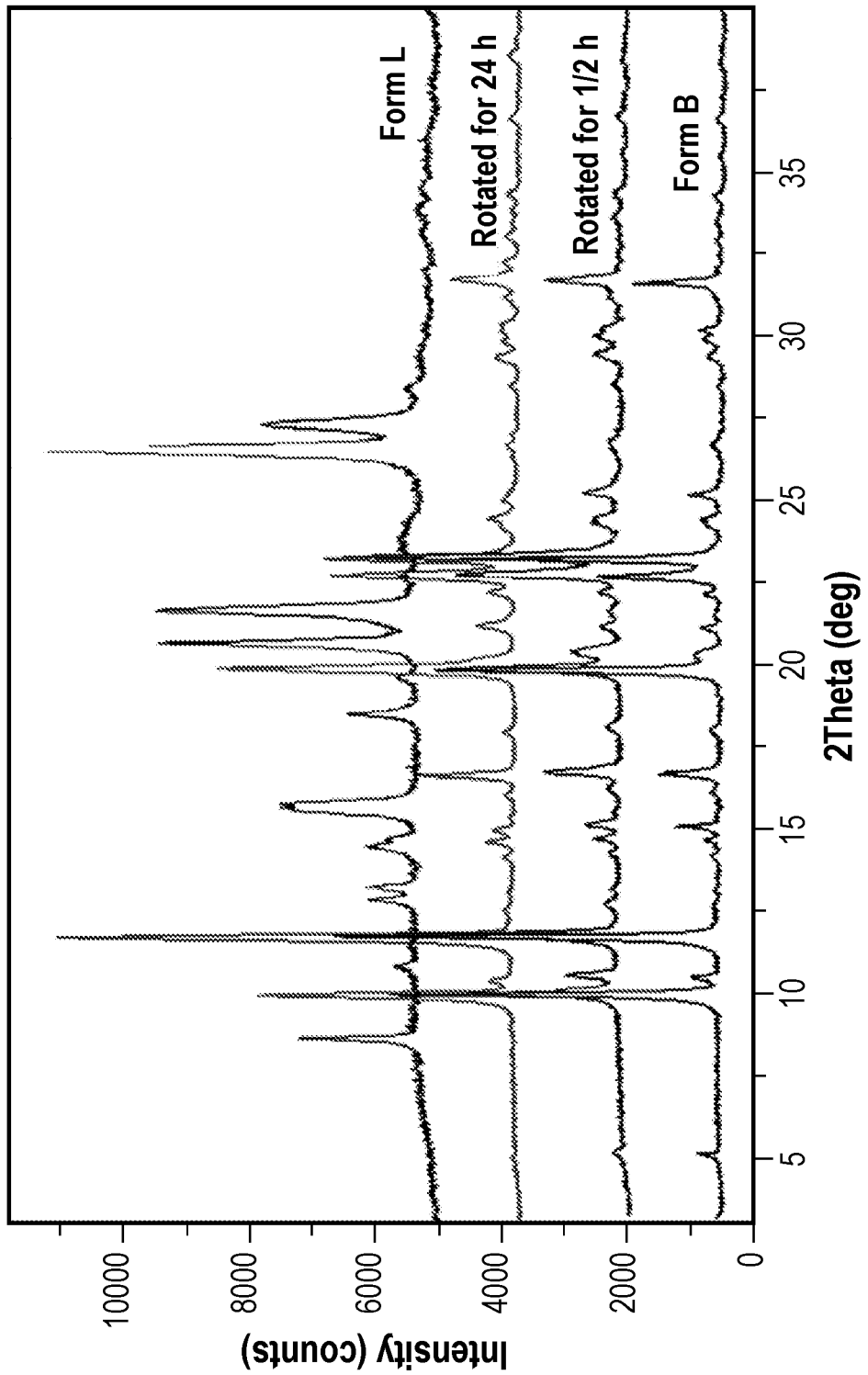
FIG. 36 is an illustration of the interconversion of Forms L and B of ivosidenib as described herein.

The polymorphs of ivosidenib can interconvert under certain conditions. For example, FIG. 36 shows an overlay of DSC curves of Form L, Form M, and Form N as described herein.

Mixtures of 1:1 anhydrate Forms L, M, and N were mixed with dichloromethane, and all studies resulted in the formation of the Form E solvate. This solvate when dried, produces Form L.

Figure 37:
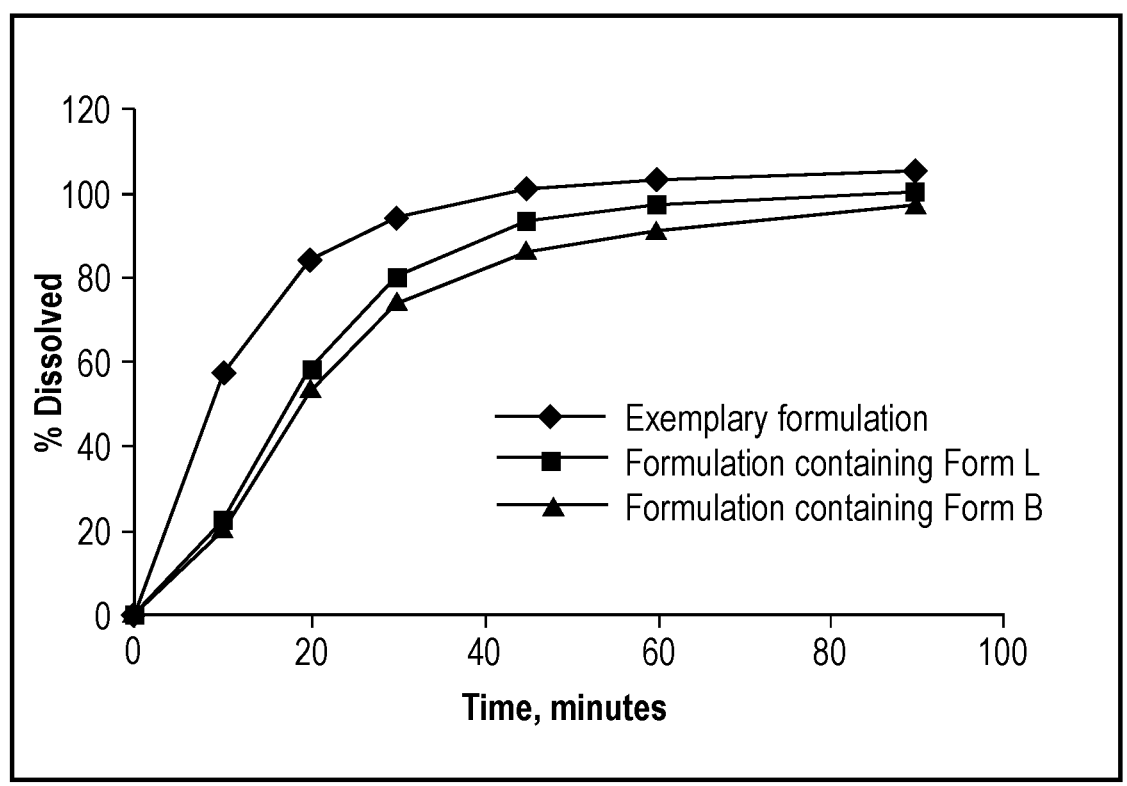
FIG. 37 is a graphical representation of dissolution profiles of tablets spiked with Form L and Form B of ivosidenib compared to the target formulation.

Form L, suspended and rotated in methanol at room temperature, converts to Form B as shown in FIG. 37. Form M and Form N when slurried in methanol also produce Form B. The solubility of Form M and N are ~110 mg/mL, well above the concentration of AG-120 in the SDI spray solution (~70 mg/mL).

Form B is a thermodynamically stable hydrate form. All other forms (such as Form A, Form C, Form D, Form E, Form F, Form G, Form H, Form I, Form J, Form K, and Form L can be converted to Form B when subjected to the conditions described above, namely, under the conditions listed under the heading "Form B." Form L is a thermodynamically stable form of ivosidenib when isolated from DCM, or a mixed solvent containing DCM and a hydrocarbon solvent. All other forms (that is, any of Form A, Form B, Form C, Form D, Form E, Form F, Form G, Form H, Form I, Form J, and Form K) may be made by crystallization in such a solution. Form L may also be obtained by drying Pattern 3. The present disclosure, therefore, includes a method of synthesis of Form B and of Form L via any one or more of the other identified forms of ivosidenib. As such, Form A, Form C, Form D, Form E, Form F, Form G, Form H, Form I, Form J, Form K, and Form L could be considered a synthetic intermediate of Form B, in that one or more of these forms may be used to convert to Form B. Similarly, Form A, Form B, Form C, Form D, Form E, Form F, Form G, Form H, Form I, Form J, and Form K could be considered a synthetic intermediate of Form L.

Crystallinity Experiments

Ivosidenib tablets may be manufactured using a spray-dried dispersion (50:50) intermediate of ivosidenib drug substance and at least one other additive, such as HPMCAS. The ivosidenib and HPMCAS may be dissolved completely in methanol before spray-drying. The ivosidenib spray-dried intermediate (SDI) may be consistently produced as an amorphous material, and may be used to manufacture final drug products, such as those used in clinical efficacy trials and registration stability tests.

In order to assess the impact of crystalline polymorphic forms on dissolution profiles, variant tablets were manufactured with SDI spiked with drug substance of two different crystalline polymorphs: Form B, and Form L, which forms are as described above. As used herein, the term "spiked" or "spiking" is used consistently with usage in the field of pharmaceutical manufacturing, namely the introduction of a particular form to the crystallization solution to encourage nucleation and growth. These forms were selected because it was determined that if an SDI should crystallize, these two forms would be most likely to be present. However, it is noted that the SDI can be reliably made in completely amorphous form, with no detectable crystalline form present even under stressed conditions.

250 mg tables were manufactured by adding 50 mg (20% w/w) of crystalline Form L or Form B with the ivosidenib SDI (therefore, amorphous SDI was present at 80% w/w as a measure of the active ingredient.)

In one example, such a tablet may be formulated as in Table 18:

TABLE 18

Spiking of formulations with crystalline ivosidenib

| INGREDIENT | FORMULATION SPIKED WITH | |
|---|---|---|
| | FORM B % w/w | FORM L % w/w |
| Intragranular | | |
| Ivosidenib HPMCAS | 48.0 | 48.0 |
| Ivosidenib Form B | 6.0 | 0.0 |
| Ivosidenib Form L | 0.0 | 6.0 |
| HPMCAS MG | 6.0 | 6.0 |
| Polymeric filler PH-103 | 21.5 | 21.5 |
| Disintegrant | 4.0 | 4.0 |
| Surfactant | 1.0 | 1.0 |
| Glidant | 1.0 | 1.0 |
| Lubricant | 0.5 | 0.5 |
| Extragranular | | |
| Polymeric filler | 8.0 | 8.0 |
| Disintegrant | 2.0 | 2.0 |
| Glidant | 1.0 | 1.0 |
| Lubricant | 1.0 | 1.0 |
| TOTAL | 100.0 | 100.0 |

To manufacture such a tablet, HPMCAS MG may be combined with the crystalline for of ivosidenib (that is, Form B or Form L) and combined with about half of the amorphous ivosidenib SDI, and mixed for about 1 minute at about 25 rpm. The remaining amorphous SDI can then be added to the blender and mixed for an additional minute at about 25 rpm. Microcrystalline cellulose PH-103 can then be added to the blend, and mixed for about 85 revolutions. The resulting pre-blend may be screened such as by using a Quadro comi 197S equipped with an 093R screen at about 1800±100 rpm. The screened pre-blend can then be blended with croscarmellose sodium, sodium lauryl sulfate NF and colloidal silicon dioxide for about 22 minutes and 50 seconds±10 seconds at about 25 rpm. The blend can be lubricated withe magnesium stearate for about 4 minutes at about 25 rpm.

The pre-blend can then be roller compacted and milled, such as by using a 1 mm screen. For example, one roller can be a smooth roller, and the other roller can be a knurled roller, with a roll compaction force of about 5.0 kilonewton per centimeter (kN/cm) with a roll gap of about 2.0 mm and a roll speed of about 2 rpm.

The compacted milled granules may be blended with extragranular excipients microcrystalline cellulose PH 103, colloidal silicon dioxide, and croscarmellose sodium for about 22 minutes followed by lubrication with magnesium stearate for 4 minutes at a speed of about 25 rpm to produce the final blend. The final blends can then be compressed in tablet form, such as to a tablet hardness of about 18±2 kilopascal (kP), or about 27±4 kP, or about 37±2 kP. The tablets may be optionally film coated to a target coating weight gain, such as a weight gain of about 5.0% w/w.

Dissolution profiles of tablets formulated as described above are presented in FIG. 38. Table 19 describes the dissolution of 250 mg tablets spiked with Form L ivosidenib in twelve individual vessels containing a solution at pH 6.8 and containing 0.6% SDS, referred to as Medium A; Table 20 lists the results of a similar trial for tablets spiked with Form B.

TABLE 19

Dissolution profile for ivosidenib tablets, 250 mg manufactured using polymorph Form L drug substance [pH 6.8 + 0.6% SDS]

| | % Dissolution | | | | | |
|---|---|---|---|---|---|---|
| Vessel | 10 min | 20 min | 30 min | 45 min | 60 min | 90 min |
| 1 | 24 | 57 | 80 | 92 | 97 | 100 |
| 2 | 13 | 45 | 69 | 86 | 94 | 100 |
| 3 | 26 | 69 | 86 | 95 | 98 | 100 |
| 4 | 28 | 67 | 84 | 93 | 96 | 97 |
| 5 | 20 | 55 | 80 | 93 | 98 | 101 |
| 6 | 24 | 60 | 81 | 93 | 97 | 100 |
| 7 | 19 | 54 | 78 | 92 | 97 | 99 |
| 8 | 23 | 60 | 82 | 94 | 99 | 101 |
| 9 | 22 | 60 | 83 | 95 | 99 | 101 |
| 10 | 22 | 57 | 81 | 94 | 98 | 101 |
| 11 | 24 | 63 | 83 | 94 | 98 | 100 |
| 12 | 19 | 54 | 79 | 93 | 98 | 101 |
| Mean | 22 | 58 | 80 | 93 | 97 | 100 |
| % RSD | 17.5 | 10.8 | 5.3 | 2.4 | 1.4 | 1.1 |

TABLE 20

Dissolution profile for ivosidenib tablets, 250 mg manufactured using polymorph Form B drug substance [pH 6.8 + 0.6% SDS]

| | % Dissolution | | | | | |
|---|---|---|---|---|---|---|
| Vessel | 10 min | 20 min | 30 min | 45 min | 60 min | 90 min |
| 1 | 15 | 49 | 72 | 84 | 90 | 98 |
| 2 | 16 | 43 | 67 | 85 | 91 | 100 |
| 3 | 17 | 49 | 73 | 86 | 92 | 99 |
| 4 | 25 | 63 | 78 | 86 | 90 | 94 |
| 5 | 21 | 52 | 73 | 85 | 90 | 96 |
| 6 | 24 | 57 | 75 | 86 | 91 | 96 |
| 7 | 25 | 59 | 77 | 88 | 93 | 97 |
| 8 | 20 | 52 | 75 | 88 | 93 | 98 |
| 9 | 22 | 61 | 78 | 88 | 92 | 97 |
| 10 | 17 | 46 | 70 | 86 | 92 | 99 |
| 11 | 25 | 61 | 78 | 87 | 92 | 97 |
| 12 | 17 | 46 | 71 | 85 | 91 | 98 |
| Mean | 20 | 53 | 74 | 86 | 91 | 97 |
| % RSD | 18.3 | 12.9 | 4.8 | 1.5 | 1.1 | 1.5 |

Similar dissolution studies were undertaken with Medium B (pH 6.8, 0.4% SDS). Similarity factors ($f_2$) were calculated to assess the dissolution profiles, compared to a target formulation. The similarity factors are included in Table 21.

TABLE 21

Similarity factor results for tablets containing polymorphs of ivosidenib

| Reference Condition | Test Condition | Similarity factor ($f_2$) result for dissolution medium A | Similarity factor ($f_2$) result for dissolution medium B |
|---|---|---|---|
| Target (nominal) formulation | Spiked with Form L | 28.9 | 48.5 |
| | Spiked with Form B | 26.0 | 43.1 |

As can be seen from the similarity factors listed above, Medium A demonstrates good discrimination between the target formulation and those that include the polymorphic variants. The calculated $f_2$ values (28.9 and 26.0, for Forms L and B, respectively) indicate that the profiles are dissimilar.

Medium B also demonstrates discrimination between the target formulation and those containing polymorphs, although not to as great a degree as Medium A ($f_2$ being 48.5 and 43.1 for Forms L and B, respectively.)

Impurities

In some embodiments, a formulation of ivosidenib may contain additional compounds, which may be considered impurities. In some embodiments these additional compounds may be degradation products of ivosidenib and may be formed under stress conditions, such as high temperature, light and/or humidity. In other embodiments, these additional compounds may be formed during the process of making ivosidenib In some embodiments, the formulation may include less than 0.5% w/w of any single additional compound, or less than 0.45% w/w, or less than 0.4% w/w, or less than 0.35% w/w, or less than 0.3% w/w, or less than 0.25% w/w, or less than 0.2% w/w, or less than 0.15% w/w, or less than 0.10% w/w, or less than 0.05% w/w, or less than 0.04% w/w, or less than 0.03% w.w, or less than 0.02% w/w, or less than 0.01% w/w.

Potential impurities are listed in Table 22 and may be formed during manufacturing or upon storage under stressed conditions of ivosidenib drug substance. All have all been considered for their potential genotoxicity using Derek Nexus and the Leadscope Model Applier. Additionally, all materials used in the synthesis of ivosidenib were included as part of the genotoxin assessment.

The intended patient population has relapsed/refractory acute myeloid leukemia and is expected to receive ivosidenib at a maximum total daily dose of 500 mg for duration of 1-10 years. The accepted Threshold of Toxicological Concern (TTC) limits based on recommendations in *ICH M7 Guideline: Assessment and control of DNA reactive (mutagenic) impurities in pharmaceuticals to limit potential carcinogenic risk*, are 10 μg per day per individual genotoxic impurity and 30 μg per day for total genotoxic impurities with the same mechanism of action for 1-10 years of dosing. This translates to the limits of 20 ppm for each individual genotoxic impurity and 60 ppm for all genotoxic impurities combined in the final drug substance.

Three potential impurities, benzene, benzaldehyde, and benzyl chloride are known mutagens. Phenol has inconclusive results in literature and is treated as a potential genotoxic impurity (PGI). Because of the benzyl chloride substructure in the molecules, both 2-chlorobenzyl chloride and 1-chloro-2-(dichloromethyl)benzene are treated conservatively as PGIs even though they are reported to be Ames-negative (ECHA, European Chemicals Agency, Registered substances).

All compounds that have structural alerts are negative in in vitro bacterial reverse mutation assays (Ames). Several analogs of (E)-1-(2-chlorophenyl)-N-(5-fluoropyridin-3-yl) methanimine formed from impurities in starting materials 3-amino-5-fluoropyridine and 2-chlorobenzaldehyde are not evaluated by Ames test because they have the same alerting structure (arylmethanimine) as (E)-1-(2-chlorophenyl)-N-(5-fluoropyridin-3-yl) methanimine that is negative in Ames test. They are treated as regular impurities (specified or unspecified).

Control of these genotoxic impurities may be achieved by a number of methods, including treating products with various reagents or solvents, or by using particular starting materials.

TABLE 22

| Impurity Compounds - Formulation | | |
|---|---|---|
| Impurity ID | IUPAC name | Structure |
| Impurity ID #1 | 2-((2S)-2-((1-(2-chlorophenyl)-2-((3,3-difluorocyclobutyl)amino)-2-oxoethyl)(5-fluoropyridin-3-yl)carbamoyl)-5-oxopyrrolidin-1-yl)isonicotinamide | |
| Impurity ID #2 | (S)-N-((S)-1-(2-chlorophenyl)-2-((3,3-difluorocyclobutyl)amino)-2-oxoethyl)-1-(4-cyanopyridin-2-yl)-5-oxo-N-(pyridin-3-yl)pyrrolidine-2-carboxamide | |

TABLE 22-continued

Impurity Compounds - Formulation

| Impurity ID | IUPAC name | Structure |
|---|---|---|
| Impurity #3 | (S)-N-((R)-1-(2-Chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide | 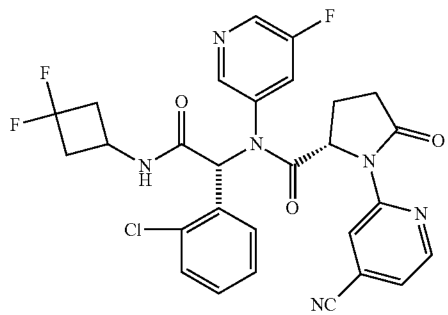 [SMILES: N#Cc1ccnc(N2C(=O)CC[C@H]2C(=O)N(c2cncc(F)c2)[C@@H](C(=O)NC2CC(F)(F)C2)c2ccccc2Cl)c1] |
| Impurity ID #4 | (R)-N-((S)-1-(2-Chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide | 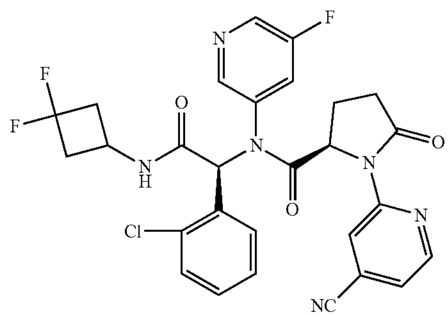 [SMILES: N#Cc1ccnc(N2C(=O)CC[C@@H]2C(=O)N(c2cncc(F)c2)[C@H](C(=O)NC2CC(F)(F)C2)c2ccccc2Cl)c1] |
| Impurity ID #5 | (R)-N-((R)-1-(2-Chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide | 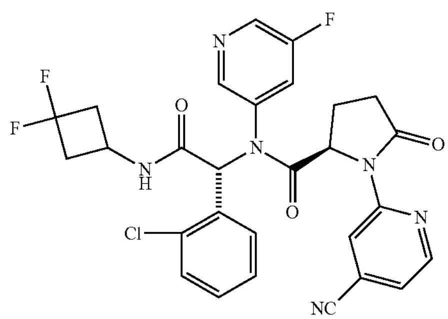 [SMILES: N#Cc1ccnc(N2C(=O)CC[C@@H]2C(=O)N(c2cncc(F)c2)[C@@H](C(=O)NC2CC(F)(F)C2)c2ccccc2Cl)c1] |
| Impurity ID #10 | 3-amino-5-fluoropyridine | 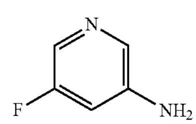 |
| Impurity ID #11 | 2-chloro-4-cyanopyridine | 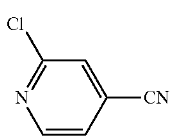 |
| Impurity ID #12 | (S)-N-((S)-1-(2-Chlorophenyl)-2-((3,3-difluorocyclobutyl)amino)-2-oxoethyl)-N-(5-fluoropyridin-3-yl)-5-oxopyrrolidine-2-carboxamide | 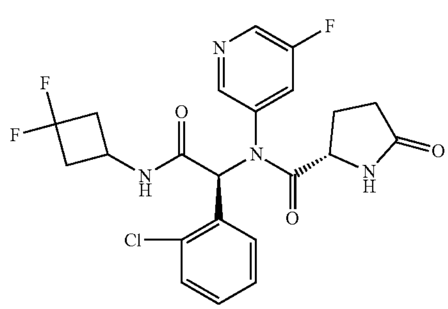 [SMILES: O=C1CC[C@@H](C(=O)N(c2cncc(F)c2)[C@H](C(=O)NC2CC(F)(F)C2)c2ccccc2Cl)N1] |

TABLE 22-continued

Impurity Compounds - Formulation

| Impurity ID | IUPAC name | Structure |
| --- | --- | --- |
| Impurity ID #14 | 2-(2-Chlorophenyl)-N-(3,3-difluorocyclobutyl)-2-((5-fluoropyridin-3-yl)amino)acetamide | 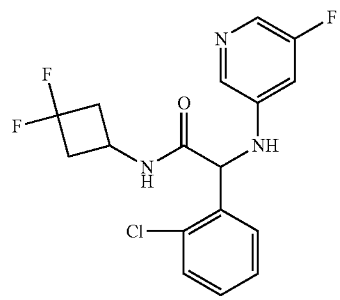 [SMILES: O=C(NC1CC(F)(F)C1)C(Nc1cncc(F)c1)c1ccccc1Cl] |
| Impurity ID #16 | (S)-5-(((S)-1-(2-Chlorophenyl)-2-((3,3-difluorocyclobutyl)amino)-2-oxoethyl)(5-fluoropyridin-3-yl)amino)-4-((4-cyanopyridin-2-yl)amino)-5-oxopentanoic acid | 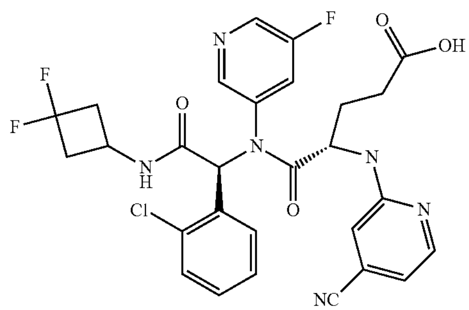 [SMILES: N#Cc1ccnc(N[C@@H](CCC(=O)O)C(=O)N(c2cncc(F)c2)[C@H](C(=O)NC2CC(F)(F)C2)c2ccccc2Cl)c1] |
| Impurity ID #17 | (S)-4-(bis(4-cyanopyridin-2-yl)amino)-5-(((S)-1-(2-chlorophenyl)-2-((3,3-difluorocyclobutyl)amino)-2-oxoethyl)(5-fluoropyridin-3-yl)amino)-5-oxopentanoic acid | 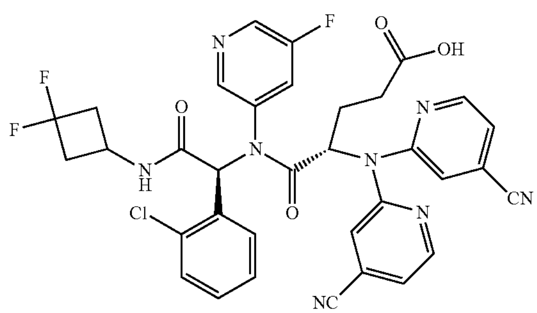 [SMILES: N#Cc1ccnc(N(c2cc(C#N)ccn2)[C@@H](CCC(=O)O)C(=O)N(c2cncc(F)c2)[C@H](C(=O)NC2CC(F)(F)C2)c2ccccc2Cl)c1] |
| Impurity ID #18 | (S)-2-(2-Chlorophenyl)-2-((5-((4-cyanopyridin-2-yl)amino)-2-oxo-3,4-dihydro-2H-pyran-6-yl)(5-fluoropyridin-3-yl)amino)-N-(3,3-difluorocyclobutyl)acetamide | 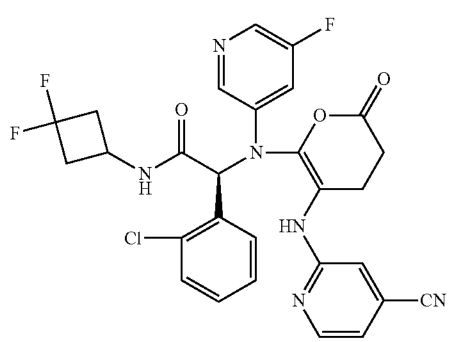 [SMILES: N#Cc1ccnc(NC2=C(N(c3cncc(F)c3)[C@H](C(=O)NC3CC(F)(F)C3)c3ccccc3Cl)OC(=O)CC2)c1] |

TABLE 22-continued

Impurity Compounds - Formulation

| Impurity ID | IUPAC name | Structure |
|---|---|---|
| Impurity ID #19 (Cl/N syn/anti) | (2S)-N-((1S)-2-((2-chloro-3,3-difluorocyclobutyl) amino)-1-(2-chlorophenyl)-2-oxoethyl)-1-(4-cyanopyridin-2-yl)-N-(5-fluoropyridin-3-yl)-5-oxopyrrolidine-2-carboxamide | 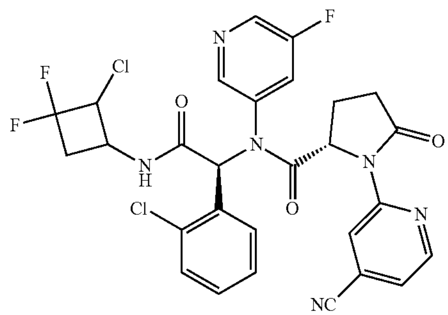 [SMILES: N#Cc1ccnc(N2C(=O)CC[C@H]2C(=O)N(c2cncc(F)c2)[C@H](C(=O)NC2CC(F)(F)C2Cl)c2ccccc2Cl)c1] |
| Impurity ID #20 | (S)-1-(4-Cyanopyridin-2-yl)-N-((S)-1-(2,4-dichlorophenyl)-2-((3,3-difluorocyclobutyl) amino)-2-oxoethyl)-N-(5-fluoropyridin-3-yl)-5-oxopyrrolidine-2-carboxamide | 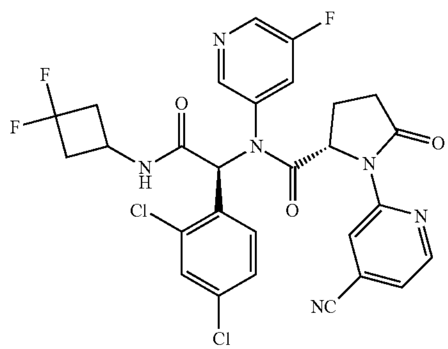 [SMILES: N#Cc1ccnc(N2C(=O)CC[C@H]2C(=O)N(c2cncc(F)c2)[C@H](C(=O)NC2CC(F)(F)C2)c2ccc(Cl)cc2Cl)c1] |
| Impurity ID #21 | (S)-1-(4-Cyanopyridin-2-yl)-N-((S)-1-(2,3-dichlorophenyl)-2-((3,3-difluorocyclobutyl) amino)-2-oxoethyl)-N-(5-fluoropyridin-3-yl)-5-oxopyrrolidine-2-carboxamide | 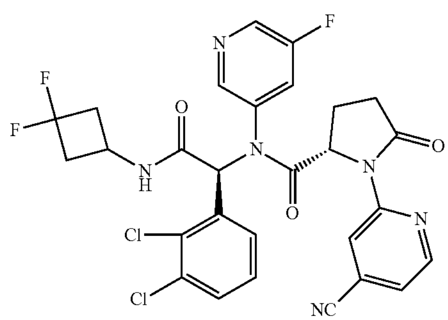 [SMILES: N#Cc1ccnc(N2C(=O)CC[C@H]2C(=O)N(c2cncc(F)c2)[C@H](C(=O)NC2CC(F)(F)C2)c2cccc(Cl)c2Cl)c1] |
| Impurity ID #22 | (S)-N-((S)-1-(4-Chlorophenyl)-2-((3,3-difluorocyclobutyl) amino)-2-oxoethyl)-1-(4-cyanopyridin-2-yl)-N-(5-fluoropyridin-3-yl)-5-oxopyrrolidine-2-carboxamide | 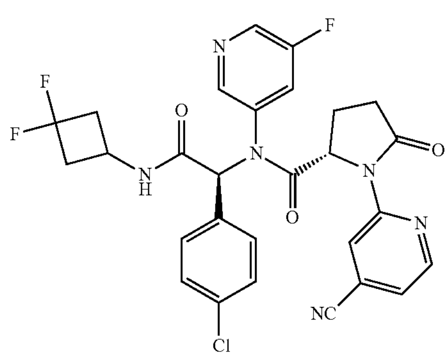 [SMILES: N#Cc1ccnc(N2C(=O)CC[C@H]2C(=O)N(c2cncc(F)c2)[C@H](C(=O)NC2CC(F)(F)C2)c2ccc(Cl)cc2)c1] |

TABLE 22-continued

Impurity Compounds - Formulation

| Impurity ID | IUPAC name | Structure |
|---|---|---|
| Impurity ID #23, 24 | 3-((2S)-1-(4-carbamoylpyridin-2-yl)-N-(1-(2-chlorophenyl)-2-((3,3-difluorocyclobutyl)amino)-2-oxoethyl)-5-oxopyrrolidine-2-carboxamido)-5-fluoropyridine 1-oxide | 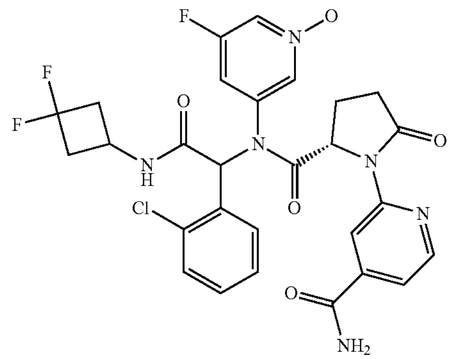 |
| | 4-carbamoyl-2-((2S)-2-((1-(2-chlorophenyl)-2-((3,3-difluorocyclobutyl)amino)-2-oxoethyl)(5-fluoropyridin-3-yl)carbamoyl)-5-oxopyrrolidin-1-yl)pyridine 1-oxide | |
| Impurity ID #25 | (S)-1-(4-Cyanopyridin-2-yl)-N-((S)-1-(3,3-difluorocyclobutyl)-2-oxoindolin-3-yl)-N-(5-fluoropyridin-3-yl)-5-oxopyrrolidine-2-carboxamide | 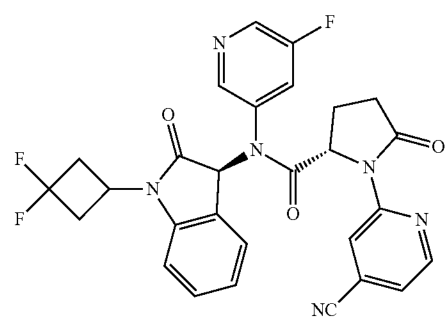 [SMILES: N#Cc1ccnc(N2C(=O)CC[C@H]2C(=O)N(c2cncc(F)c2)[C@@H]2C(=O)N(C3CC(F)(F)C3)c3ccccc32)c1] |

Elemental Impurities of Ivosidenib Formulations

Elemental impurities are controlled in the final formulation of ivosidenib. Among the metals controlled in this way are palladium, molybdenum, cadmium, lead, arsenic, mercury, cobalt, vanadium, and nickel.

Residual Solvents Ivosidenib—Formulations

Residual solvents are controlled in the final formulation of ivosidenib. Among the metals controlled in this way are isopropyl acetate, n-heptane, dichloromethane, benzene, heptane, ethyl formate, methanol, isopropyl alcohol, and ethyl acetate.

Drug Product Intermediates including Solid Dispersions

Provided are compositions, comprising a drug product intermediate containing ivosidenib, or a pharmaceutically acceptable salt thereof, comprising at least one solid state form of ivosidenib, or a plurality of solid state forms of ivosidenib. In some embodiments the drug product intermediate may optionally contain amorphous ivosidenib. In some instances, the compositions may include a second molecule as listed herein. In some embodiments, the drug product intermediate comprising ivosidenib may be a solid dispersion comprising ivosidenib or a pharmaceutically acceptable salt thereof, and one or more polymer(s). In some embodiments, the solid dispersion comprises ivosidenib, or a pharmaceutically acceptable salt thereof, one or more polymer(s), and one or more surfactant(s). In some embodiments, the solid dispersion comprises ivosidenib or any form thereof, or a pharmaceutically acceptable salt thereof, and one polymer. In some embodiments, the solid dispersion comprises ivosidenib or any form thereof, or a pharmaceutically acceptable salt thereof, one polymer, and a surfactant.

The solid dispersions provided herein, are formed using one or more forms of ivosidenib, enhance the solubility of ivosidenib relative to a neat form of ivosidenib (e.g., Form L or Form B), and thus provide improved exposure upon oral dosing of the solid dispersion to a subject. In one embodiment, the solid dispersion comprises ivosidenib or any form thereof, or a pharmaceutically acceptable salt thereof, one or more polymer(s), and optionally one or more solubility enhancing surfactant.

In some embodiments, at least a portion of the ivosidenib in the solid dispersion is in the amorphous state (e.g., at least about 50%, at least about 55%, at least about 60%, at least about 65%, at least about 70%, at least about 75%, at least about 80%, at least about 85%, at least about 90%, at least about 95%, at least about 98%, or at least about 99%). In other embodiments, the solid dispersion is substantially free of crystalline ivosidenib, or a pharmaceutically acceptable salt thereof. In some embodiments, more than one polymorph of ivosidenib may be present. In some embodiments, a second form, including a crystalline form, may be present.

In some embodiments, the solid dispersion is an amorphous solid (e.g. spray dried) dispersion comprising ivosidenib, in any form, and a polymer. The amorphous solid dispersion can include, e.g., less than about 30%, less than about 20%, less than about 15%, less than about 10%, less than about 5%, less than about 4%, less than about 3%, less than about 2%, or less than about 1% of a crystalline form of ivosidenib, e.g., be substantially free of crystalline ivosidenib, or a pharmaceutically acceptable salt thereof. In some embodiments, the amorphous solid dispersion may include more than one crystalline form of ivosidenib. In some embodiments, a second molecule may be present.

In one embodiment, the solid dispersion exhibits a predetermined level of physical and/or chemical stability. For example, the solid dispersion retains about 50%, about 60%, about 70%, about 80%, about 90%, about 95%, about 98%, or about 99%, of amorphous ivosidenib, or a pharmaceutically acceptable salt thereof, when stored at 25° C. in a closed water tight container, for example, an amber glass vial, high density polyethylene (HDPE) container or double polyethylene bags with twisted nylon tie placed in an HDPE container with desiccant.

In some embodiments, the polymer increases the chemical or physical stability (for example, as measured by a Modulated Differential Scanning calorimeter) of ivosidenib in any form thereof, or a pharmaceutically acceptable salt thereof, when stored (for example, at 2-8° C., or at or around 4° C., or at room temperature) by at least about 10% (for example, by at least about 20%, by at least about 30%, by at least about 40%, by at least about 50%, by at least about 60%, by at least about 70%, by at least about 80%, or by at least about 90%) compared to amorphous ivosidenib in any form, or a pharmaceutically acceptable salt thereof, without being in the presence of the polymer.

A solid dispersion generally exhibits a glass transition temperature, where the dispersion makes a transition from a glassy solid to a rubbery composition. In general, the higher the glass transition temperature, the greater the physical stability of the dispersion. The existence of a glass transition temperature generally indicates that at least a large portion of the composition (e.g., dispersion) is in an amorphous state. The glass transition temperature (Tg) of a solid dispersion suitable for pharmaceutical applications is generally at least about 50° C. In some embodiments, higher temperatures are preferred. Therefore, in some embodiments, a solid dispersion disclosed herein has a Tg of at least about 100° C. (e.g., at least about 100° C., at least about 105° C., at least about 110° C., at least about 115° C., at least about 120° C., at least about 125° C., at least about 130° C., at least about 135° C., at least about 140° C., at least about 150° C., at least about 160° C., at least about 170° C., at least about 175° C., at least about 180° C., or at least about 190° C.). In some embodiments, the Tg is up to about 200° C. In some embodiments, the Tg is up to about 130° C. (e.g., at least about 110° C., at least about 111° C., at least about 112° C., at least about 113° C., at least about 114° C., at least about 115° C., at least about 116° C., at least about 117° C., at least about 118° C., at least about 119° C., at least about 120° C., at least about 121° C., at least about 122° C., at least about 123° C., at least about 124° C., at least about 125° C., at least about 1216° C., at least about 127° C., at least about 128° C., at least about 129° C., or at least about 130° C.). Unless otherwise noted, the glass transition temperatures disclosed herein are measured under dry conditions.

In some embodiments the solid dispersion has a higher glass transition temperature than the glass transition temperature of amorphous ivosidenib in any form, or a pharmaceutically acceptable salt thereof, without being in the presence of the polymer(s). In some embodiments, the solid dispersion has a relaxation rate that is lower than the relaxation rate of amorphous ivosidenib in any form, or a pharmaceutically acceptable salt thereof, without being in the presence of the polymer(s).

Examples of polymers in the solid dispersion include cellulose derivatives (e.g., hydroxypropylmethylcellulose also known as hypromellose, (HPMC), hydroxypropylmethylcellulose phthalate, also known as hypromellose phthalate (HPMCP), hydroxypropylmethylcellulose acetate succinate, also known as hypromellose acetate succinate, (HPMCAS), hydroxypropylcellulose (HPC)), ethylcellulose, or cellulose acetate phthalate; polyvinylpyrrolidones (PVP); polyethylene glycols (PEG); polyvinyl alcohols (PVA); polyvinyl esters, such as Polyvinyl Acetate Phthalate (PVAP); acrylates, such as polymethacrylate (e.g., Eudragit® E); cyclodextrins (e.g., .beta.-cyclodextrin); Poly (D, L-lactide) (PLA), Poly (D,L-lactide, co-glycolide acid (PLGA); and copolymers and derivatives thereof, including for example polyvinylpyrollidone-vinyl acetate (PVP-VA), Polyvinyl caprolactam-polyvinyl, and acetate-polyethyleneglycol copolymer, Methylacrylate/methacrylic acid copolymer; Soluplus; Copovidone; and mixtures thereof.

In some embodiments, the solid dispersion includes one water-soluble polymer. In some embodiments, the solid dispersion includes one partially water-soluble polymer. In some embodiments, the polymer is a cellulose polymer.

In some embodiments, the polymer is HPMCAS (e.g., HPMCAS of different grades: HPMCAS-M, HPMCAS-MG or HPMCAS-HG). In some embodiments, the polymer is PVAP. In some embodiments, the polymer is HPMC (e.g., HPMC of different grades: HMPC60SH50, HPMCE50 or HPMCE15). In some embodiments, the polymer is HPMCP (e.g., HPMCP of different grades: e.g., HMPCP-HP55).

In some embodiments, the polymer is a pH-dependent enteric polymer. Such pH-dependent enteric polymers include, but are not limited to, cellulose derivatives (e.g., cellulose acetate phthalate (CAP)), HPMCP, HPMCAS, carboxymethylcellulose (CMC) or a salt thereof (e.g., a sodium salt such as (CMC-Na)); cellulose acetate trimellitate (CAT), hydroxypropylcellulose acetate phthalate (HP-CAP), hydroxypropylmethyl-cellulose acetate phthalate (HPMCAP), and methylcellulose acetate phthalate (MCAP), polymethacrylates (e.g., Eudragit S), or mixtures thereof.

In some embodiments, the polymer is hydroxypropylmethylcellulose acetate succinate, also known as hypromellose acetate succinate, (HPMCAS), e.g., HMPCAS-HG.

In another embodiment, the polymer(s) is an insoluble cross-linked polymer, for example a polyvinylpyrrolidone (e.g., Crospovidone). In another embodiment, the polymer(s) is polyvinylpyrrolidone (PVP).

In some embodiments, the one or more polymer(s) is present in the solid dispersion in an amount of between about 10% w/w and 90% w/w (e.g., between about 20% w/w and about 80% w/w; between about 30% w/w and about 70% w/w; between about 40% w/w and about 60% w/w; or between about 15% w/w and about 35% w/w). In some embodiments, the polymer(s) is present in the solid dispersion in an amount of from about 10% w/w to about 80% w/w, for example from about 30% w/w to about 75% w/w, or from about 40% w/w to about 65% w/w, or from about 45% w/w to about 55% w/w, for example, about 46% w/w, about 47% w/w, about 48% w/w, about 49% w/w, about 50% w/w, about 51% w/w, about 52% w/w, about 53% w/w, or about 54% w/w. In some embodiments, the polymer(s) is present in the solid dispersion in an amount of about 48% w/w, about 48.5% w/w, about 49% w/w, about 49.5% w/w, about 50% w/w, about 50.5% w/w, about 51% w/w, about 51.5% w/w, about 52% w/w, or about 52.5% w/w.

In some embodiments, the polymer(s) is present in the solid dispersion in an amount of from about 30% w/w to about 70% w/w. In some embodiments, the polymer(s) is present in the solid dispersion in an amount of from about 35% w/w to about 65% w/w. In some embodiments, the polymer(s) is present in the solid dispersion in an amount of from about 40% w/w to about 60% w/w. In some embodiments, the polymer(s) is present in the solid dispersion in an amount of from about 45% w/w to about 55% w/w. In some embodiments, the polymer(s) is present in the solid dispersion in an amount of about 50% w/w.

In some embodiments, ivosidenib in any form, or a pharmaceutically acceptable salt thereof, is present in the solid dispersion in an amount of from about 10% w/w and 90% w/w (e.g., between about 20% w/w and about 80% w/w; between about 30% w/w and about 70% w/w; between about 40% w/w and about 60% w/w; or between about 15% w/w and about 35% w/w). In some embodiments, ivosidenib in any form, or a pharmaceutically acceptable salt thereof, is present in the solid dispersion in an amount of from about 10% w/w to about 80% w/w, for example from about 30% w/w to about 75% w/w, or from about 40% w/w to about 65% w/w, or from about 45% w/w to about 55% w/w, for example, about 46% w/w, about 47% w/w, about 48% w/w, about 49% w/w, about 50% w/w, about 51% w/w, about 52% w/w, about 53% w/w, or about 54% w/w. In some embodiments, ivosidenib in any form, or a pharmaceutically acceptable salt thereof, is present in the solid dispersion in an amount of about 48% w/w, about 48.5% w/w, about 49% w/w, about 49.5% w/w, about 50% w/w, about 50.5% w/w, about 51% w/w, about 51.5% w/w, about 52% w/w, or about 52.5% w/w. In some embodiments, more than one polymorph of ivosidenib may be present. In some embodiments, a second molecule may be present.

In some embodiments, ivosidenib in any solid state form, or a pharmaceutically acceptable salt thereof, is present in the solid dispersion in an amount of from about 30% w/w to about 70% w/w. In some embodiments, ivosidenib in any solid state form, or a pharmaceutically acceptable salt thereof, is present in the solid dispersion in an amount of from about 35% w/w to about 65% w/w. In some embodiments, ivosidenib in any solid state form, or a pharmaceutically acceptable salt thereof, is present in the solid dispersion in an amount of from about 40% w/w to about 60% w/w. In some embodiments, ivosidenib in any solid state form, or a pharmaceutically acceptable salt thereof, is present in the solid dispersion in an amount of from about 45% w/w to about 55% w/w. In some embodiments, ivosidenib in any solid state form, or a pharmaceutically acceptable salt thereof, is present in the solid dispersion in an amount of about 50% w/w.

In another embodiment, the solid dispersion includes about 20% w/w to about 80% w/w ivosidenib in any solid state form, or a pharmaceutically acceptable salt thereof, and about 20% w/w to about 80% of polymer(s). In another embodiment, the solid dispersion includes about 25% w/w to about 75% w/w ivosidenib in any solid state form, or a pharmaceutically acceptable salt thereof, and about 25% w/w to about 75% of polymer(s). In another embodiment, the solid dispersion includes about 30% w/w to about 70% w/w ivosidenib in any solid state form, or a pharmaceutically acceptable salt thereof, and about 30% w/w to about 70% of polymer(s). In another embodiment, the solid dispersion includes about 35% w/w to about 65% w/w ivosidenib in any solid state form, or a pharmaceutically acceptable salt thereof, and about 35% w/w to about 65% of polymer(s). In another embodiment, the solid dispersion includes about 40% w/w to about 60% w/w ivosidenib in any solid state form, or a pharmaceutically acceptable salt thereof, and about 40% w/w to about 60% of polymer(s). In another embodiment, the solid dispersion includes about 45% w/w to about 55% w/w ivosidenib in any solid state form, or a pharmaceutically acceptable salt thereof, and about 45% w/w to about 55% of polymer(s). In another embodiment, the solid dispersion includes about 50% w/w ivosidenib in any solid state form, or a pharmaceutically acceptable salt thereof, and about 50% w/w of polymer(s). In some embodiments, more than one polymorph of ivosidenib may be present. In some embodiments, a second molecule may be present.

In another embodiment, the solid dispersion includes about 45% w/w to about 55% w/w ivosidenib in any solid state form, or a pharmaceutically acceptable salt thereof, and about 45% w/w to about 55% w/w HPMCAS (e.g., HPMCAS-MG or HPMCAS-HG, or other grades such as LF, MF, HF, or LG) or PVAP. In another embodiment, the solid dispersion includes about 50% w/w ivosidenib in any solid state form, or a pharmaceutically acceptable salt thereof, and about 50% w/w of HPMCAS.

In some embodiments, the solid dispersion also includes a surfactant or inert pharmaceutically acceptable substance. Examples of surfactants in the solid dispersion include sodium lauryl sulfate (SLS), vitamin E or a derivative thereof (e.g., vitamin E TPGS), Docusate Sodium, sodium dodecyl sulfate, polysorbates (such as Tween 20 and Tween 80), poloxamers (such as Poloxamer 335 and Poloxamer 407), glyceryl monooleate, Span 65, Span 25, Capryol 90, pluronic copolymers (e.g., Pluronic F108, Pluronic P-123), and mixtures thereof. In some embodiments, the surfactant is SLS. In some embodiments, the surfactant is vitamin E or a derivative thereof (e.g., vitamin E TPGS).

In some embodiments, the surfactant is present in the solid dispersion in an amount of from about 0.1% w/w to about 10% w/w, for example from about 0.5% w/w to about 2% w/w, or from about 1% w/w to about 3% w/w, from about 1% w/w to about 4% w/w, or from about 1% w/w to about 5% w/w. In some embodiments, the surfactant is present in the solid dispersion in an amount of about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, or about 1% w/w. In some embodiments, the surfactant is present in the solid dispersion in an amount of about 0.5% w/w, about 1% w/w, about 1.5% w/w, about 2% w/w, about 2.5% w/w, about 3% w/w, about 3.5% w/w, about 4% w/w, about 4.5% w/w, or about 5% w/w.

Processes for Preparing Solid Dispersions

In some embodiments, the solid dispersion may be prepared according to a process described herein. In general, methods that could be used include those that involve rapid removal of solvent or solvent mixture from a mixture or cooling a molten sample. Such methods include, but are not limited to, rotational evaporation, freeze-drying (i.e., lyophilization), vacuum drying, melt congealing, and melt extrusion. One embodiment of this disclosure involves solid dispersion obtained by spray-drying. In one embodiment, the product obtained by spray drying is dried to remove the solvent or solvent mixture.

Preparations disclosed herein, e.g., a pharmaceutical composition, can be obtained by spray-drying a mixture comprising ivosidenib in any form, or a pharmaceutically acceptable salt thereof, one or more polymer(s), and an appropriate solvent or solvent mixture. Spray drying involves atomization of a liquid mixture containing, e.g., a solid and a solvent or solvent mixture, and removal of the solvent or solvent mixture. The solvent or solvent mixture can also contain a nonvolatile solvent, such as glacial acetic acid. Atomization may be done, for example, through a two-fluid or pressure or electrosonic nozzle or on a rotating disk.

Spray drying converts a liquid feed to a dried particulate form. Spray drying generally involves the atomization of a liquid feed solution into a spray of droplets and contacting the droplets with hot air or gas in a drying chamber. The sprays are generally produced by either rotary (wheel) or nozzle atomizers. Evaporation of moisture from the droplets and formation of dry particles proceed under controlled temperature and airflow conditions.

Optionally, a secondary drying process such as fluidized bed drying or vacuum drying may be used to reduce residual solvents (and other additives, such as glacial acetic acid) to pharmaceutically acceptable levels. Typically, spray-drying involves contacting a highly dispersed liquid suspension or solution (e.g., atomized solution), and a sufficient volume of hot air or gas (e.g., nitrogen, e.g., pure nitrogen) to produce evaporation and drying of the liquid droplets. The preparation to be spray dried can be any solution, coarse suspension, slurry, colloidal dispersion, or paste that may be atomized using the selected spray-drying apparatus. In a standard procedure, the preparation is sprayed into a current of warm filtered air (or into gas, e.g., nitrogen) that evaporates the solvent and conveys the dried product to a collector (e.g., a cyclone). The spent air or gas is then exhausted with the solvent (or solvent mixture including any additives such as glacial acetic acid), (e.g., then filtered) or alternatively the spent air or gas is sent to a condenser to capture and potentially recycle the solvent or solvent mixture. For example, if a gas (e.g., nitrogen) is used, the gas is then optionally recycled, heated again and returned to the unit in a closed loop system. Commercially available types of apparatus may be used to conduct the spray-drying. For example, commercial spray dryers are manufactured by Buchi Ltd. and Niro (e.g., the PSD line of spray driers manufactured by Niro).

Spray-drying typically employs solids loads of material from about 1% to about 30% or up to about 50% (i.e., therapeutically active compound plus and excipients), preferably at least about 10%. In some embodiments, solids loads of less than 10% may result in poor yields and unacceptably long run-times. In general, the upper limit of solids loads is governed by the viscosity of (e.g., the ability to pump) the resulting solution and the solubility of the components in the solution. Generally, the viscosity of the solution can determine the size of the particle in the resulting powder product.

Techniques and methods for spray-drying may be found in Perry's Chemical Engineering Handbook, 6th Ed., R. H. Perry, D. W. Green & J. O. Maloney, eds., McGraw-Hill Book Co. (1984); and Marshall "Atomization and Spray-Drying" 50, Chem. Eng. Prog. Monogr. Series 2 (1954). In general, the spray-drying is conducted with an inlet temperature of from about 40° C. to about 200° C., for example, from about 70° C. to about 150° C., preferably from about 40° C. to about 60° C., about 50° C. to about 55° C., or about 80° C. to about 110° C., e.g., about 90° C. The spray-drying is generally conducted with an outlet temperature of from about 20° C. to about 100° C., for example from about 25° C. to about 30° C. (e.g., about 26° C.), about 40° C. to about 50° C., about 50° C. to about 65° C., e.g., about 56° C. to about 58° C.

Removal of the solvent or solvent mixture may require a subsequent drying step, such as tray drying, fluid bed drying (e.g., from about room temperature to about 100° C.), vacuum drying, microwave drying, rotary drum drying or biconical vacuum drying (e.g., from about room temperature to about 200° C.).

In one embodiment, the spray-drying is fluidized spray drying (FSD). The steps in FSD can include, for example: preparing a liquid feed solution (e.g., containing ivosidenib in any form or a pharmaceutically acceptable salt thereof, and optionally a polymer(s) and/or surfactant(s), dissolved or suspended in solvent(s)); atomizing (e.g., with a pressure nozzle, a rotary atomizer or disk, two-fluid nozzle or other atomizing methods) the feed solution upon delivery into the drying chamber of a spray dryer, e.g., operating in FSD mode; drying the feed solution in the drying chamber with heated air or a heated gas (e.g., nitrogen) to obtain a product, wherein larger particles of product separate out, e.g., drop out, while fines are carried by a stream of air or gas up to the top of the drying chamber (e.g., by natural convection) and to a cyclone, and re-introducing (e.g., at the top of the drying chamber or axially to the middle of the chamber) the fines into the drying chamber, wherein the re-introduced fines can agglomerate with newly formed product to generate an agglomerated product, wherein if the agglomerated product is large enough, it will separate out, if it is not large enough to separate out, the agglomerated product will be carried by convection to the top of the chamber and to the cyclone and re-introduced into the chamber. This process repeats until an agglomerated product that is large enough to drop out is formed. The fines can be re-introduced from the cyclone to the drying chamber via a feed pipe.

In some embodiments, rather than drying the feed solution with heated air or a heated gas, the feed solution can instead be spray congealed, e.g., the chamber is at room temperature (e.g., 21±4° C.) or is cooled, e.g., cooled gas (e.g., nitrogen) is used for the process.

FSD can further include collecting the agglomerated product in a first fluidizing chamber, which can be followed by discharging the agglomerated product from the first fluidizing chamber to a second fluidizing chamber, wherein a post-drying process can occur.

The agglomerated product (e.g., that separates out in the drying chamber) can then be transferred from the second fluidizing chamber to a third fluidizing chamber, where the agglomerated product is cooled. The agglomerated product (e.g., a solid dispersion of an amorphous compound) can then be further processed. For example, the product can be directly compressed. The product can optionally be blended with a surfactant, excipient, or pharmaceutically acceptable carrier, e.g., prior to direct compression. The product can optionally be further processed, e.g., milled, granulated, blended, and/or mixed with a melt granulate, surfactant, excipient, and/or pharmaceutically acceptable carrier.

FSD can be performed in a commercial spray dryer operating in fluidized spray dryer mode (FSD mode). FSD can be accomplished in either open cycle mode or closed cycle mode (e.g., the drying gas, e.g., nitrogen, is recycled). Examples of suitable spray dryers for use in FSD include dryers from Niro (e.g., the PSD line of spray driers manufactured by Niro: PHARMASD.™; Chemical or SD line dryers). FSD can be performed in any spray dryer that is configured to allow for the re-introduction of fines into the drying chamber.

Additional post drying, e.g., in a vacuum or fluidized bed dryer or a double cone or biconical post-dryer or a tumble dryer, can be performed if needed/applicable to remove further solvents. In some embodiments, a post-drying step is performed.

To remove the solvent or solvent mixture, vacuum drying, spray drying, fluidized spray drying, tray drying, lyophilization, rotovapping, and other drying procedures may be applied. Applying any of these methods using appropriate processing parameters, according to this disclosure, would provide ivosidenib, or a pharmaceutically acceptable salt thereof in an amorphous state in the final solid dispersion product. Upon use of appropriate conditions (e.g., low outlet temperatures in the spray dryer, use of low boiling point solvents, use of heated gas) that result in a dispersion, e.g., powder, with desirable properties (e.g., median particle size (d50) of 40-200 microns 9 e.g., 40-150 microns), powder bulk density of >0.2 g/ml (e.g., 0.2 to 0.5 g/ml), or >0.25 g/ml, improved powder flowability (e.g., low cohesion forces, low interparticle internal friction); and/or dry powder with low OVIs (Organic Volatile Impurities), e.g., below ICH limits and/or user specifications), the dispersion can be directly compressed into a dosage form.

In some embodiments, the inlet temperature is between about 50° C. and about 200° C., e.g., between about 60° C. and about 150° C., between about 70° C. and about 100° C., between about 60° C. and about 95° C., between about 65° C. and about 85° C., between about 70° C. and about 90° C., between about 85° C. and about 95° C., or between about 70° C. and about 85° C.

In some embodiments, the outlet temperature is between about room temperature (e.g., USP room temperature (e.g., 21±4° C.)) and about 80° C., e.g., between about 25° C. and about 75° C., between about 30° C. and about 65° C., between about 35° C. and about 70° C., between about 40° C. and about 65° C., between about 45° C. and about 60° C., between about 35° C. and about 45° C., between about 35° C. and about 40° C., or between about 37° C. and about 40° C.

In some embodiments, the temperature set points of the fluidized beds (the temperature for each bed being selected independently from the temperature selected for another bed) is between about room temperature (e.g., USP room temperature (e.g., 21±4° C.)) and about 100° C., e.g., between about 30° C. and about 95° C., between about 40° C. and about 90° C., between about 50° C. and about 80° C., between about 60° C. and about 85° C., between about 65° C. and about 95° C., or between about 80° C. and about 95° C.

FSD can be performed on a mixture containing a compound of interest (e.g., a therapeutic agent (e.g., therapeutically active compound), e.g., ivosidenib in any form, or a pharmaceutically acceptable salt thereof). For example, FSD can be performed on a mixture containing ivosidenib, or a pharmaceutically acceptable salt thereof (e.g., and one or more polymer(s), and optionally one or more surfactant(s), and optionally one or more additional excipients(s)) to obtain a solid dispersion of amorphous ivosidenib, or a pharmaceutically acceptable salt thereof, e.g., that can be directly compressed into an oral dosage form (e.g., tablet). Alternatively, the dispersion can be blended with one or more excipients prior to compression.

In one embodiment, the process for preparing a solid dispersion of an amorphous form or mixtures of forms of ivosidenib comprises:
  a) forming a mixture of ivosidenib in any form, or a pharmaceutically acceptable salt thereof, one or more polymer(s), and one or more solvent(s); and
  b) rapidly removing the solvent(s) from the solution to form a solid amorphous dispersion comprising ivosidenib in Form L, alone or in a mixture of forms, or a pharmaceutically acceptable salt thereof, and the one or more polymer(s). The one or more polymer(s) and one or more solvent(s) may be any of those disclosed herein.

In some embodiments of the process, more than one polymorph of ivosidenib may be present. In some embodiments, a second molecule may be present.

In some embodiments, the solvent is removed by spray drying. In some embodiments the solid dispersion is tray dried using a convection tray dryer. In some embodiments, the solid dispersion is screened.

In one embodiment, ivosidenib, or a pharmaceutically acceptable salt thereof, is crystalline. In another embodiment, ivosidenib, or a pharmaceutically acceptable salt thereof, is amorphous. In some embodiments, more than one polymorph of ivosidenib may be present. In some embodiments, a second molecule may be present.

As would be appreciated by one of skill in the art, spray drying may be done and is often done in the presence of an inert gas such as nitrogen. In certain embodiments, processes that involve spray drying may be done in the presence of a supercritical fluid involving carbon dioxide or a mixture including carbon dioxide.

In another embodiment, the process for preparing a solid dispersion of ivosidenib in any form or mixture of forms, or a pharmaceutically acceptable salt thereof, comprises:
  a) forming a mixture of ivosidenib in any form or mixture of forms, or a pharmaceutically acceptable salt thereof, a polymer, and a solvent; and
  b) spray-drying the mixture to form a solid dispersion comprising ivosidenib in any form or mixture of forms, or a pharmaceutically acceptable salt thereof, and the polymer.

Post-drying and/or polishing the wet spray dried dispersion to below ICH or given specifications for residual solvents can optionally be performed.

These processes may be used to prepare the pharmaceutical compositions disclosed herein. The amounts and the features of the components used in the processes may be as disclosed herein.

In some embodiments, the solvent comprises one or more volatile solvent(s) to dissolve or suspend ivosidenib in one or more forms, or a pharmaceutically acceptable salt thereof, and the polymer(s). In some embodiments, the one or more solvent(s) completely dissolves ivosidenib in such form, or a pharmaceutically acceptable salt thereof, and the polymer(s).

In some embodiments, the one or more solvent(s) is a volatile solvent (e.g., methylene chloride, acetone, methanol, ethanol, chloroform, tetrahydrofuran (THF), or a mixture thereof). Examples of suitable volatile solvents include those that dissolve or suspend the therapeutically active compound either alone or in combination with another co-solvent. In some embodiments, the solvent(s) completely dissolves the therapeutically active compound. In some embodiments, the solvent is acetone. In some embodiments, the solvent is methanol.

In some embodiments, the solvent is a non-volatile solvent (e.g., organic acids such as glacial acetic acid, dimethyl sulfoxide (DMSO), dimethylformamide (DMF), or water). In some embodiments, a non-volatile solvent is a component in a solvent system. For example the non-volatile solvent is present as a component in a solvent from about 1% to about 20% w/w (e.g., from about 3% w/w to about 15% w/w, from about 4% w/w to about 12% w/w, or from about 5% w/w to about 10% w/w).

In some embodiments, the solvent is a mixture of solvents. For example, the solvent can include from about 0% to about 30% acetone and from about 70% to about 100% methanol, or the solvent can include from about 0% to about 40% acetone and from about 60% to about 100% methanol. Other exemplary ratios of methanol to acetone include 80:20, 75:25, 70:30, 60:40, 55:45, and 50:50.

In some embodiments, the solvent is a combination of solvents including at least one non-volatile solvent. For example, the solvent is a combination of components that includes both a volatile solvent and a non-volatile solvent. In some embodiments, the solvent system is a combination of a volatile solvent or combination of solvents such as methanol and acetone with a non-volatile solvent such as glacial acetic acid. For example, the solvent system comprises from about 40% to about 80% methanol, from about 20% to about 35% acetone, and from about 1% to about 15% glacial acetic acid (e.g., from about 50% to about 70% methanol, from about 25% to about 30% acetone, and from about 3% to about 12% glacial acetic acid).

In some embodiments, the solvent system is a combination of a volatile solvent or combination of solvents such as methanol and acetone with a non-volatile solvent such as water. For example, the solvent system comprises from about 40% to about 80% methanol, from about 20% to about 35% acetone, and from about 0.1% to about 15% water (e.g., from about 50% to about 70% methanol, from about 25% to about 30% acetone, and from about 1% to about 5% water).

Pharmaceutical Compositions

Pharmaceutical compositions of the solid dispersion may be made by a process described herein. For example, a solid dispersion of: (a) ivosidenib in any of Form A, Form C, Form D, Form E, Form F, Form G, Form H, Form I, Form J, Form K, Form M, and Form N, or a pharmaceutically acceptable salt thereof, and (b) one or more polymer(s), and optionally one or more surfactant(s) and optionally one or more additional excipient(s).

Provided herein are pharmaceutical compositions, comprising: (a) a solid dispersion, comprising ivosidenib in any of Form A, Form C, Form D, Form E, Form F, Form G, Form H, Form I, Form J, Form K, Form M, and Form N, or a pharmaceutically acceptable salt thereof, and a polymer; and (b) one or more pharmaceutically acceptable carrier(s). Examples of pharmaceutically acceptable carriers are fillers, disintegrants, wetting agents, glidants, and lubricants. In some embodiments, more than one polymorph of ivosidenib may be present in the pharmaceutical composition. In some embodiments, a second molecule may be present.

In some embodiments, the pharmaceutical compositions may be orally administered in any orally acceptable dosage form including, but not limited to, capsules, tablets, emulsions and aqueous suspensions, dispersions and solutions.

In some embodiments the pharmaceutical composition is a tablet.

In some embodiments the pharmaceutical composition comprises a directly compressed dosage form of ivosidenib, or a pharmaceutically acceptable salt thereof.

In some embodiments, the pharmaceutical composition also includes a filler. The filler can be, for example, microcrystalline cellulose, lactose, mannitol, ethyl cellulose, sorbitol, starch, sucrose, calcium phosphate, powdered cellulose, silicified microcrystalline cellulose, isomalt, or mixtures thereof. In some embodiments, the filler is microcrystalline cellulose.

In some embodiments, the filler is present in the pharmaceutical composition in an amount of between about 10% w/w and 50% w/w (e.g., between about 15% w/w and about 45% w/w; between about 20% w/w and about 40% w/w; between about 25% w/w and about 35% w/w; or between about 28% w/w and about 32% w/w). In some embodiments, the filler is present in the pharmaceutical composition in an amount of from about 20% w/w to about 35% w/w, for example from about 25% w/w to about 34% w/w, or from about 26% w/w to about 33% w/w, or from about 27% w/w to about 32% w/w, for example, about 28% w/w, about 28.5% w/w, about 29% w/w, about 29.5% w/w about 30% w/w, about 30.5% w/w, about 31% w/w, or about 31.5% w/w. In some embodiments, the filler is present in the pharmaceutical composition in an amount of about 29% w/w, about 29.1% w/w, about 29.2% w/w, about 29.3% w/w, about 29.4% w/w, about 29.5% w/w, about 29.6% w/w, about 29.7% w/w, about 29.8% w/w, about 29.9% w/w, or about 30% w/w. In some embodiments, the filler is present in the pharmaceutical composition in an amount of between about 25% w/w and about 35% w/w. In some embodiments, the filler is present in the pharmaceutical composition in an amount of about 29.5% w/w.

In some embodiments, the pharmaceutical composition also includes a disintegrant. The disintegrant can be, for example, colloidal silicon dioxide, powdered cellulose, calcium silicate, crospovidone, calcium alginate, methyl cellulose, chitosan, carboxy methyl cellulose, croscarmellose sodium, carboxymethyl starch, sodium alginate, sodium starch glycolate, pregelatinized starch, or mixtures thereof. In some embodiments, the disintegrant is croscarmellose sodium.

In some embodiments, the disintegrant is present in the pharmaceutical composition in an amount of between about 1% w/w and 15% w/w (e.g., between about 3% w/w and about 12% w/w; between about 4% w/w and about 10% w/w; between about 5% w/w and about 7% w/w; or between about 6% w/w and about 7% w/w). In some embodiments, the disintegrant is present in the pharmaceutical composition in an amount of about 3% w/w, about 3.5% w/w, about 4% w/w, about 49.5% w/w about 5% w/w, about 5.5% w/w, about 6% w/w, or about 6.5% w/w, about 7% w/w, about 7.5% w/w, about 8% w/w, about 8.5% w/w, about 9% w/w, about 9.5% w/w, or about 10% w/w. In some embodiments, the disintegrant is present in the pharmaceutical composition in an amount of between about 5% w/w and about 7% w/w. In some embodiments, the disintegrant is present in the pharmaceutical composition in an amount of about 6% w/w.

In some embodiments, the pharmaceutical composition also includes a wetting agent. The wetting agent can be, for example, sodium lauryl sulfate, sodium dodecyl sulfate, polysorbates (such as Tween 20 and Tween 80), poloxamers (such as Poloxamer 335 and Poloxamer 407), glyceryl monooleate, or mixtures thereof. In some embodiments, the wetting agent is sodium lauryl sulfate.

In some embodiments, the wetting agent is present in the pharmaceutical composition in an amount of between about 0.1% w/w and 2% w/w (e.g., between about 0.5% w/w and about 2% w/w; between about 0.5% w/w and about 1.5% w/w; or between about 1% w/w and about 1.5% w/w). In some embodiments, the wetting agent is present in the pharmaceutical composition in an amount of about 0.1% w/w, about 0.2% w/w, about 0.3% w/w, about 0.4% w/w about 0.5% w/w, about 0.6% w/w, about 0.7% w/w, or about 0.8% w/w, about 0.9% w/w, about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, or about 2% w/w. In some embodiments, the wetting agent is present in the pharmaceutical composition in an amount of between about 0.5% w/w and about 1.5% w/w. In some embodiments, the wetting agent is present in the pharmaceutical composition in an amount of about 1% w/w.

In some embodiments, the pharmaceutical composition also includes a glidant. The glidant can be, for example, silicon dioxide, colloidal silicon dioxide, tribasic calcium phosphate, magnesium stearate, magnesium trisilicate, powdered cellulose, talc, starch, and mixtures thereof. In some embodiments, the glidant is colloidal silicon dioxide.

In some embodiments, the glidant is present in the pharmaceutical composition in an amount of between about 0.1% w/w and 5% w/w (e.g., between about 1% w/w and about 4% w/w; between about 1% w/w and about 3% w/w; or between about 1.5% w/w and about 2.5% w/w). In some embodiments, the glidant is present in the pharmaceutical composition in an amount of about 0.5% w/w, about 1% w/w, about 1.5% w/w, about 2% w/w about 2.5% w/w, about 3% w/w, about 3.5% w/w, or about 4% w/w, about 4.5% w/w, or about 5% w/w. In some embodiments, the glidant is present in the pharmaceutical composition in an amount of about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, 2.1% w/w, about 2.2% w/w, about 2.3% w/w, about 2.4% w/w, about 2.5% w/w, about 2.6% w/w, about 2.7% w/w, about 2.8% w/w, about 2.9% w/w, or about 3% w/w. In some embodiments, the glidant is present in the pharmaceutical composition in an amount of between about 1% w/w and about 3% w/w. In some embodiments, the glidant is present in the pharmaceutical composition in an amount of about 2% w/w.

In some embodiments, the pharmaceutical composition also includes a lubricant. The lubricant can be, for example, magnesium stearate, talc, sodium stearyl fumarate, glyceryl behenate, hydrogenated vegetable oil, zinc stearate, calcium stearate, sucrose stearate, polyvinyl alcohol, magnesium lauryl sulfate, or mixtures thereof. In some embodiments, the lubricant is magnesium stearate.

In some embodiments, the lubricant is present in the pharmaceutical composition in an amount of between about 0.1% w/w and 5% w/w (e.g., between about 1% w/w and about 4% w/w; between about 1% w/w and about 3% w/w; or between about 1% w/w and about 2% w/w). In some embodiments, the lubricant is present in the pharmaceutical composition in an amount of about 0.5% w/w, about 1% w/w, about 1.5% w/w, about 2% w/w about 2.5% w/w, about 3% w/w, about 3.5% w/w, or about 4% w/w, about 4.5% w/w, or about 5% w/w. In some embodiments, the lubricant is present in the pharmaceutical composition in an amount of about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, 2.1% w/w, about 2.2% w/w, about 2.3% w/w, about 2.4% w/w, or about 2.5% w/w. In some embodiments, the lubricant is present in the pharmaceutical composition in an amount of between about 0.5% w/w and about 2.5% w/w. In some embodiments, the lubricant is present in the pharmaceutical composition in an amount of about 1.5% w/w.

In some embodiments, the solid dispersion makes up about 25% to 85% by weight of the total weight of the pharmaceutical composition. In some embodiments, the solid dispersion makes up about 50% to about 70% by weight of the total weight of the pharmaceutical composition.

In some embodiments, the ivosidenib in any form, or a pharmaceutically acceptable salt thereof makes up about 15% to 45% of the total weight of the pharmaceutical composition, and the one or more polymer(s) makes up about 15% to 45% of the total weight of the pharmaceutical composition.

In some embodiments, the ivosidenib in any form, or a pharmaceutically acceptable salt thereof makes up about 20% w/w of the pharmaceutical composition, the one or more polymer(s) makes up about 40% w/w of the pharmaceutical composition.

In some embodiments, the ivosidenib in any form, or a pharmaceutically acceptable salt thereof makes up about 25% w/w of the pharmaceutical composition, the one or more polymer(s) makes up about 35% w/w of the pharmaceutical composition.

In some embodiments, the ivosidenib in any form, or a pharmaceutically acceptable salt thereof makes up about 30% w/w of the pharmaceutical composition, the one or more polymer(s) makes up about 30% w/w of the pharmaceutical composition.

In some embodiments, the ivosidenib in any form, or a pharmaceutically acceptable salt thereof makes up about 35% w/w of the pharmaceutical composition, the one or more polymer(s) makes up about 25% w/w of the pharmaceutical composition.

In some embodiments, the solid dispersion makes up from between about 50% w/w to about 70% w/w of the pharmaceutical composition, the filler makes up from between about 25% w/w to about 35% w/w of the pharmaceutical composition, the disintegrant makes up from between about 5% w/w to about 7% w/w of the pharmaceutical composition, the wetting agent makes up from between about 0.5% w/w to about 1.5% w/w of the pharmaceutical composition, the glidant makes up from between about 1% w/w to about 3% w/w of the pharmaceutical composition, the lubricant makes up from between about 0.5% w/w to about 2.5% w/w of the pharmaceutical composition thereby totaling 100% by weight of the composition.

In some embodiments, the solid dispersion makes up about 60% w/w of the pharmaceutical composition, the filler makes up about 29.5% w/w of the pharmaceutical composition, the disintegrant about 6% w/w, the wetting agent about 1% w/w, the glidant about 2% w/w, and the lubricant about 1.5% w/w.

In some embodiments, the pharmaceutical composition comprises, from between about 25% w/w to about 35% w/w of ivosidenib in any form, or a pharmaceutically acceptable salt thereof, from between about 25% w/w to about 35% w/w of hypromellose acetate succinate (HPMCAS), from between about 25% w/w to about 35% w/w of microcrystalline cellulose, from between about 5% w/w to about 7% w/w croscarmellose sodium, from between about 0.5% w/w to about 1.5% w/w sodium lauryl sulfate, about from between about 1% w/w to about 3% w/w colloidal silicon dioxide, and rom between about 0.5% w/w to about 2.5% w/w of magnesium stearate, thereby totaling 100% by weight of the composition.

In some embodiments, the pharmaceutical composition comprises, about 30% w/w of ivosidenib, or a pharmaceutically acceptable salt thereof, about 30% w/w of hypromellose acetate succinate (HPMCAS), about 29.5% w/w of microcrystalline cellulose, about 6% w/w croscarmellose sodium, about 1% w/w sodium lauryl sulfate, about 2% w/w colloidal silicon dioxide, and about 1.5% w/w of magnesium stearate.

In some embodiments, the solid dispersion, filler, disintegrant, wetting agent, glidant, and lubricant are added intragranularly. In some embodiments, an additional amount of the filler, disintegrant, glidant, and lubricant are added extragranularly.

In some embodiments, the pharmaceutical composition comprises, the following intragranularly added components: the solid dispersion makes up from about 50% w/w to about 70% w/w of the pharmaceutical composition, the filler makes up from about 18% w/w to about 26% w/w of the pharmaceutical composition, disintegrant makes up from about 2% w/w to about 6% w/w of the pharmaceutical composition, wetting agent makes up from about 0.5% w/w to about 1.5% w/w of the pharmaceutical composition, glidant makes up from about 0.5% w/w to about 1.5% w/w of the pharmaceutical composition, and lubricant makes up from about 0.25% w/w to about 1% w/w of the pharmaceutical composition.

In some embodiments, a the pharmaceutical composition comprises the following extragranularly added components: an additional amount of the filler makes up from about 4% w/w to about 12% w/w of the pharmaceutical composition, an additional amount of the disintegrant makes up from about 1% w/w to about 3% w/w of the pharmaceutical composition, an additional amount of the glidant makes up from about 0.5% w/w to about 1.5% w/w of the pharmaceutical composition, and an additional amount of the lubricant makes up from about 0.5% w/w to about 1.5% w/w of the pharmaceutical composition, and are added extragranularly.

In some embodiments, the pharmaceutical composition comprises, the following intragranularly added components: the solid dispersion makes up about 60% w/w of the pharmaceutical composition, the filler makes up about 21.5% w/w of the pharmaceutical composition, disintegrant makes up about 4% w/w of the pharmaceutical composition, wetting agent makes up about 1% w/w of the pharmaceutical composition, glidant makes up about 1% w/w of the pharmaceutical composition, and lubricant makes up about 0.5% w/w of the pharmaceutical composition.

In some embodiments, a the pharmaceutical composition comprises the following extragranularly added components: an additional amount of the filler makes up about 8% w/w of the pharmaceutical composition, an additional amount of the disintegrant makes up about 2% w/w of the pharmaceutical composition, an additional amount of the glidant makes up about 1% w/w of the pharmaceutical composition, and an additional amount of the lubricant makes up about 1% w/w of the pharmaceutical composition, and are added extragranularly.

In some embodiments, the pharmaceutical composition comprises, the following intragranularly added components: the solid dispersion comprising ivosidenib, or a pharmaceutically acceptable salt thereof, and hypromellose acetate succinate (HPMCAS), makes up from about 50% w/w to about 70% w/w of the pharmaceutical composition, microcrystalline cellulose makes up from about 18% w/w to about 26% w/w of the pharmaceutical composition, croscarmellose sodium makes up from about 2% w/w to about 6% w/w of the pharmaceutical composition, sodium lauryl sulfate makes up from about 0.5% w/w to about 1.5% w/w of the pharmaceutical composition, colloidal silicon dioxide makes up from about 0.5% w/w to about 1.5% w/w of the pharmaceutical composition, and magnesium stearate makes up from about 0.25% w/w to about 1% w/w of the pharmaceutical composition.

In some embodiments, a the pharmaceutical composition comprises the following extragranularly added components: an additional amount of microcrystalline cellulose makes up from about 4% w/w to about 12% w/w of the pharmaceutical composition, an additional amount of croscarmellose sodium makes up from about 1% w/w to about 3% w/w of the pharmaceutical composition, an additional amount of colloidal silicon dioxide makes up from about 0.5% w/w to about 1.5% w/w of the pharmaceutical composition, and an additional amount of magnesium stearate makes up from about 0.5% w/w to about 1.5% w/w of the pharmaceutical composition, and are added extragranularly.

In some embodiments, the pharmaceutical composition comprises, the following intragranularly added components: the solid dispersion comprising ivosidenib, or a pharmaceutically acceptable salt thereof, and hypromellose acetate succinate (HPMCAS), makes up about 60% w/w of the pharmaceutical composition, microcrystalline cellulose makes up about 21.5% w/w of the pharmaceutical composition, croscarmellose sodium makes up about 4% w/w of the pharmaceutical composition, sodium lauryl sulfate makes up about 1% w/w of the pharmaceutical composition, colloidal silicon dioxide makes up about 1% w/w of the pharmaceutical composition, and magnesium stearate makes up about 0.5% w/w of the pharmaceutical composition.

In some embodiments, a the pharmaceutical composition comprises the following extragranularly added components: an additional amount of microcrystalline cellulose makes up about 8% w/w of the pharmaceutical composition, an additional amount of croscarmellose sodium makes up about 2% w/w of the pharmaceutical composition, an additional amount of colloidal silicon dioxide makes up about 1% w/w of the pharmaceutical composition, and an additional amount of magnesium stearate makes up about 1% w/w of the pharmaceutical composition, and are added extragranularly.

A subject may be administered a dose of ivosidenib in any form, or a pharmaceutically acceptable salt thereof. Lower or higher doses than those recited above may be required. Specific dosage and treatment regimens for any particular subject will depend upon a variety of factors, including the activity of the specific compound, employed, the age, body weight, general health status, sex, diet, time of administration, rate of excretion, drug combination, the severity and course of the disease, condition or symptoms, the subject's disposition to the disease, condition or symptoms, and the judgment of the treating physician.

Upon improvement of a subject's condition, a maintenance dose of a compound, composition or combination of one aspect of this invention may be administered, if necessary. Subsequently, the dosage or frequency of administration, or both, may be reduced, as a function of the symptoms, to a level at which the improved condition is retained when the symptoms have been alleviated to the desired level. Subjects may, however, require intermittent treatment on a long-term basis upon any recurrence of disease symptoms.

Methods of Use

The inhibitory activities of ivosidenib in any form, and pharmaceutically acceptable salts thereof provided herein against IDH1 mutants (e.g., IDH1R132H or IDH1R132C) can be tested by methods described in Example A of PCT Publication No. WO 2013/107291 and US Publication No. US 2013/0190249, hereby incorporated by reference in their entirety, or analogous methods.

Provided is a method for treating an advanced solid tumor, such as glioma, intrahepatic cholangiocarcinomas (IHCC), chondrosarcoma, prostate cancer, colon cancer, melanoma, or non-small cell lung cancer (NSCLC), each characterized by the presence of a mutant allele of IDH1, comprising administering to a subject in need thereof a pharmaceutical composition comprising: (a) ivosidenib, or a pharmaceutically acceptable salt thereof, as part of a solid dispersion, and optionally (b) one or more pharmaceutically acceptable carrier(s). In one embodiment, the advanced solid tumor, such as glioma, intrahepatic cholangiocarcinomas (IHCC), chondrosarcoma, prostate cancer, colon cancer, melanoma, or non-small cell lung cancer (NSCLC), to be treated is characterized by a mutant allele of IDH1, wherein the IDH1 mutation results in a new ability of the enzyme to catalyze the NADPH-dependent reduction of α-ketoglutarate to R(−)-2-hydroxyglutarate in a patient. In one aspect of this embodiment, the mutant IDH1 has an R132X mutation. In one aspect of this embodiment, the R132X mutation is selected from R132H, R132C, R132L, R132V, R132S and R132G. In another aspect, the R132X mutation is R132H or R132C. In yet another aspect, the R132X mutation is R132H. In such a method of treatment, more than one polymorph of ivosidenib may be present. In some embodiments, a second molecule may be present.

Advanced solid tumors, such as glioma, intrahepatic cholangiocarcinomas (IHCC), chondrosarcoma, prostate cancer, colon cancer, melanoma, or non-small cell lung cancer (NSCLC), each characterized by the presence of a mutant allele of IDH1 can be analyzed by sequencing cell samples to determine the presence and specific nature of (e.g., the changed amino acid present at) a mutation at amino acid 132 of IDH1.

Without being bound by theory, applicants believe that mutant alleles of IDH1 wherein the IDH1 mutation results in a new ability of the enzyme to catalyze the NADPH-dependent reduction of α-ketoglutarate to R(−)-2-hydroxyglutarate, and in particular R132H mutations of IDH1, characterize a subset of all types of cancers, without regard to their cellular nature or location in the body. Thus, the compounds, and methods of one aspect of this invention are useful to treat advanced solid tumors, such as glioma, intrahepatic cholangiocarcinomas (IHCC), chondrosarcoma, prostate cancer, colon cancer, melanoma, or non-small cell lung cancer (NSCLC), each characterized by the presence of a mutant allele of IDH1 imparting such activity and in particular an IDH1 R132H or R132C mutation.

In one embodiment, the efficacy of treatment of advanced solid tumors, such as glioma, intrahepatic cholangiocarcinomas (IHCC), chondrosarcoma, prostate cancer, colon cancer, melanoma, or non-small cell lung cancer (NSCLC), each characterized by the presence of a mutant allele of IDH1 is monitored by measuring the levels of 2HG in the subject. Typically levels of 2HG are measured prior to treatment, wherein an elevated level is indicated for the use of ivosidenib, or a pharmaceutically acceptable salt thereof, to treat the advanced solid tumors, such as glioma, intrahepatic cholangiocarcinomas (IHCC), chondrosarcoma, prostate cancer, colon cancer, melanoma, or non-small cell lung cancer (NSCLC), each characterized by the presence of a mutant allele of IDH1. Once the elevated levels are established, the level of 2HG is determined during the course of and/or following termination of treatment to establish efficacy. In certain embodiments, the level of 2HG is only determined during the course of and/or following termination of treatment. A reduction of 2HG levels during the course of treatment and following treatment is indicative of efficacy. Similarly, a determination that 2HG levels are not elevated during the course of or following treatment is also indicative of efficacy. Typically, these 2HG measurements will be utilized together with other well-known determinations of efficacy of cancer treatment, such as reduction in number and size of tumors and/or other cancer-associated lesions, evaluation of bone marrow biopsies and/or aspirates, complete blood counts and examination of peripheral blood films, improvement in the general health of the subject, and alterations in other biomarkers that are associated with cancer treatment efficacy.

2HG can be detected in a sample by the methods of PCT Publication No. WO WO/2011/050210 and US Publication No. US2012/0121515 hereby incorporated by reference in their entirety, or by analogous methods.

In one embodiment the advanced solid tumor, such as glioma, intrahepatic cholangiocarcinomas (IHCC), chondrosarcoma, prostate cancer, colon cancer, melanoma, or non-small cell lung cancer (NSCLC), is a tumor wherein at least 30, 40, 50, 60, 70, 80 or 90% of the tumor cells carry an IDH1 mutation, and in particular an IDH1 R132H or R132C mutation, at the time of diagnosis or treatment.

In another embodiment, the advanced solid tumor to be treated is glioma, characterized by the presence of a mutant allele of IDH1. In another embodiment, the glioma has recurred following standard therapy. In another embodiment, the glioma has progressed following standard therapy. In another embodiment, the glioma has not responded to standard therapy.

In another embodiment, the advanced solid tumor to be treated is IHCC, characterized by the presence of a mutant allele of IDH1. In another embodiment, the IHCC has recurred following standard therapy. In another embodiment, the IHCC has progressed following standard therapy. In another embodiment, the IHCC has not responded to standard therapy.

In another embodiment, the advanced solid tumor to be treated is chondrosarcoma, characterized by the presence of a mutant allele of IDH1. In another embodiment, the chondrosarcoma has recurred following standard therapy. In another embodiment, the chondrosarcoma has progressed following standard therapy. In another embodiment, the chondrosarcoma has not responded to standard therapy.

In another embodiment, the advanced solid tumor to be treated is prostate cancer, characterized by the presence of a mutant allele of IDH1. In another embodiment, the prostate cancer has recurred following standard therapy. In another embodiment, the prostate cancer has progressed following standard therapy. In another embodiment, the prostate cancer has not responded to standard therapy.

In another embodiment, the advanced solid tumor to be treated is colon cancer, characterized by the presence of a mutant allele of IDH1. In another embodiment, the colon cancer has recurred following standard therapy. In another embodiment, the colon cancer has progressed following standard therapy. In another embodiment, the colon cancer has not responded to standard therapy.

In another embodiment, the advanced solid tumor to be treated is melanoma, characterized by the presence of a mutant allele of IDH1. In another embodiment, the melanoma) has recurred following standard therapy. In another embodiment, the melanoma has progressed following standard therapy. In another embodiment, the melanoma has not responded to standard therapy.

In another embodiment, the advanced solid tumor to be treated is non-small cell lung cancer (NSCLC), characterized by the presence of a mutant allele of IDH1. In another embodiment, the non-small cell lung cancer (NSCLC) has recurred following standard therapy. In another embodiment, the non-small cell lung cancer (NSCLC) has progressed following standard therapy. In another embodiment, the non-small cell lung cancer (NSCLC) has not responded to standard therapy.

Treatment methods described herein can additionally comprise various evaluation steps prior to and/or following treatment with a pharmaceutical composition comprising: (a) ivosidenib, or a pharmaceutically acceptable salt thereof, as part of a solid dispersion, and optionally (b) one or more pharmaceutically acceptable carrier(s).

In one embodiment, prior to and/or after treatment with a pharmaceutical composition comprising: (a) ivosidenib, or a pharmaceutically acceptable salt thereof, as part of a solid dispersion, and optionally (b) one or more pharmaceutically acceptable carrier(s), the method further comprises evaluating the growth, size, weight, invasiveness, stage and/or other phenotype of the advanced solid tumor, such as glioma, intrahepatic cholangiocarcinomas (IHCC), chondrosarcoma, prostate cancer, colon cancer, melanoma, or non-small cell lung cancer (NSCLC), each characterized by the presence of a mutant allele of IDH1.

In one embodiment, prior to and/or after treatment with a pharmaceutical composition comprising: (a) ivosidenib, or a pharmaceutically acceptable salt thereof, as part of a solid dispersion, and optionally (b) one or more pharmaceutically acceptable carrier(s), the method further comprises evaluating the IDH1 genotype of the advanced solid tumors, such as glioma, intrahepatic cholangiocarcinomas (IHCC), chondrosarcoma, prostate cancer, colon cancer, melanoma, or non-small cell lung cancer (NSCLC), each characterized by the presence of a mutant allele of IDH1. This may be achieved by ordinary methods in the art, such as DNA sequencing, immuno analysis, and/or evaluation of the presence, distribution or level of 2HG.

In one embodiment, prior to and/or after treatment with a pharmaceutical composition comprising: (a) ivosidenib, or a pharmaceutically acceptable salt thereof, as part of a solid dispersion, and optionally (b) one or more pharmaceutically acceptable carrier(s), the method further comprises determining the 2HG level in the subject. This may be achieved by spectroscopic analysis, e.g., magnetic resonance-based analysis, e.g., MRI and/or MRS measurement, sample analysis of bodily fluid, such as blood, plasma, urine, or spinal cord fluid analysis, or by analysis of surgical material, e.g., by mass-spectroscopy (e.g. LC-MS, GC-MS), or any of the methods described herein.

Test compounds for the experiments described herein were employed in free or salt form.

The specific responses observed may vary according to and depending on the particular active compound selected or whether there are present carriers, as well as the type of formulation and mode of administration employed, and such expected variations or differences in the results are contemplated in accordance with practice of the present invention.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

The patent and scientific literature referred to herein establishes knowledge that is available to those with skill in the art. Unless otherwise defined, all technical and scientific terms used herein have the same meaning as commonly understood by one of ordinary skill in the art to which this invention belongs. The issued patents, applications, and references that are cited herein are hereby incorporated by reference to the same extent as if each was specifically and individually indicated to be incorporated by reference. In the case of inconsistencies, the present disclosure, including definitions, will control.

What is claimed is:

1. A solid state form E of a methyl isobutyl ketone (MIBK) solvate of a compound of Formula (I)

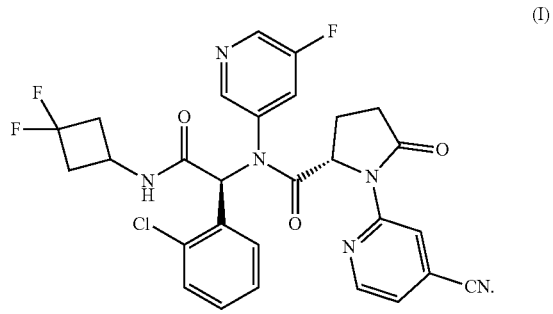 [SMILES: N#Cc1ccnc(N2C(=O)CC[C@H]2C(=O)N(c2cncc(F)c2)[C@H](C(=O)NC2CC(F)(F)C2)c2ccccc2Cl)c1]

(ivosidenib), having (i) an x-ray powder diffraction pattern comprising peaks at 6.3±0.2° 2θ, 11.6±0.2° 2θ, 12.0±0.2° 2θ, 17.1±0.2° 2θ, and 21.0±0.2 2θ.

2. The solid state form E of claim 1, wherein the solid state form is further characterized by (i) a thermogravimetric analysis having an about 9.5 wt % weight loss before 145.0° C. or (ii) a differential scanning calorimetry thermogram comprising an endotherm at 93.1° C.

3. The solid state form E of claim 1, wherein the solid state form is further characterized by a $^1$H NMR pattern comprising a doublet peak at about 0.92 ppm indicating the two methyl groups of methyl isobutyl ketone.

4. An anhydrous solid state form M of a compound of Formula (I)

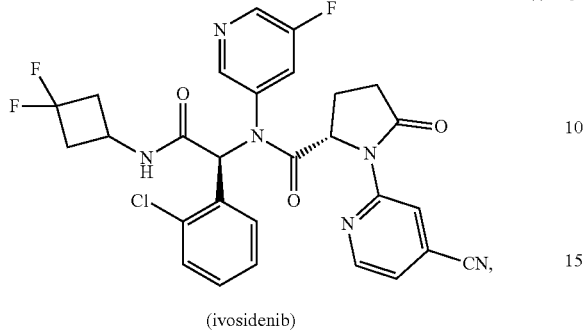

(ivosidenib)

characterized by (i) an x-ray powder diffraction pattern comprising peaks at 11.4±0.2° 2θ, 17.7±0.2° 2θ, 17.8±0.2° 2θ, 19.7±0.2° 2θ, and 21.4±0.2° 2θ.

5. The anhydrous solid state form M of claim 4, wherein the solid state form is further characterized by (i) a differential scanning calorimetry thermogram comprising an endothermic peak at 170.0° C. or (ii) a differential scanning calorimetry thermogram comprising an endothermic peak at 170.5° C.

* * * * *